(12) United States Patent
Habtemariam et al.

(10) Patent No.: US 9,408,853 B2
(45) Date of Patent: Aug. 9, 2016

(54) IRIDIUM/RHODIUM ANTI-CANCER COMPOUNDS

(75) Inventors: Abraha Habtemariam, Edinburgh (GB); Zhe Liu, Coventry (GB); Joan Josep Soldevila, Barcelona (ES); Ana Maria Pizarro, Madrid (ES); Peter John Sadler, Warwks (GB)

(73) Assignee: University of Warwick, Coventry (GB)

( * ) Notice: Subject to any disclaimer, the term of this patent is extended or adjusted under 35 U.S.C. 154(b) by 305 days.

(21) Appl. No.: 13/698,965

(22) PCT Filed: May 20, 2011

(86) PCT No.: PCT/GB2011/000776
§ 371 (c)(1),
(2), (4) Date: Nov. 19, 2012

(87) PCT Pub. No.: WO2011/148124
PCT Pub. Date: Dec. 1, 2011

(65) Prior Publication Data
US 2013/0065864 A1  Mar. 14, 2013

(30) Foreign Application Priority Data
May 22, 2010  (GB) .................................. 1008584.3

(51) Int. Cl.
| | | |
|---|---|---|
| A61K 31/655 | (2006.01) |
| A61K 31/555 | (2006.01) |
| A61K 31/28 | (2006.01) |
| C07F 15/00 | (2006.01) |
| C07F 17/02 | (2006.01) |

(52) U.S. Cl.
CPC ............... *A61K 31/555* (2013.01); *A61K 31/28* (2013.01); *C07F 17/02* (2013.01)

(58) Field of Classification Search
CPC ... A61K 31/655; A61K 31/555; A61K 31/28; C07F 15/00
USPC .......... 514/150, 185, 188, 492; 546/2, 10, 12; 556/41, 137
See application file for complete search history.

(56) References Cited

U.S. PATENT DOCUMENTS

| | | | | |
|---|---|---|---|---|
| 5,284,644 | A * | 2/1994 | Kruper et al. ................ | 424/1.53 |
| 7,709,654 | B2 * | 5/2010 | Smith et al. .................... | 548/235 |
| 2011/0039815 | A1 * | 2/2011 | Youngs et al. ................ | 514/184 |

FOREIGN PATENT DOCUMENTS

| | | |
|---|---|---|
| EP | 1471567 A1 | 10/2004 |
| EP | 2543675 A1 | 1/2013 |
| WO | 2011010072 A2 | 1/2011 |

OTHER PUBLICATIONS

Schneider et al. From Mononuclear (C5H5CH2C5H4)M to Unsymmetrical Dinuclear M(C5H4CH2C5H4)M and heterodinuclear M(C5H4CH2C5H4)M" Transition-Metal Complexes 1. Organometallics (1993). 12(11):4420-4430.

* cited by examiner

*Primary Examiner* — Raymond Henley, III
(74) *Attorney, Agent, or Firm* — Hema Vakharia-Rao; Nixon Peabody LLP

(57) ABSTRACT

The present invention relates to novel iridium and/or rhodium containing complexes for use as a cytotoxic, such as an anti-cancer agent. There is also provided a method of preparing said compounds.

12 Claims, 16 Drawing Sheets

(G)  (H)

(I)  (J)

(K)  (L)

IRIDIUM/RHODIUM ANTI-CANCER COMPOUNDS

CROSS-REFERENCE TO RELATED APPLICATIONS

The present application is the National Phase of International Application PCT/GB2011/000776, filed May 20, 2011, which designated the United States. This application also includes a claim of priority under 35 U.S.C. §119(a) and §365(b) to British patent application No. 1008584.3 filed May 22, 2010.

FIELD OF THE INVENTION

The present invention relates to novel iridium and/or rhodium containing complexes for use as cytotoxic, such as anti-cancer agents. There is also provided a method of preparing said compounds.

BACKGROUND OF THE INVENTION

A significant development of organometallic chemistry in recent years has been the increasing use of pentamethylcyclopentadienyl compounds. Not only are such compounds usually more soluble in organic solvents and more readily crystallized than their unsubstituted cyclopentadienyl analogs, but they are generally more stable as a result of the steric and electron-donation effects of the five methyl groups. This is particularly so for the ($\eta^5$-pentamethylcyclopentadienyl) iridium complexes, where the $\eta^5$-$C_5Me_5$ acts as an excellent ligand toward Ir(III) since it is displaced only with considerable difficulty.[1]

Sheldrick's group in Germany has studied the biological activity of ($\eta^5$-pentamethyl cyclopentadienyl)iridium complexes with polypyridyl ligands. Their work focuses on the intercalative binding properties of polypyridyl (pp) ligands (pp=dpq, dppz and dppn) into DNA. Recently they have showed that [($\eta^5$-$C_5Me_5$)IrCl(dppz)](CF$_3$SO$_3$) and [($\eta^5$-$C_5Me_5$)Ir((NMe$_2$)$_2$CS)(dppn)](CF$_3$SO$_3$)$_2$ possess in vitro cytotoxic activity towards MCF-7 and HT-29 cancer cell lines, while [($\eta^5$-$C_5Me_5$)Ir(phen)Cl](CF$_3$SO$_3$) and [($\eta^5$-$C_5Me_5$) Ir(en)Cl](CF$_3$SO$_3$) are inactive against MCF-7 (breast cancer).[2] Furthermore they have studied the influence of polypyridyl ligands (pp=dpq, dppz and dppn) and monodentate ligands (L=Cl, (NH$_2$)$_2$CS, (NMe$_2$)$_2$CS) on DNA intercalation (see FIG. 1).[3] They also found that the complexes [IrCl$_3$(DMSO)(pp)] (pp=phen, dpq, dppz, dppn), (FIG. 1), are potent cytotoxic agents toward the human cell lines MCF-7 and HT-29 and their IC$_{50}$ values are dependent on the size of the polypyridyl ligands.[4] Their work on iridium and rhodium polypyridyl complexes of general formula [Me(hal)$_3$(sol)(pp)], in which hal is a halogenide and sol is a solvent, is described in EP2072521.

DNA binding of the type [($\eta^5$-$C_5Me_5$)Ir(Aa)(dppz)](CF$_3$SO$_3$)$_n$ containing S-coordinated amino acids has been studied and X-ray structure of [($\eta^5$-$C_5Me_5$)Ir(9-EtG)(phen)](CF$_3$SO$_3$)$_2$ has been reported.[5]

The biological activity of three novel indium(III) complexes with 1,2-naphthoquinone-1-oximato ligand are also described.[6] The complex [($\eta^5$-$C_5Me_5$)Ir (pyTz)Cl]$^+$ containing the 2-(pyridine-2-yl)thiazole (pyTz) N,N-chelating ligand is reported to be inactive towards human ovarian cancer cell lines A2780 and A2780cisR (cisplatin-resistant).[7]

SUMMARY OF THE INVENTION

The present invention is based on studies on for monofunctional Ir$^{III}$ complexes [($\eta^5$-Cp$^x$)Ir(LL)Cl]$^{0/+}$, in which Cp$^x$=Cp*, $\eta^5$-tetramethyl(phenyl)cyclopentadienyl (Cp$^{xph}$) and $\eta^6$-tetramethyl(biphenyl)cyclopentadienyl (Cp$^{xbiph}$) ligands (Chart 1), and the LL is an N,N-bound ethylenediamine, 2,2'-bipyridine, 1,10-phenanthroline, N,O-bound picolinate ligand, O,O-bound acetylacetonate (acac) ligand and C,N-bound ligands. The rate of hydrolysis, acidity of the aqua adducts, interactions with nucleobases, the uptake and partitioning of these complexes in cells and relationship to cancer cell cytotoxicity have been studied.

Without wishing to be bound by theory, it has been observed that certain substituents on the cyclopentadienyl ring significantly enhance cancer cell cytotoxicity, in particular the phenyl substituents in $\eta^5$-tetramethyl(phenypcyclopenta dienyl (Cp$^{xph}$) and $\eta^5$-tetramethyl(biphenyl)cyclopentadienyl (Cp$^{xbiph}$) ligands.

In a first aspect there is provided a compound of formula (I), optionally for use as a cytotoxic agent, especially an anti-cancer agent:

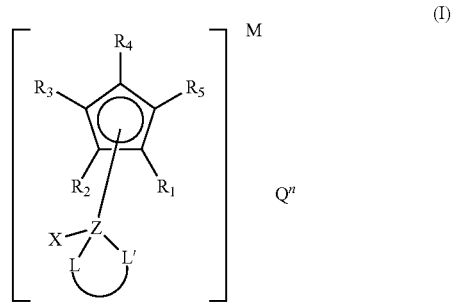

(I)

or a dinuclear or polynuclear from thereof, wherein Z is iridium or rhodium

X is a halo or donor ligand;

Each $R_1$-$R_5$ is independently H or methyl, with the proviso that at least one of said $R_1$-$R_5$ groups is independently selected from a substituted or unsubstituted alkyl or alkenyl, such as an unsubstituted $C_2$-$C_{10}$ alkyl or alkenyl; or a substituted $C_1$-$C_{10}$ alkyl or alkenyl, aryl such as a substituted or unsubstituted saturated or unsaturated cyclic or heterocyclic ring, $NH_2$; $NO_2$; OR; COOR wherein a is a $C_1$-$C_6$ alkyl or alkenyl or an aryl such as a saturated or unsaturated cyclic or heterocyclic ring or a trimethylsilyl.

L-L' is a chelating ligand;

Q is an ion and is either present or absent; and

M and n are charges, independently either absent or selected from a positive or negative whole integer, or solvates or prodrugs thereof and physiologically active derivatives thereof.

with the proviso that when $R_1$-$R_5$ are each independently methyl, then L and L' are not each independently N or O (ie N,N;O,O; or N,O). Preferably when $R_1$-$R_5$ are each independently methyl, L-L' is C and N.

In a preferred embodiment the present invention provides a compound of formula (ii) for use as a cytotoxic agent, especially an anti-cancer agent:

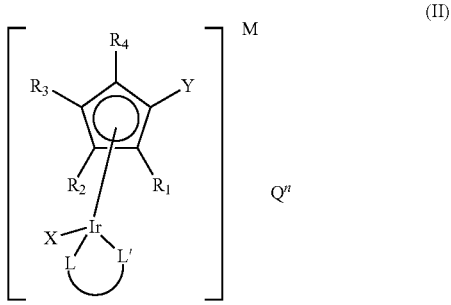

(II)

or a dinuclear or polynuclear form thereof,
where X, Z, L-L', Q, M and n are the same as defined in relation to the first aspect, $R_1$-$R_4$ are H or methyl and Y is independently selected from a substituted or unsubstituted alkyl or alkenyl, such as an unsubstituted $C_2$-$C_{10}$ alkyl or alkenyl; or a substituted $C_1$-$C_{10}$ alkyl or alkenyl, aryl such as a substituted or unsubstituted saturated or unsaturated cyclic or heterocyclic ring, $NH_2$; $NO_2$; $OR^1$; $COOR^1$ wherein $R^1$ is a $C_1$-$C_6$ alkyl or alkenyl or an aryl such as a saturated or unsaturated cyclic or heterocyclic ring or a trimethylsilyl. Preferably Z is iridium.

When H or methyl, preferably, $R_1$-$R_5$, or $R_1$-$R_4$ in the preferred embodiment, are methyl. When $R_1$-$R_5$ are each independently methyl, preferably L is N and L' is N, C, S or O, then Y is preferably phenyl, biphenyl or substituted derivatives, or may be selected from a substitute or unsubstituted alkyl or alkenyl, such as an unsubstituted $C_2$-$C_{10}$ alkyl or alkenyl; or aryl such as a substituted or unsubstituted saturated or unsaturated cyclic or heterocyclic ring.

Y or $R_1$-$R_5$ when not H or methyl, are preferably a saturated or unsaturated cyclic or heterocyclic ring or rings, such as a phenyl or bi-phenyl ring structure The L-L' ligand, may comprise an unsaturated or saturated ring which is present as part of the chelating ligand and may be substituted with one or more groups or fused or otherwise substituted to one or more further unsaturated or saturated rings, which may or may not be heterocyclic.

For example and L-L' chelating ligand may have the following structure:

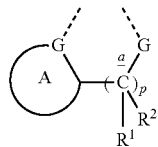

wherein, the ring A is a substituted or unsubstituted aromatic ring, optionally fused to one or more aromatic or saturated or unsaturated rings, and optionally includes one or more further heteroatoms in ring A or in the rings fused therewith;

G is independently O, N, C, S or P or GR', R" wherein R' ror R" is independently selected from the group consisting of hydrogen, branched or unbranched substituted or unsubstituted linear or cyclic alkyl, branched or unbranched substituted or unsubstituted linear or cyclic alkenyl, branched or unbranched substituted or unsubstituted linear or cyclic alkynyl or substituted or unsubstituted monocyclic or polycyclic aryl or heteroaryl;

$R^1$ and $R^2$ are independently selected at each occurrence from the group consisting of hydrogen, branched or unbranched substituted or unsubstituted linear or cyclic alkyl, branched or unbranched substituted or unsubstituted linear or cyclic alkenyl, branched or unbranched substituted or unsubstituted linear or cyclic alkynyl or substituted or unsubstituted monocyclic or polycyclic aryl or heteroaryl, carboxy, alkyloxycarbonyl hydroxyl, amino, nitro, alkyloxy, alkylthio, formyl, cyano, carbamoyl, halo (e.g. fluoro, chloro, bromo or iodo), —S(O)$NR^{12}R^{13}$ or —S(O)$R^{14}$, or together, independently at each occurrence, form the group =O or =S, or independently may combine with ring A to form a ring fused with ring A, such fused ring being saturated or unsaturated, substituted or unsubstituted with any of the above-listed groups, and optionally includes one or more further heteroatoms;

p is a number from 1 to 6;

the bond labelled a is a single bond when both $R^1$ and $R^2$ on the carbon adjacent G are present or a double bond when one of $R^1$ and $R^2$ on the carbon adjacent G is absent; and the dashed lines represent the bonds to the metal (III) atom, e.g. Ir(III).

In a preferred embodiment the L-L' chelating ligand may have the following structure:

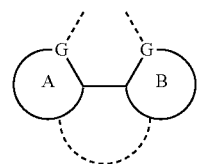

Wherein, G is as described above and the A and B can be same or different.

(for the same, e.g., bipy,

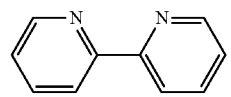 [SMILES: c1ccc(-c2ccccn2)nc1]

for the different, e.g., tpy

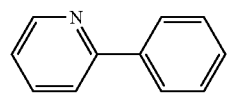 [SMILES: c1ccc(-c2ccccn2)cc1]

Alternatively the A and B ring can be fused together, e.g., phen

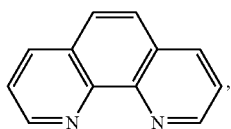 [SMILES: c1cnc2c(c1)ccc1cccnc12]

thus the dash line, when present, in the structure means A and B may be fused together, typically by way of a further unsaturated or saturated ring structure.

An alternative ligand is one or both of the G atoms are preferably part of a branched or unbranched, substituted or unsubstituted cyclic or straight chain aliphatic group, although aromatic rings are not excluded.

For example such alternative ligands may have the following structure:

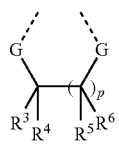

wherein $R^3$, $R^4$, $R^5$ and $R^6$ are independently selected at each occurrence from the group consisting of hydrogen, branched or unbranched substituted or unsubstituted linear or cyclic alkyl, branched or unbranched substituted or unsubstituted linear or cyclic alkenyl, branched or unbranched substituted or unsubstituted linear or cyclic alkynyl or substituted or unsubstituted monocyclic or polycyclic aryl or heteroaryl, carboxy, alkyloxycarbonyl hydroxyl, amino, nitro, alkyloxy, alkylthio, formyl, cyano, carbamoyl, halo (e.g. fluoro, chloro, bromo or iodo), —S(O)NR$^{12}$R$^{13}$ or —S(O)R$^{14}$, or together, independently at each occurrence, form the group =O or =S or independently may combine with one or both of the donor nitrogen atoms to form a nitrogen-containing substituted or unsubstituted aliphatic or aromatic ring; and G, p and the dashed lines have the same definitions as provided above.

Preferably, $R^3$, $R^4$, $R^5$ and $R^6$ are independently selected from hydrogen and alkyl, most preferably each is hydrogen.

Preferably p is 1.

Examples of preferred L-L' ligands are shown in Chart 1, disclosed hereinafter.

It will be appreciated that the ligand structure may be different when part of the metal complex as compared to the free ligand when not complexed. Thus, the ligand prior to being complexed may be termed a ligand precursor. For example, one or more hydrogens may be lost from a free ligand molecule to enable bonding to the metal atom to form the metal complex. As an example, picolinic acid, in the free state has the following structure:

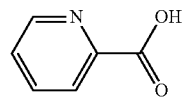

whereas when complexed to the metal, has the de-protonated structure:

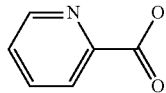

It will be appreciated that the complexed ligands may have a negative charge, which may be delocalised between the donor atoms, as will be understood by the skilled addressee according to known general principles.

The present invention also extends to compounds in which the Y, $R_1$ $R_2$, $R_3$, or $R_4$ group may be tethered to the ligand moiety. The tether may be attached to the ligand at any position, including for example substituents or ring groups on the ligand.

For example, in an N, O-ligand having the structure shown above, the tether may be attached to a carbon atom of the ring A or to any of the $R^1$ or $R^2$ groups.

Tethers may also be used to provide dinuclear and polynuclear complexes in which at least one metal is Ir(III), or Rh(III).

In such dinuclear and polynuclear complexes, the tethers may bridge between each of the complexes in any of a number of independent ways. For example, the tether may form a linkage between any one of Y, $R_1$-$R_4$, chelating atom (L or L'), chelating backbone ( - - - ) or directly from the metal in a first complex molecule to any one of those same positions in a second complex molecule, which is thereby joined or tethered to the first molecule.

Di- or polynuclear complexes containing both Ir(III) and Rh(III) may be advantageous due to the differing properties and reactivities of the respective tethered Ir(III) and Rh(III) complexes.

A tether may be represented by the group -${\{n\}}_x$-, and examples of tethered dinuclear complexes include the following structures, in which $M_1$ and $M_2$ are both Ir(III), or $M_1$ is Ir(III) and $M_2$ is Rh(III) or vice versa:

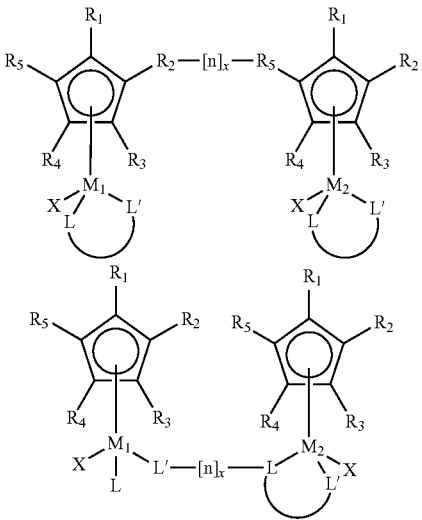

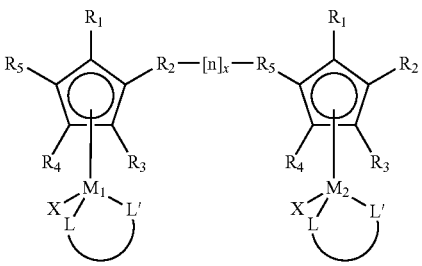

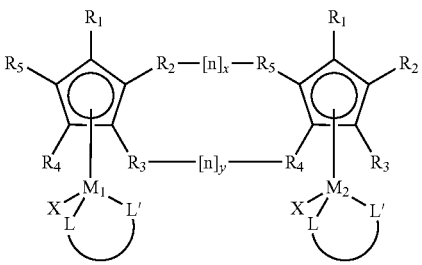

-continued

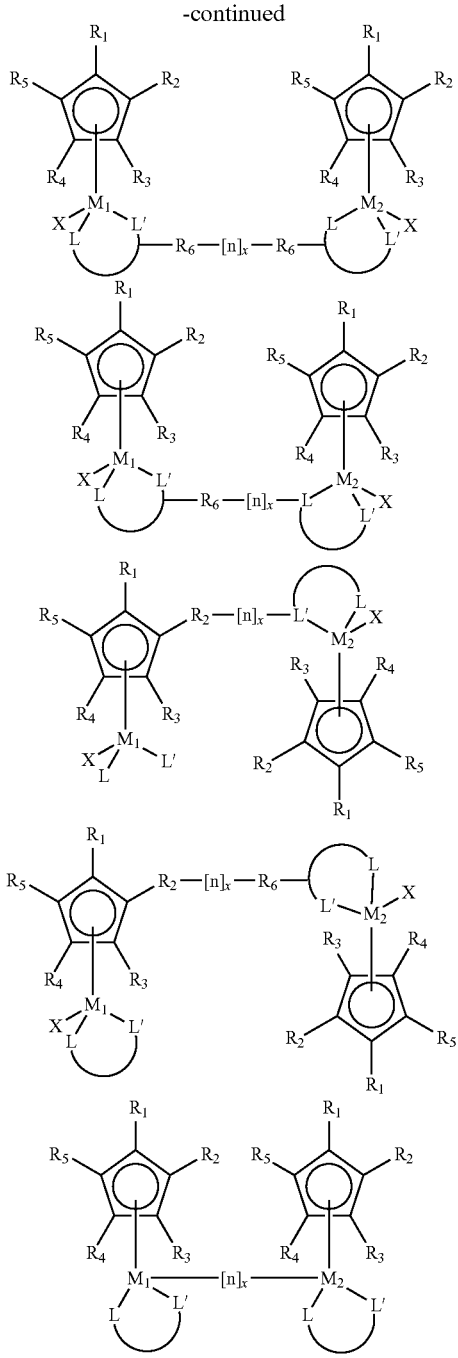

(n) may represent a CH$_2$, aryl such as an aromatic group, NH$_2$, SiO$_2$, amino acid, or other suitable linking group and x may be 1-20, for example.

The tethers may be selected from any suitable group to provide a link between the respective desired groups of the complexes to be joined.

Typical tethers may be selected from alkylene, alkenylene, alkynylene, aromatic-containing groups, wherein the aromatic groups may optionally contain heteroatoms; and heteroatom-containing groups such as peptide and ether linkages.

The group X in the compounds according to formula (I) may be selected from the halogens i.e. fluoro, chloro, bromo or iodo. Alternatively, the group X may be selected from any suitable donor ligand, examples of which are ligands wherein the donor atom thereof is selected from the group consisting of nitrogen, oxygen, sulphur or phosphorous.

Typically, such ligand groups may be selected from pyridine (and derivatives thereof), water, hydroxo (i.e. OH$^−$), azides, sulfonates or pseudohalogens and the like.

The group X may also be selected from nucleo-bases or derivatives thereof, e.g. a pyrimidine or purine, for example thymine, cytosine, adenine, guanine or uracil. Preferred examples include 9-ethylguanine and 9-ethyladenine.

The group X may be replaced by other groups when the compounds described herein are presented in a biological environment, for example, the species wherein X is water or hydroxo may be formed in a biological environment.

The ion, Q in a compound according to formula (I), acts as a counter ion to the complex and balances the charges in the complex to generally provide a molecular species with overall charge of zero.

Negatively charged counter ions may be any suitable ion, for example selected from BF$_4$, BPh$_4$, PF$_6$, triflate and halides.

Positively charged counter ions may be any suitable ion, for example alkali metal cations such as Na$^+$ and K$^+$, or alkaline earth metal cations such as Mg$^{2+}$ and Ca$^{2+}$. Positive counter ions may also include organic cations, other metal complexes, protonated heterocyclic compounds and substituted or unsubstituted ammonium ions, i.e. NH$_4^+$.

The counter ion may be chosen for certain purposes, for example, non-nucleophilic anions may be preferred, such as BPh$_4$ which tends to provide an insoluble complex thereby providing a useful advantage during a recovery stage of the compound preparation, e.g. for separation out of a solution or liquid medium. PF$_6$ may have a similar effect by providing a complex which is more soluble than a corresponding complex with BPh$_4$ counter ion, whilst remaining less soluble than a corresponding complex with chloride as the counter ion. These counter ions are not, however, necessarily excluded from the compound in its final useable form.

The counter ions may be chosen to provide a useful solubility for preparation of the complexes and the same counter ion may be retained or exchanged for another counter ion to provide a compound better suited for pharmaceutical/medical uses.

For example, triflate may be selected, or chloride, bromide or iodide to provide more easily soluble compounds.

Physiologically functional derivatives of compounds of the present invention are derivatives which can be converted in the body into the parent compound. Such physiologically functional derivatives may also be referred to as "pro-drugs" or "bioprecursors". Physiologically functional derivatives of compounds of the present invention include in vivo hydrolysable esters. Additionally, the compounds of the present invention, may themselves, be considered as pro-drugs, which are converted into a physiologically active form in the body. Examples are the water (or aqua) complexes, i.e. where X is H$_2$O, which, without wishing to be bound by theory, are thought to be the active species in the biological environment.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds recited herein, as well as wholly or partially racemic mixtures of such enantiomers.

The compounds of the present invention may be prepared using reagents and techniques readily available in the art and as described hereinafter. Novel intermediate compounds in the synthetic route for preparation of the compounds of the present invention may be important molecules for general application for the preparation of the molecules of the present invention. Accordingly, the present invention extends to include those novel intermediate compounds.

According to a second aspect of the present invention there is provided a pharmaceutical composition comprising a compound according to the first aspect or preferred embodiments, together with a pharmaceutically acceptable carrier therefor.

The present invention, in a third aspect, provides a compound according to the first aspect or preferred embodiments for use in medicine.

In a fourth aspect, the present invention provides the use of a compound according to the first aspect or preferred embodiments, for the preparation of a medicament for the treatment or prophylaxis of a disease involving abnormal cell proliferation, in particular cancer.

In a fifth aspect, the present invention provides a method of treatment or prophylaxis of a disease involving cell proliferation, in particular cancer, said method comprising administering a therapeutically or prophylactically useful amount of a compound according to the first aspect or preferred embodiments, to a subject in need thereof.

The present invention also extends to the methods of preparing the compounds described herein. Generally, the method comprises providing a compound of formula $[CpZX_2]_2$ in a first step and then reacting the compound with a ligand L-L' in a second step to provide a compound according to formula (I).

The groups L-L', X and Z have the same meaning as hereinbefore recited and Cp refers to the substituted cyclopentadine moieties as described previously.

Preferably, in the preparation X in the starting material is halo, such as chloro.

During the preparation, a step may be included to exchange the counter ion of the complex for a different preferred counter ion.

Preferred preparation conditions comprise
i) providing and dissolving the compound $[CpZX_2]_2$ with the ligand/ligand precursor in an alcoholic solvent, such as methanol, which may include an amount of water, optionally heating or refluxing the solution with or without stirring and for an amount of time as may be determined by the skilled addressee;
ii) introducing a suitable compound to the resultant mixture to add a preferred counter ion to the formed complex.

For example, a suitable compound for introducing the counter ion $PF_6$, is $NH_4PF_6$.

As indicated above, the present invention provides a treatment or prophylaxis of a disease, pathology or condition recited herein comprising administering a compound recited herein to a patient in need thereof.

Diseases involving abnormal proliferation of cells are treatable with the compounds recited herein. Examples of such diseases include cancers and hyperproliferation disorders.

Examples of cancers which may be treated by the active compounds include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

Preferred cancers include leukaemia, CNS cancer, melanoma, prostrate cancer, colon cancer, breast cancer or any selection thereof.

Examples of other therapeutic agents that may be administered together (whether concurrently or at different time intervals) with the compounds of the formula (I) include but are not limited to topoisomerase inhibitors, alkylating agents, antimetabolites, DNA binders and microtubule inhibitors (tubulin target agents), such as cisplatin, cyclophosphamide, doxorubicin, irinotecan, fludarabine, 5FU, taxanes, mitomycin C; L-buthionine-sulfoximine (L-BSO) or radiotherapy. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where the compound of the formula (I) is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

The patient is typically an animal, e.g., a mammal, especially a human.

For use according to the present invention, the compounds or physiologically acceptable salt, ester or other physiologically functional derivative thereof described herein may be presented as a pharmaceutical formulation, comprising the compound or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Advantageously, solutions may be prepared and stored in a ready to use condition, (e.g. without the need for further formulation such as dilution into a useable concentration), in light-excluding containers such as sealed bottles, ampoules, blister packages and the like. Such containers are preferably provided in a sterile condition.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The present invention will now be described by way of example and with reference to the drawings.

DETAILED DESCRIPTION

Experimental Section

Figure 1:
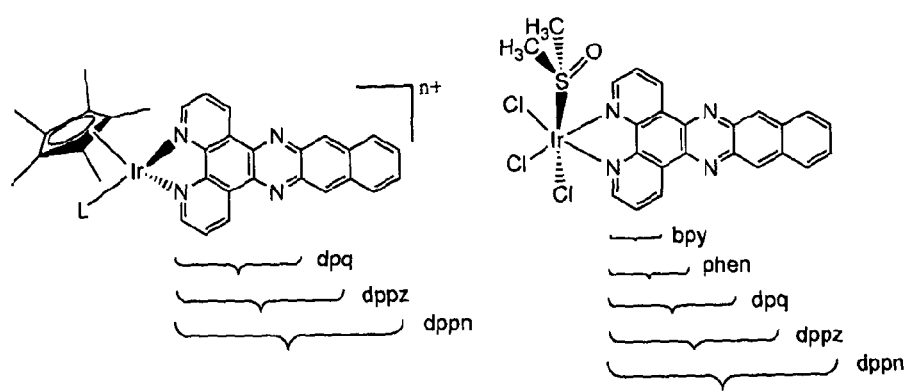
FIG. 1. shows the structure of some iridium complexes used in Sheldrick's group.

Materials. $IrCl_3 \cdot nH_2O$, 2,3,4,5-tetramethyl-2-cyclopentenone (95%), 1,2,3,4,5-penta methyl-cyclopentadiene (95%), butyllithium solution (1.6 M in hexane), lithium wire (99.9%), 9-ethylguanine, 9-ethyladenine, 2,2'-bipyridine-3,3'-diol, 4,4'-bimethyl-2,2'-dipyridyl and 2-phenylpyridine were purchased from Sigma-Aldrich. $[(\eta^5-C_5Me_5) IrCl_2]_2$ (ZLd1),[1] $[(\eta^5-C_5Me_5)Ir(bipy)Cl]Cl$ (ZL04Cl),[8] $[(\eta^5-C_5Me_5)Ir(phen)Cl]Cl$ (ZL07Cl),[8] $[(\eta^5Me_5)Ir(\eta^5H_4N-2CO_2)Cl]$ (ZL03),[9] $C_5Me_4HPh$,[10] $[(\eta^5-C_5Me_4)Ir(2-phpy)Cl]$ (ZL47),[11] and $[(\eta^5-C_5Me_5)Ir\{C_6H_4-2-C(H)=NPh-\kappa C,N\}Cl]$ (ZL51),[12] were prepared according to literature methods. Methanol was distilled over magnesium/iodine prior to use.

Preparation of $[(\eta^5-C_5Me_5)IrCl(H_2NCH_2CH_2NH_2-N,N)]PF_6$ (ZL01PF$_6$). $[(\eta^5-C_5Me_5)Ir Cl_2]_2$ (50 mg, 0.0627 mmol) was suspended in dry methanol (15 ml), and ethylenediamine (9.4 mg, 0.157 mmol) was added in one portion. The mixture was stirred for 1 h at ambient temperature and filtered. The volume of solvent was slowly reduced to half on a rotary evaporator and $NH_4PF_6$ (102.2 mg, 0.627 mmol) was added. After standing at 277 K, a microcrystalline product was formed. This was collected by filtration, washed with diethyl ether, and recrystallized from methanol/diethyl ether. Yield: 39.9 mg (56%). Anal. Calcd for $C_{12}H_{23}ClF_6IrN_2P$ (568.08): C, 25.38; H, 4.08; N, 4.93. Found: C, 25.07; H, 3.89; N, 4.99. $^1$H NMR (DMSO-d$_6$): δ=5.70 (b, 2H), 4.86 (b, 2H), 2.54 (b, 2H), 2.28 (b, 2H), 1.68 (s, 15H).

$[(\eta^5-C_5Me_5)Ir(acac)Cl]$ (ZL02) $[(\eta^5-C_5Me_5)IrCl_2]_2$ (50 mg, 0.0627 mmol) was suspended in acetone (15 ml), and sodium acetylacetonate monohydrate (17.6 mg, 0.125 mmol) was added. The mixture was stirred for 1 h at ambient temperature and filtered. The solvent was removed in vacuo by using a rotary evaporator, and the product extracted with $CH_2Cl_2$ (10 ml). The solvent was removed again in vacuo. The final product was recrystallized from acetone/light petroleum ether in a freezer at 253 K overnight. Yield: 21 mg (36%). Anal. Calcd for $C_{15}H_{22}ClIrO_2$ (462.00): C, 39.00; H, 4.80. Found: C, 39.35; H, 4.69. $^1$H NMR (CDCl$_3$): δ=5.20 (s, 1H), 1.93 (s, 6H), 1.59 (s, 15H). Crystals of ZL02 suitable for X-ray diffraction were obtained by evaporation of a acetone/light petroleum ether solution at ambient temperature.

$[(\eta^5-C_5Me_4C_6H_5)IrCl_2]_2$ (ZLd2). A solution of $C_5Me_4HPh$ (1.7 g, 8.5 mmol) and $IrCl_3$ (1.7 g, 5.7 mmol) in Meal (60 ml) was heated under refluxed in $N_2$ atmosphere for 48 h. The reaction mixture was allowed to cool to room temperature and the dark green precipitate was filtered off in air. The volume of the dark red filtrate was reduced in volume to ca. 30 ml on a rotary evaporator to give more products that were combined with the first crop and washed with methanol and diethyl ether and dried in air. Yield: 1.02 g (39%). $^1$H NMR (CDCl$_3$): δ=7.58 (m, 2H), 7.35 (m, 3H), 1.72 (s, 6H), 1.63 (s, 6H). Crystals of the dimer suitable for X-ray diffraction were obtained by evaporation of a chloroform/hexane solution at ambient temperature.

$[(\eta^5-C_5Me_4C_6H_5)IrCl(H_2NCH_2CH_2NH_2-N,N)]BPh_4$ (ZL31BPh$_4$). The synthesis was performed in the same manner as for ZL01PF$_6$, using $[(\eta^5-C_5Me_4C_6H_5)IrCl_2]_2$ instead of $[(\eta^5-C_5Me_5)IrCl_2]_2$ and $NH_4BPh_4$ instead of $NH_4PF_6$. Yield: 19.9 mg (23%). Anal. Calcd for $C_{41}H_{45}BClIrN_2$ (804.29): C, 61.15; H, 5.76; N, 3.48. Found: C, 61.76; H, 5.89; N, 3.39. $^1$H NMR (DMSO-d$_6$): δ=7.38 (m, 2H), 7.33 (m, 3H), 7.24 (b, 8H), 6.89 (t, 8H, J=7.3 Hz), 6.75 (t, 4H, J=7.3 Hz), 5.75 (b, 2H), 4.64 (b, 2H), 2.64 (b, 2H), 2.35 (b, 2H), 1.77 (s, 6H), 1.65 (s, 6H). Crystals of ZL31BPh$_4$ suitable for X-ray diffraction were obtained by slow evaporation of a methanol/diethyl ether solution at ambient temperature.

$[(\eta^5-C_5Me_4C_6H_5)Ir(\eta^2-C_5H_4N-2-CO_2)Cl]$ (ZL38). A solution of $[(\eta^5-C_5Me_4C_6H_5)IrCl_2]_2$ (50 mg, 0.054 mmol), picolinic acid (16.7 mg, 0.136 mmol) and sodium methoxide (7.3 mg, 0.136 mmol) in MeOH (50 ml) was heated under refluxed in $N_2$ atmosphere for 3 h and filtered. The solvent was removed in vacuo, the product extracted with $CH_2Cl_2$ (10 ml), and the volume was reduced to ca. 0.5 ml on a rotary evaporator. A yellow precipitate formed after addition of diethyl ether and storage at 253 K which was collected by filtration, washed with diethyl ether and dried in air. Yield: 25.4 mg (43%). $^1$H NMR (DMSO-d$_6$): δ=8.65 (d, 1H, J=4.5 Hz), 8.15 (t, 1H, J=8.3 Hz), 7.93 (d, 1H, J=7.8 Hz), 7.81 (t, 1H, J=7.0 Hz), 7.52 (m, 5H), 1.74 (s, 6H), 1.64 (s, 6H). Anal. Calcd for $C_{21}H_{21}ClNO_2Ir$ (547.09): C, 46.10; H, 3.87; N, 2.56. Found: C, 45.89; H, 3.65; N, 2.73. Crystals of ZL38 suitable for X-ray diffraction were obtained by slow evaporation of a methanol/diethyl ether solution at ambient temperature.

$[(\eta^5-C_5Me_4C_6H_5)Ir(bipy)Cl]PF_6$ (ZL37PF$_6$). A solution of $[(\eta^5-C_5Me_4C_6H_5)IrCl_2]_2$ (50 mg, 0.054 mmol), 2,2'-bipyridine (21.2 mg, 0.136 mmol) in MeOH (40 ml) was heated under refluxed in $N_2$ atmosphere for 16 h and filtered. The volume was slowly reduced to half on a rotary evaporator and $NH_4PF_6$ (45 mg, 0.276 mmol) was added. After standing at 277 K, the mixture formed a microcrystalline product. This was collected by filtration, washed with diethyl ether, and recrystallized from methanol/diethyl ether. Yield: 57 mg (73%). $^1$H NMR (DMSO-d$_6$): δ=8.84 (d, 2H, J=8.2 Hz), 8.71 (d, 2H, J=5.4 Hz), 8.35 (t, 2H, J=7.5 Hz), 7.81 (t, 2H, J=7.5 Hz), 7.50 (m, 5H), 1.77 (s, 6H), 1.67 (s, 6H). Anal. Calcd for $C_{25}H_{25}ClN_2IrPF_6$ (726.10): C, 41.35; H, 3.47; N, 3.86. Found: C, 40.85; H, 3.35; N, 3.83. Crystals of ZL37PF$_6$ suitable for X-ray diffraction were obtained by slow evaporation of a methanol/diethyl ether solution at ambient temperature.

$[(\eta^5-C_5Me_4C_6H_5)Ir(phen)Cl]PF_6$ (ZL33PF$_6$). A solution of $[(\eta^5C_5Me_4C_6H_5)IrCl_2]_2$ (45 mg, 0.049 mmol), 1,10-phenanthroline monohydrate (24.3 mg, 0.123 mmol) in MeOH (40 ml) was heated under refluxed in $N_2$ atmosphere for 10 h and filtered. The volume was slowly reduced to half on a rotary evaporator and $NH_4PF_6$ (45 mg, 0.276 mmol) was added. After standing at 277K, a microcrystalline product formed. This was collected by filtration, washed with diethyl ether, and recrystallized from methanol/diethyl ether. Yield: 27 mg (37%). $^1$H NMR (DMSO-d$_6$): δ=9.08 (d, 2H, J=5.3 Hz), 8.99 (d, 2H, J=8.5 Hz), 8.39 (s, 2H), 8.19 (q, 2H, J=8.3 Hz), 7.56 (m, 5H), 1.84 (s, 6H), 1.73 (s, 6H). Anal. Calcd for $C_{27}H_{25}ClN_2IrPF_6$ (750.16): C, 43.23; H, 3.36; N, 3.73. Found: C, 43.01; H, 3.31; N, 3.86. Crystals of ZL33PF$_6$ suitable for X-ray diffraction were obtained by slow evaporation of a methanol/diethyl ether solution at ambient temperature.

$C_5Me_4HPh_2$. A solution of 4-bromobiphenyl (5.7 g, 24.5 mmol) in 100 ml of THF was treated with n-BuLi/hexane solution (15.3 ml, 24.5 mmol) at 195K, After stirring at this temperature for 3 h, 4.06 g (29.4 mmol) of 2,3,4,5-tetraethyl-2-cyclopentenone was added. The reaction mixture was allowed to slowly warm to room temperature with stirring overnight. The resulting yellow solution was acidified with HCl. The organic portion was separated and the aqueous layer was further extracted with diethyl ether (50 ml). The combined organic portions were dried over with anhydrous $MgSO_4$, filtered, and the solvents evaporated to dryness to afford a light yellow product. Yield: 2.7 g (40%). $^1$H NMR (CDCl$_3$): δ=7.64 (m, 4H), 7.44 (m, 2H), 7.33 (m, 3H), 3.25 (m, 1H), 2.08 (s, 3H), 1.95 (s, 3H), 1.88 (s, 3H), 1.00 (d, 3H, J=7.5 Hz).

[(η$^5$-C$_6$Me$_4$C$_6$H$_4$C$_6$H$_5$)IrCl$_2$]$_2$ (ZLd3). The synthesis was performed as for ZLd2 using C$_5$Me$_4$HPhPh (2.7 g, 9.9 mmol) and IrCl$_3$·xH$_2$O (2.95 g, 9.9 mmol). Yield: 1.7 g (32%). $^1$H NMR (DMSO-d$_6$): δ=7.70 (m, 4H), 7.46 (m, 2H), 7.35 (m, 3H), 2.02 (s, 3H), 1.91 (s, 3H), 1.84 (s, 3H), 0.90 (d, 3H, J=7.3 Hz).

[(η$^5$-C$_6$Me$_4$C$_6$H$_4$C$_6$H$_5$)Ir(bipy)Cl]PF$_6$ (ZL25PF$_6$). The synthesis was performed as for ZL37PF$_6$ using [(η$^5$-C$_6$Me$_4$C$_6$H$_4$C$_6$H$_5$)IrCl$_2$]$_2$ (50 mg, 0.046 mmol), 2,2'-bipyridine (18.0 mg, 0.115 mmol). Yield: 43 mg (58%). $^1$H NMR (DMSO-d$_6$): δ=8.81 (d, 2H, J=8.0 Hz), 8.74 (d, 2H, J=6.0 Hz), 8.35 (t, 2H, J=7.8 Hz), 7.82 (t, 4H, J=7.5 Hz), 7.75 (d, 2H, J=8.0 Hz), 7.60 (d, 2H, J=8.0 Hz), 7.50 (t, 2H, J=7.8 Hz), 7.42 (t, 2H, J=7.3 Hz), 1.78 (s, 6H), 1.72 (s, 6H). Anal. Calcd for C$_{31}$H$_{29}$ClF$_6$IrN$_2$P (802.21): C, 46.41; H, 3.64; N, 3.49. Found: C, 45.85; H, 3.55; N, 3.63. Crystals of ZL25PF$_6$ suitable for X-ray diffraction were obtained by slow evaporation of a methanol/diethyl ether solution at ambient temperature.

[(η$^5$-C$_5$Me$_4$C$_6$H$_4$C$_6$H$_5$)Ir(phen)Cl]PF$_6$(ZL54PF$_6$). The synthesis was performed as for ZL33PF$_6$ using [(η$^5$-C$_6$Me$_4$C$_6$H$_4$C$_6$H$_5$)IrCl$_2$]$_2$ (50 mg, 0.046 mmol), 1,10-phenanthroline monohydrate (18.5 mg, 0.093 mmol). Yield: 15 mg (23%). $^1$H NMR (CDCl$_3$): δ=9.16 (d, 2H, J=5.5 Hz), 8.78 (d, 2H, J=8.3 Hz), 8.22 (s, 2H), 8.17 (q, 2H, J=8.3 Hz), 7.76 (d, 2H, J=8.3 Hz), 7.60 (d, 2H, J=7.5 Hz), 7.45 (d, 2H, J=8.3 Hz), 7.52 (t, 2H, J=7.3 Hz), 7.44 (t, 1H, J=7.3 Hz), 2.05 (s, 6H), 1.85 (s, 6H). Anal. Calcd for C$_{33}$H$_{29}$Cl$_2$N$_2$Ir (716.13): C, 55.30; H, 4.08; N, 3.91. Found: C, 55.61; H, 3.91; N, 3.88.

[(η$^5$-C$_5$Me$_4$C$_6$H$_4$C$_6$H$_5$)Ir(η$^2$-C$_6$H$_4$N-2-CO$_2$)Cl] (ZL43). The synthesis was performed as for ZL38 using [(η$^5$-C$_5$Me$_4$C$_6$H$_4$C$_6$H$_5$)IrCl$_2$]$_2$ (50 mg, 0.046 mmol), picolinic acid (12.3 mg, 0.10 mmol) and sodium methoxide (5.4 mg, 0.10 mmol). Yield: 22 mg (37%). $^1$H NMR (DMSO-d$_6$): δ=8.70 (d, 1H, J=5.7 Hz), 8.16 (t, 1H, J=7.8 Hz), 7.97 (d, 1H, J=8.0 Hz), 7.77 (t, 1H, J=6.5 Hz), 7.72 (m, 4H), 7.64 (d, 2H, J=8.3 Hz), 7.48 (t, 2H, J=7.3 Hz), 7.39 (t, 1H, J=7.3 Hz), 1.74 (d, 6H, J=7.3 Hz), 1.69 (s, 3H), 1.65 (s, 3H). Anal. Calcd for C$_{28}$H$_{27}$ClNO$_2$Ir (547.09): C, 52.78; H, 4.27; N, 2.20. Found: C, 52.09; H, 4.15; N, 2.33.

[(η$^5$-C$_5$Me$_5$)Ir(biPy(OH)O)Cl] (ZL44). To a suspension of [(η$^5$-C$_5$Me$_5$)IrCl$_2$]$_2$ (50 mg, 0.0627 mmol) in dry, freshly distilled methanol (25 ml), 2,2'-bipyridine-3,3'-diol (24.5 mg, 0.13 mmol) was added. The reaction mixture was stirred at ambient temperature under argon overnight, filtered and the volume was reduced until the onset of precipitation. It was kept at 277 K for 24 h to allow further precipitation to occur. The fine yellow solid was collected by filtration, washed with methanol followed by ether, and dried in vacuum. It was recrystallized from methanol/ether. Yield: 17.6 mg (51.0%). $^1$H NMR (DMSO-d$_6$): δ=8.06 (d, 2H, J=5.3 Hz), 7.28 (dd, 2H, J=8.3 Hz), 7.06 (d, 2H, J=8.3 Hz), 1.54 (s, 15H). Anal. Calcd for C$_{20}$H$_{22}$ClN$_2$O$_2$Ir (550.07): C, 43.67; H, 4.03; N, 5.09. Found: C, 42.99; H, 4.15; N, 5.33. Crystals of ZL44 suitable for X-ray diffraction were obtained by evaporation of a methanol/diethyl ether solution at ambient temperature.

[(η$^5$-C$_5$Me$_4$C$_6$H$_5$)Ir(bipy(OH)$_2$)Cl]PF$_6$ (ZL45). To a suspension of [(η$^5$-C$_5$Me$_4$C$_6$H$_5$)IrCl$_2$]$_2$ (45 mg, 0.049 mmol), in dry, freshly distilled methanol (10 ml), 2,2'-bipyridine-3,3'-diol (18.8 mg, 0.10 mmol) dissolved in methanol (20 ml) was added dropwise. The reaction mixture was left stirring at ambient temperature for 1 h. It was then filtered, and to the filtrate, NH$_4$PF$_6$ (82 mg, 0.50 mmol) was added and the flask shaken. A precipitate started to appear almost immediately. The flask was kept at 253 K overnight. The solid obtained was collected by filtration, washed with cold methanol and ether and dried in air to give a bright yellow solid. Yield: 34 mg (46%). $^1$H NMR (CDCl$_3$): δ=7.81 (d, 2H, J=5.5 Hz), 7.46 (m, 5H), 7.15 (d, 2H, J=8.5 Hz), 6.99 (dd, 2H, J=8.5 Hz), 1.64 (s, 12H). Anal. Calcd for C$_{26}$H$_{26}$ClN$_2$O$_2$IrPF$_6$ (758.11): C, 39.61; H, 3.32; N, 3.70. Found: C, 40.25; H, 3.29; N, 4.03.

{(η$^5$-C$_5$Me$_4$C$_6$H$_4$C$_6$H$_5$)Ir[bipy(OH)(O)]Cl} (ZL46). The synthesis was performed as for ZL44 using [(η$^5$-C$_6$Me$_4$C$_6$H$_4$C$_6$H$_5$)IrCl$_2$]$_2$ (50 mg, 0.046 mmol), 2,2'-bipyridine-3,3'-diol (17.8 mg, 0.095 mmol). Yield: 30.7 mg (47%). $^1$H NMR (MeOD-d$_4$): δ=8.08 (d, 2H, J=7.3 Hz), 7.73 (d, 2H, J=7.3 Hz), 7.68 (d, 2H, J=7.9 Hz), 7.59 (d, 2H, J=7.9 Hz), 7.47 (t, 2H, J=7.3 Hz), 7.41 (t, 1H, J=7.9 Hz), 7.20 (m, 4H), 1.73 (s, 6H), 1.69 (s, 6H). Anal. Calcd for C$_{31}$H$_{29}$ClN$_2$O$_2$Ir (688.20): C, 54.1; H, 4.1; N, 4.07. Found: C, 53.99; H, 4.25; N, 3.98. Crystals of ZL46 suitable for X-ray diffraction were obtained by slow evaporation of a methanol/diethyl ether solution at ambient temperature.

[(η$^5$-C$_5$Me$_4$C$_6$H$_4$C$_6$H$_5$)Ir(2-phpy)Cl] (ZL49). A mixture of [(η$^5$-C$_5$Me$_4$C$_6$H$_4$C$_6$H$_5$)IrCl$_2$]$_2$ (50 mg, 0.046 mmol), 2-phenylpyridine (14.7 mg, 0.095 mmol), and sodium acetate (16.4 mg, 0.2 mmol) in CH$_2$Cl$_2$ (5 ml) was stirred for 24 h at room temperature. The solution was filtered through celite and rotary evaporated to dryness. The product was crystallized from CH$_2$Cl$_2$/hexane. Yield: 22 mg (37%). $^1$H NMR (CDCl$_3$): δ=8.51 (d, 1H, J=5.3 Hz), 7.81 (d, 1H, J=7.3 Hz), 7.72 (m, 2H), 7.64 (m, 5H), 7.51 (m, 4H), 7.37 (d, 1H, J=7.6 Hz), 7.16 (d, 1H, J=7.3 Hz), 7.05 (dd, 1H, J=6.0 Hz), 6.94 (d, 1H, J=7.3 Hz), 1.82 (m, 9H), 1.59 (s, 3H). Anal. Calcd for C$_{32}$H$_{29}$ClNIr (655.25): C, 58.66; H, 4.46; N, 2.14. Found: C, 58.06; H, 4.25; N, 2.18. Crystals of ZL49 suitable for X-ray diffraction were obtained by slow evaporation of a methanol/diethyl ether solution at ambient temperature.

[(η$^5$-C$_5$Me$_6$)Ir(bipy(Me)$_2$)Cl]PF$_6$ (ZL55PF$_6$). The synthesis was performed as for ZL33PF$_6$ using [(η$^5$-C$_6$Me$_6$)IrCl$_2$]$_2$ (50 mg, 0.0627 mmol), 4,4'-bimethyl-2,2'-dipyridyl (24.0 mg, 0.13 mmol). Yield: 58 mg (67%). $^1$H NMR (DMSO-d$_6$): δ=8.8 (d, 2H, J=5.7 Hz), 8.78 (s, 2H), 7.68 (d, 2H, J=5.7 Hz), 2.62 (s, 6H), 1.64 (s, 15H). Anal. Calcd for C$_{22}$H$_{27}$ClN$_2$IrPF$_6$ (688.20): C, 38.18; H, 3.93; N, 4.05. Found: C, 38.24; H, 3.95; N, 3.98.

[(η$^5$-C$_5$Me$_4$C$_6$H$_5$)Ir(bipy(Me)$_2$)Cl]PF$_6$ (ZL57PF$_6$). The synthesis was performed as for ZL33PF$_6$ using [(η$^5$-C$_6$Me$_4$C$_6$H$_5$)IrCl$_2$]$_2$ (50 mg, 0.054 mmol), 4,4'-bimethyl-2,2'-dipyridyl (20.2 mg, 0.11 mmol). Yield: 48.7 mg (60%). $^1$H NMR (DMSO-d$_6$): δ=8.66 (s, 2H), 8.51 (d, 2H, J=5.7 Hz), 7.62 (d, 2H, J=5.7 Hz), 7.46 (m, 5H), 2.60 (s, 6H), 1.76 (s, 6H), 1.66 (s, 6H). Anal. Calcd for C$_{27}$H$_{29}$ClN$_2$IrPF$_6$ (754.17): C, 43.00; H, 3.88; N, 3.71. Found: C, 43.21; H, 3.95; N, 3.68. Crystals of ZL57PF$_6$ suitable for X-ray diffraction were obtained by slow evaporation of a methanol/diethyl ether solution at ambient temperature.

[(η$^5$-C$_5$Me$_4$C$_6$H$_4$C$_6$H$_5$)Ir(bipy(Me)$_2$)Cl]PF$_6$(ZL59PF$_6$). The synthesis was performed as for ZL33PF$_6$ using [(η$^5$-C$_5$Me$_4$C$_6$H$_4$C$_6$H$_5$)IrCl$_2$]$_2$ (50 mg, 0.046 mmol), 4,4'-bimethyl-2,2'-dipyridyl (17.5 mg, 0.095 mmol). Yield: 39 mg (51%). $^1$H NMR (DMSO-d$_6$): δ=8.67 (s, 2H), 8.31 (d, 2H, J=6.0 Hz), 7.79 (d, 2H, J=8.5 Hz), 7.75 (d, 2H, J=6.5 Hz), 7.65 (d, 2H, J=5.7 Hz), 7.57 (d, 2H, J=8.3 Hz), 7.50 (t, 2H, J=7.8 Hz), 7.42 (t, 2H, J=7.6 Hz), 2.60 (s, 6H), 1.77 (s, 6H), 1.71 (s, 6H). Anal. Calcd for C$_{33}$H$_{33}$ClN$_2$IrPF$_6$ (830.26): C, 47.74; H, 4.01; N, 3.37. Found: C, 47.26; H, 4.03; N, 3.43.

Methods and instrumentation: X-ray crystallography. All diffraction data were collected by Dr. Guy Clarkson (University of Warwick, department of chemistry) using an Oxford Diffraction Gemini four-circle system with a Ruby CCD area detector. All crystals were held with an Oxford Cryosystems low-temperature device operating at 100K. Absorption corrections for all data sets were performed by Semi-empirical from equivalents; structures were solved by direct methods using SHELXS (Sheldrick 1990) with additional light atoms found by Fourier methods; complexes were refined against $F^2$ using SHELXL[13], and Hydrogen atoms were added at calculated positions.

NMR Spectroscopy. $^1$H NMR spectra were acquired in 5 mm NMR tubes at 298K (unless stated otherwise) on either a Bruker DPX 400 ($^1$H=400.03 MHz) or AVA 600 ($^1$H=600.13 MHz) spectrometer. $^1$H NMR chemical shifts were internally referenced to $(CHD_2)(CD_3)SO$ (2.50 ppm) for DMSO-$d_6$, $CHCl_3$ (7.26 ppm) for chloroform-d, and to 1,4-dioxane (3.75 ppm) for aqueous solutions. All data processing was carried out using XWIN-NMR version 3.6 (Bruker U.K. Ltd.).

Mass Spectrometry. Electrospray ionization mass spectra (ESI-MS) were obtained on a Micromass Platform II Mass Spectrometer using $D_2O/H_2O$ or methanol solutions. The capillary voltage was 3.5 V and the cone voltage was varied between 20 and 45 V depending on sensitivity. The source temperature was 353 K. Mass spectra were recorded with a scan range m/z 50 to 1000 for positive ions. Data acquisition was performed on a Mass Lynx (V 2.5) Windows NT PC data system.

pH* Measurement. pH* values (pH meter reading without correction for effects of D on glass electrode) of NMR samples in $D_2O$ were measured at ca. 298 K directly in the NMR tube, before and after recording NMR spectra, using a Corning 240 pH meter equipped with a micro combination electrode calibrated with Aldrich buffer solutions of pH 4, 7 and 10. For determination of the $pK_a$* value of aquated complexes, complexes were dissolved in $D_2O$ and 0.98 mol equiv of $AgNO_3$ was added. The solution was stirred for 24 h at 298 K, and AgCl was removed by filtration.

Kinetics for Hydrolysis. Although complexes ZL01-ZL04, ZL07, ZL38 and ZL43 hydrolyzed too rapidly to monitor by $^1$H NMR, The kinetics of hydrolysis for complexes ZL25, ZL33, ZL37 and ZL54 were followed by $^1$H NMR at different temperatures. For this, solutions of the complexes with a final concentration of 0.2 mM in 5% MeOD-$d_4$/95% $D_2O$ (v/v) were prepared by dissolution of the complexes in MeOD-$d_4$ followed by rapid dilution using $D_2O$ with a pH* of about 3 (acidified with $HClO_4$), so that the aqua ligand was not deprotonated. $^1$H NMR spectra were taken after various time intervals. The rates of hydrolysis were determined by fitting plots of concentrations (determined from $^1$H NMR peak integrals) versus time to a pseudo first-order equation using ORIGIN version 7.0. The Arrhenius activation energy (Ea), activation enthalpies ($\Delta H^\ddagger$), and activation entropy ($\Delta S^\ddagger$) for compounds ZL25, ZL33, ZL37 and ZL54 were determined from the slopes of the Arrhenius and intercepts of Eyring plots.

Determination of $pK_a$* Values. For determinations of $pK_a$* values ($pK_a$ values for solutions in $D_2O$), the pH* values of the aqua complexes ZL01A, ZL03A, ZL04A, ZL07A, ZL25A, ZL37A, ZL38A and ZL54A in $D_2O$ were varied from ca. pH* 2 to 11 by the addition of dilute NaOH and $HClO_4$, and $^1$H NMR spectra were recorded. The chemical shifts of the chelating ligands or/and methyl group of Cp* protons were plotted against pH*. The pH* titration curves were fitted to the Henderson-Hasselbalch equation, with the assumption that the observed chemical shifts are weighted averages according to the populations of the protonated and deprotonated species. These $pK_a$* values can be converted to $pK_a$ values by use of the equation $pK_a=0.929pK_a*+0.42$ as suggested by Krezel and Bal[14] for comparison with related values in the literature.

Interactions with Nucleobases. The reaction of ZL01, ZL03, ZL04, ZL07, ZL25, ZL33, ZL37, ZL38, ZL43 and ZL54 and ZL33A with nucleobases typically involved addition of a solution containing 1-2 mol equiv of nucleobase in $D_2O$, to an equilibrium solution of ZL01, ZL03, ZL04, ZL07, ZL25, ZL33, ZL37, ZL38, ZL43, ZL54 and ZL33A in a solution of 5% MeOD-$d_4$/95% $D_2O$ (v/v). $^1$H NMR spectra of these solutions were recorded at 310 K after various time intervals.

Cancer Cell Cytotoxicity. After plating, human ovarian A2780 cancer cells were treated with $Ir^{III}$ complexes on day 3 at concentrations ranging from 0.5 µM to 100 µM. Solutions of the $Ir^{III}$ complexes were made up in 0.125% DMSO to assist dissolution. Stock solutions of the IrIII complexes were firstly prepared in DMSO to assist dissolution, and then diluted into 0.9% saline and medium. After plating 5000 A2780 cells per well on day 1, IrIII complexes were added to the cancer cells on day 3 at concentrations ranging from 0.05 µM to 100 µM. Cells were exposed to the complexes for 24 h, washed, supplied with fresh medium, allowed to grow for three doubling times (72 h), and then the protein content measured (proportional to cell survival) using the sulforhodamine B (SRB) assay.[15] The standard errors are based on three replicates. The standard errors are based on two independent experiments of three replicates each.

The cytotoxicity test of ZL07, ZL33, ZL38 and ZL54 against A2780, SW480, A549 and CH1 cell lines was performed by Viktor Brabec group (Institute of Biophysics, Academy of Sciences of the Czech Republic). After plating, the cells were treated with ZL07, ZL33, ZL38 and ZL54. After 72h of incubation 10 µl of MTT (2.5 mg/ml; CALBIOCHEM) was added to each well and incubated for 4 h in culture conditions. At the end of the incubation period the medium was removed and the formazan product was dissolved in 100 µl DMSO. The cell viability was evaluated by measurement of the absorbance at 570 nm, using an Absorbance Reader SUNRICE TECAN SCHOELLER. $IC_{50}$ values (compound concentration that produces 50% of cell growth inhibition) were calculated from curves constructed by plotting cell survival (%) versus drug concentration (µM). All experiments were made in quadruplicate.

Results and Discussion

Initial complexes studied in this work are shown in Chart 1. Ir(III) (ZL07, ZL33 and ZL54), en (ZL01 and ZL31), pico (ZL03, ZL38 and ZL43), 2,2'-bipyridine-3,3'-diol (ZL44-ZL46), 2-phpy (ZL47 and ZL49), bipy(Me)$_2$ (ZL55, ZL57 and ZL59) or $[C_6H_4-2-C(H)=NPh-\kappa C,N]$ (ZL51), and Cl$^-$ as leaving group were synthesized via the abridged dimers, $[(\eta^5-Cp^x)IrCl_2]_2$ (ZLd1-ZLd3).

CHART 1

Iridium cyclopentadienyl complexes studied in this work

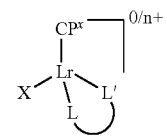

| Complex | | | | |
|---|---|---|---|---|
| X = Cl | X = D$_2$O | Cp$^x$ | L—L' | Comments |
| ZL04 | ZL04A | Cp* | bipy | n |
| ZL37 | ZL37A | Cp$^{xph}$ | bipy | s, c |
| ZL25 | ZL25A | Cp$^{xbiph}$ | bipy | s, c |
| ZL07 | ZL07A | Cp* | phen | n |

CHART 1-continued

Iridium cyclopentadienyl complexes studied in this work

| | | | | |
|---|---|---|---|---|
| ZL33 | ZL33A | Cp$^{xph}$ | phen | s, c |
| ZL54 | ZL54A | Cp$^{xbiph}$ | phen | s |
| ZL01 | ZL01A | Cp* | en | s |
| ZL31 | | Cp$^{xph}$ | en | s, c |
| ZL03 | ZL03A | Cp* | pico | n |
| ZL38 | ZL38A | Cp$^{xph}$ | pico | s, c |
| ZL43 | ZL43A | Cp$^{xbiph}$ | pico | s |
| ZL02 | | CP* | acac | s, c |
| ZL44 | | Cp* | bipy(OH)O | s, c |
| ZL45 | | Cp$^{xph}$ | bipy(OH)$_2$ | s |
| ZL46 | | Cp$^{xbiph}$ | bipy(OH)O | s, c |
| ZL47 | | Cp* | 2-phpy | n |
| ZL49 | | Cp$^{xbiph}$ | 2-phpy | s, c |
| ZL51 | | Cp* | ph-2-C(H)=Nph | n |
| ZL55 | | Cp* | 4,4'-Me$_2$-bipy | s |
| ZL57 | | Cp$^{xph}$ | 4,4'-Me$_2$-bipy | s, c |
| ZL59 | | Cp$^{xbiph}$ | 4,4'-Me$_2$-bipy | s |
| ZL56 | | Cp* | 2,2'-Me$_2$-phen | n |
| ZL86 | | Cp* | phen-5-amine | n |
| ZL67 | | Cp* | bq | n |
| ZL71 | | Cp$^{xph}$ | bq | n |
| ZL68 | | Cp* | 2-phq | n |
| ZL72 | | Cp$^{xph}$ | 2-phq | n |
| ZL69 | | Cp* | tpy | n |
| ZL73 | | Cp$^{xph}$ | tpy | n, c |
| ZL75 | | Cp$^{xbiph}$ | tpy | n |
| ZL74 | | Cp* | 2-dfphpy | n |
| ZL78 | | Cp$^{xph}$ | 2-dfphpy | n | s: synthesis is included in experimental section;
n: synthesis is not included;
c: X-ray crystal structure is obtained.

Cp$^x$

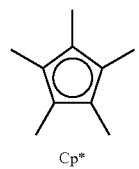

Cp*

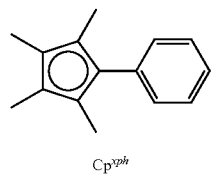

Cp$^{xph}$

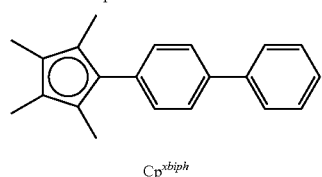

Cp$^{xbiph}$

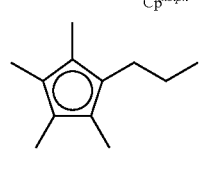

Cp$^{ypr}$

L—L'

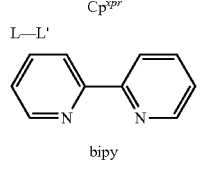

bipy

CHART 1-continued

Iridium cyclopentadienyl complexes studied in this work

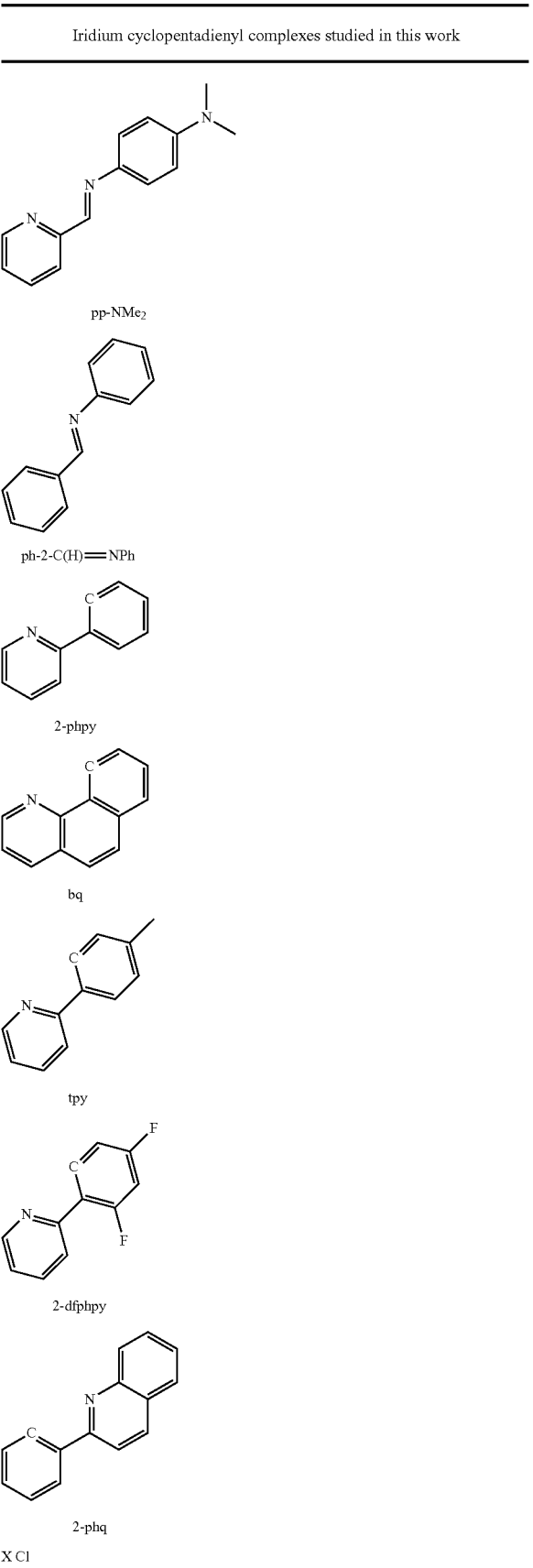

pp-NMe2 ph-2-C(H)=NPh 2-phpy bq tpy 2-dfphpy 2-phq

XCl

CHART 1-continued

Iridium cyclopentadienyl complexes studied in this work

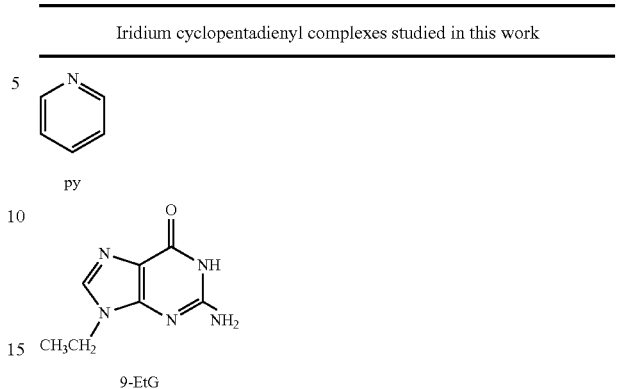

py

9-EtG

Figure 2:
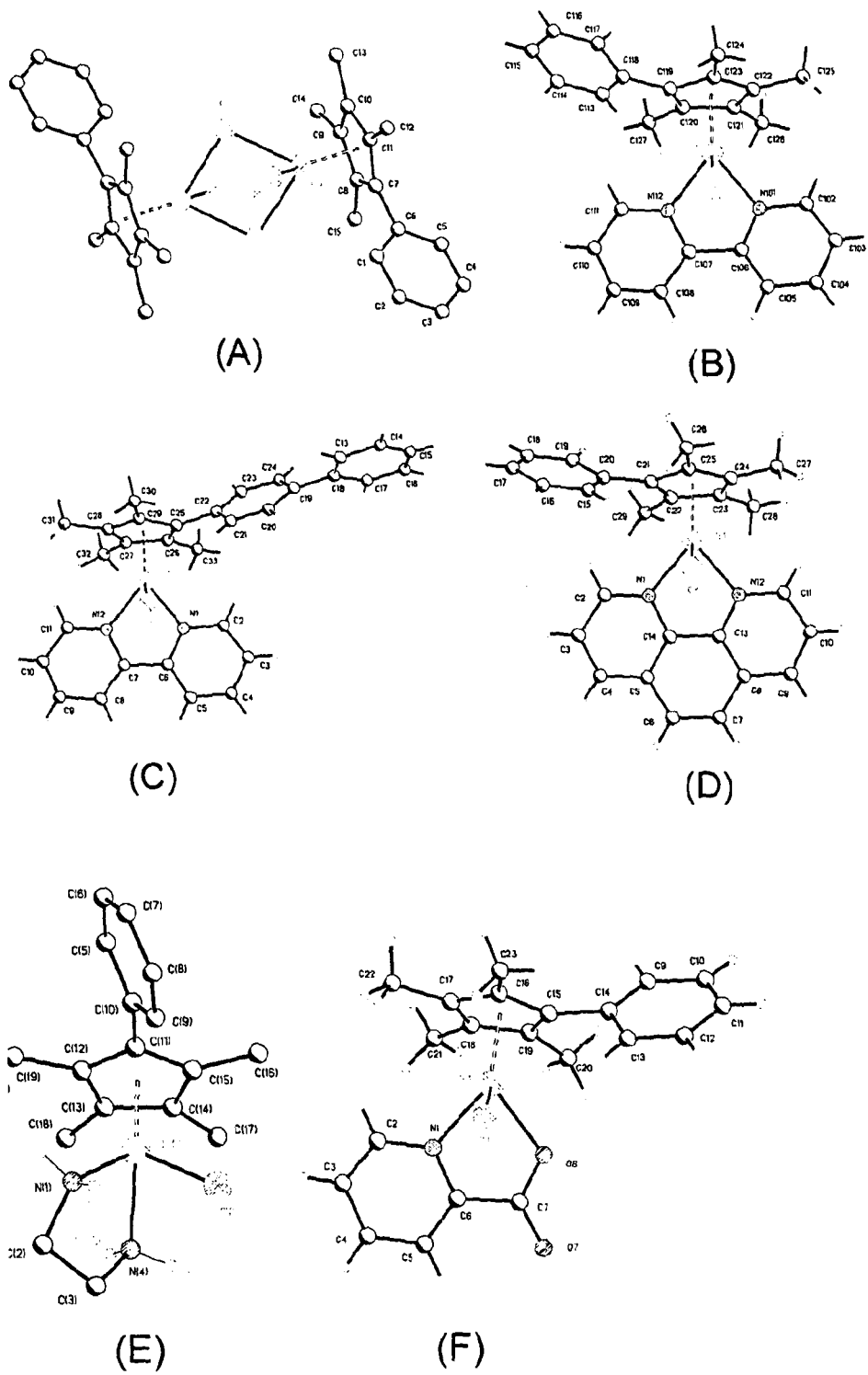
FIG. 2. shows X-ray crystal structures of compounds according to the present invention with atom numbering scheme for (A) $[(\eta^5-C_6Me_4C_6H_5)IrCl_2]_2$ (ZLd2), (B) $[(\eta^5-C_5Me_4C_6H_5Ir(bipy)Cl]PF_6$ (ZL37PF$_6$), (C) $[(\eta^5-C_5Me_4C_6H_4C_6H_5)Ir(bipy)Cl]PF_6$ (ZL25PF$_6$), (D) $[(\eta^5-C_5Me_4C_6H_5)Ir(phen)Cl]PF_6$ (ZL33PF$_6$), (E) $[(\eta^5-C_5Me_4C_6H_5)IrCl(H_2NCH_2CH_2NH_2-N,N)]BPh_4$ (ZL31BPh$_4$), (F) $[(\eta^5-C_5Me_4C_6H_5)Ir(\eta^2-C_5H_4N-2-CO_2)Cl]$ (ZL38), (G) $[(\eta^5-C_5Me_6)Ir(acac)Cl]$ (ZL02), (H) $[(\eta^5-C_5Me_6)Ir(bipy(OH)O)Cl]$ (ZL44), (I) $\{(\eta^5-C_5Me_4C_6H_4C_6H_5)Ir[bipy(OH)(O)]Cl\}$ (ZL46), (J) $[(\eta^5-C_5Me_4C_6H_4C_6H_5)Ir(2-phpy)Cl]$ (ZL49), (K) $[(\eta^5-C_5Me_4C_6H_5)Ir(bipy(Me)_2)Cl]PF_6 \cdot CH_3CH_2OCH_2CH_3$ (ZL57.CH$_3$CH$_2$OCH$_2$CH$_3$) and (L) $[(\eta^5-C_5Me_4C_6H_5)Ir(tpy)Cl]$ (ZL73) with thermal ellipsoids drawn at 50% probability. The hydrogen atoms in (A), (E) and (H), the PF$_6$ counter ions in (B), (C), (D) and BPh$_4$ counter ion in (E) have been omitted for clarity.
Figure 2:
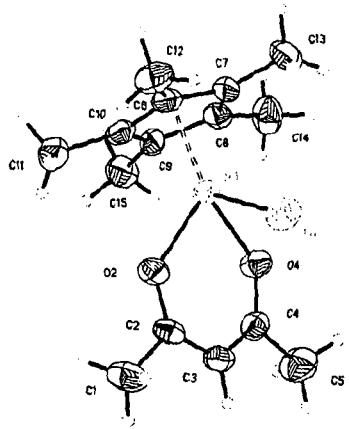
Figure 2:
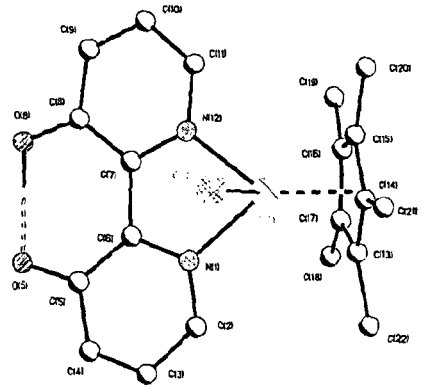

X-ray Crystal Structures. The X-ray crystal structures of $[(\eta^5\text{-}C_5Me_5)Ir(acac)Cl]$ (ZL02), $[(\eta^5\text{-}C_5Me_4C_6H_5)IrCl_2]_2$ (ZLd2), $[(\eta^5\text{-}C_5Me_4C_6H_5)IrCl(H_2NCH_2CH_2NH_2\text{—}N,N)]$ $BPh_4$ (ZL31BPh$_4$), $[(\eta^5\text{-}C_5Me_4C_6H_5)Ir(\eta^2\text{-}C_5H_4N\text{-}2\text{-}CO_2)Cl]$ (ZL38), $[(\eta^5\text{-}C_5Me_4C_6H_5)Ir(bipy)Cl]$ $PF_6$ (ZL37PF$_6$), $[(\eta^5\text{-}C_5Me_4C_6H_5)Ir(phen)Cl]PF_6$(ZL33PF$_6$), $[(\eta^5\text{-}C_5Me_4C_6H_4C_6H_5)Ir(bipy)Cl]PF_6$(ZL25PF$_6$), $[(\eta^5\text{-}C_5Me_5)Ir(bipy(OH)O)Cl]$ (ZL44), $\{(\eta^5\text{-}C_5Me_4C_6H_4C_6H_5)$ Ir[bipy(OH)(O)]Cl$\}$ (ZL46), $[(\eta^5\text{-}C_5Me_4C_6H_4C_6H_5)Ir(2\text{-}phpy)Cl]$ (ZL49), $(\eta^5\text{-}C_5Me_4C_6H_5)Ir(bipy(Me)_2)Cl]$ $PF_6\cdot CH_3CH_2OCH_2CH_3$ (ZL57$\cdot$CH$_3$CH$_2$OCH$_2$CH$_3$) and $[(\eta^5\text{-}C_5Me_4C_6H_5)Ir(tpy)Cl]$ (ZL73) were determined. Their structures and atom numbering schemes are shown in FIG. 2. The complexes, except dimer ZLd2, adopt the expected pseudo-octahedral "three-leg piano-stool" geometry with the iridium π-bonded to the cyclopentadienyl ligand (1.747-1.789 Å to centroid of ring), σ-bonded to a chloride (2.384-2.415 Å) and a chelating ligand, which constitute the three legs of the piano stool.

Kinetics of Hydrolysis.

We show that the nature of the ligands attached to Ir(III), including the substituents on the cyclopentadienyl ring and the other chelating and monodentate ligands, can have a significant effect on the rate and extent of hydrolysis. Since the hydrolysis step can control the rate of reactions it can also significantly affect the biological activity of this class of compounds.

Figure 3:
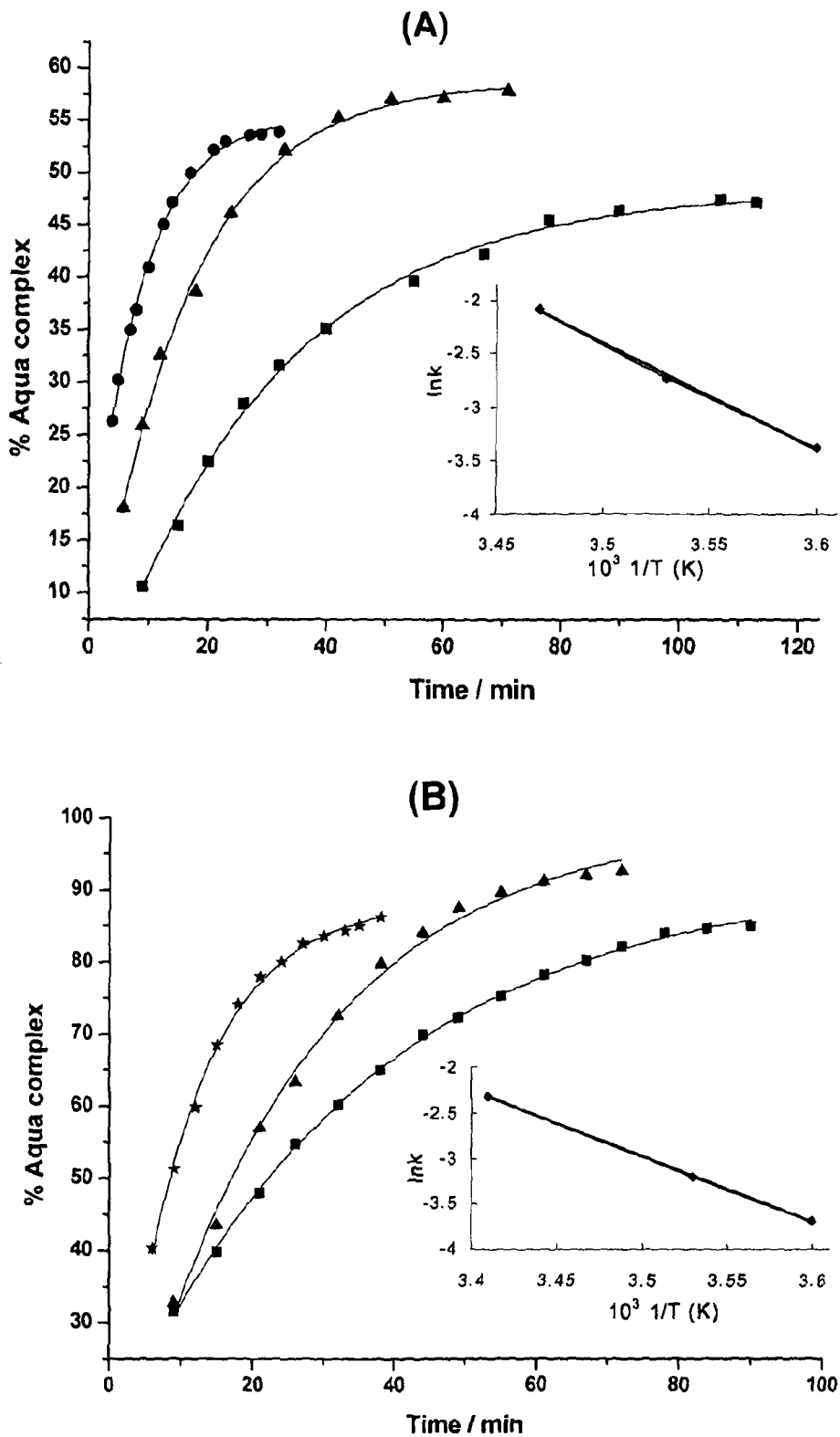
FIG. 3. shows time dependence for formation of the aqua complexes (A) ZL37A, (B) ZL25A, (C) ZL33A, and (D) ZL54A (based on $^1$H NMR peak integrals) during hydrolysis of ZL25, ZL33, ZL37 and ZL54 in acidic D$_2$O (pH* 3) at 278 K (■), 283 K (▲), 288 K (●), 293 K (★). The inset shows the Arrhenius plot, the slope of which gives the Arrhenius activation energy Ea.
Figure 3:
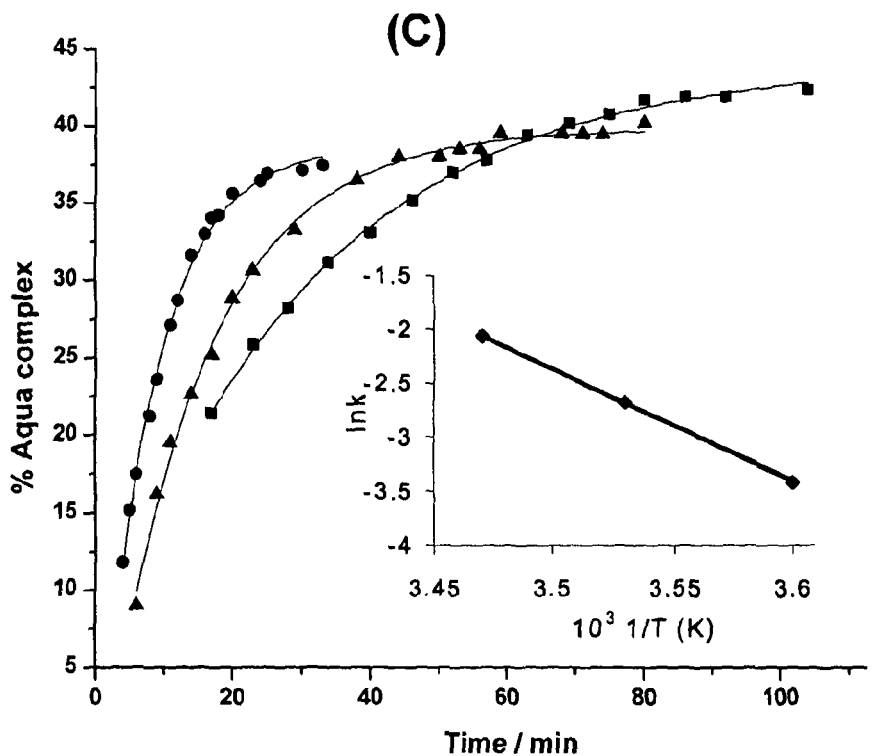
Figure 3:
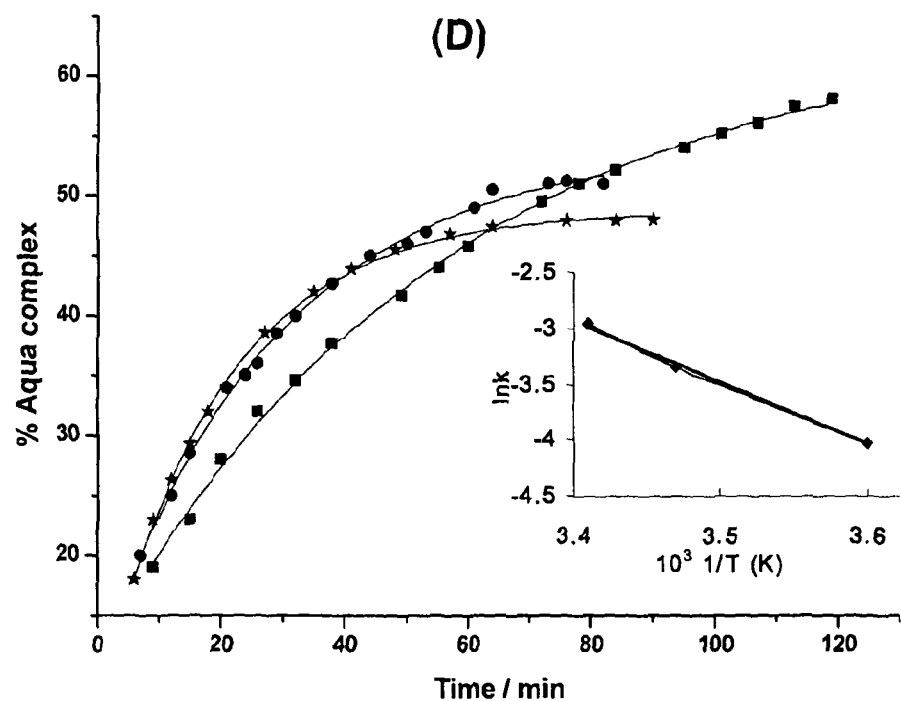

The rates of hydrolysis of compounds ZL01-ZL04, ZL07, ZL25, ZL33, ZL37, ZL38, ZL43 and ZL54 in a 5% MeOD-d$_4$/95% D$_2$O were monitored by $^1$H NMR at different temperature from 278 to 298 K by the observation of new peaks over time due to aqua adduct formation. Five percent MeOD was used to improve solubility, and acidic conditions (D$_2$O, pH* 3) were used to prevent the deprotonation of the aqua complex as a secondary reaction. The hydrolysises of compound ZL01-ZL04 and ZL07 containing Cp*, ZL38 and ZL43 containing picolinate were too rapid to be observed by $^1$H NMR even at 278K. The percentage of aqua peak formation for ZL25, ZL33, ZL37 and ZL54 was plotted against time and was fitted to pseudofirst order kinetics (FIG. 3), and their halflife times were calculated (Table 1). The Arrhenius activation energy (Ea), activation enthalpy ($\Delta H^\ddagger$), and activation entropy ($\Delta S^\ddagger$) of compound ZL25, ZL33, ZL37 and ZL54 are listed in Table 4. The large negative $\Delta S^\ddagger$ value for compound ZL54 is notable. The extent of hydrolysis at equilibrium is medium for all compounds, ranged from 30% to 60%.

TABLE 1

Hydrolysis Data and Activation Parameters for Compounds
ZL25, ZL33, ZL37 and ZL54 at Various Temperatures

| compound | T/K | k/min$^{-1}$ | t$_{1/2}$/min | Ea/ kJ mol$^{-1}$ | kJ ΔH$^{‡}$/ mol$^{-1}$ | kJ ΔS$^{‡}$/ J K$^{-1}$mol$^{-1}$ |
|---|---|---|---|---|---|---|
| ZL37 | 278 | 0.0341 | 20.3 | | | |
| | 283 | 0.0652 | 10.6 | 82.4 | 79.8 | 14.7 |
| | 288 | 0.1229 | 5.6 | | | |
| ZL25 | 278 | 0.0249 | 27.8 | | | |
| | 283 | 0.0405 | 17.1 | 60.4 | 58.1 | −66.02 |
| | 293 | 0.0986 | 7.0 | | | |
| ZL33 | 278 | 0.033 | 21.0 | | | |
| | 283 | 0.0693 | 10.0 | 85.8 | 83.94 | 29.3 |
| | 288 | 0.1264 | 5.5 | | | |
| ZL54 | 278 | 0.0179 | 38.7 | | | |
| | 288 | 0.0352 | 19.7 | 45.6 | 43.4 | −121.2 |
| | 293 | 0.0516 | 13.4 | | | |

Figure 4:
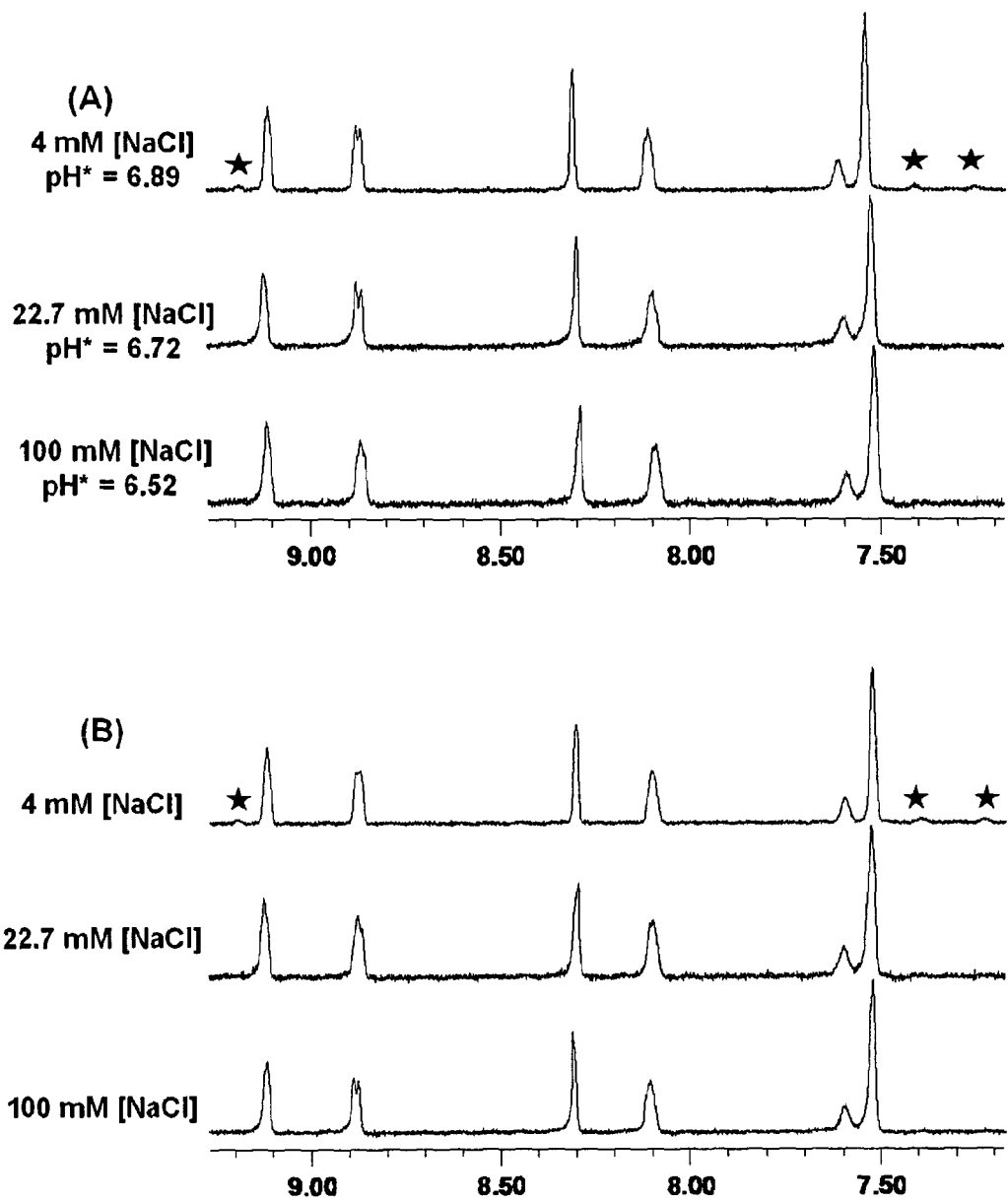
FIG. 4. shows the effect of various concentrations of NaCl close to those of blood plasma (100 mM), cell cytoplasm (22.7 mM) and cell nucleus (4 mM) on the low field region of the $^1$H NMR (600 MHz) spectrum of a 1 mM solution of ZL33 in D$_2$O at 310 K. (A) t=10 min and (B) t=24 h, where peaks labelled ★ represent hydrolysed ZL33 (ZL33A). Note: some peaks of ZL33 and ZL33A overlap.

The effects of chloride concentrations typical of blood plasma (100 mM), cell cytoplasm (22.7 mM), and cell nucleus (4 mM) on the aqueous chemistry of ZL33 was investigated. $^1$H NMR spectra of ZL33 (1 mM) were recorded within 10 min of sample preparation and after incubation at 310 K for 24 h (FIG. 4). On the basis of $^1$H NMR peak integrals, almost no hydrolyzed complex ZL33 (ZL33A) was found to be present in 100 mM [Cl] (pH* 6.52) or in 22.7 mM [Cl] (pH* 6.72), and only 5% of ZL33A at 4 mM [Cl] (pH* 6.89) after 10 min. No significant change was observed after 24 h, see Table 2.

TABLE 2

Percentage of Aqua Adduct Formation in a Solution of 1 mM ZL33
in D$_2$O at Chloride Levels Typical of Cell Nucleus (4 mM),
Cell Cytoplasm (22.7 mM), and Blood Plasma (100 mM)

| | % aqua adduct of ZL33 (ZL33A) | |
|---|---|---|
| NaCl | t = 10 min | t = 24 h |
| 4 mM | 5 | 5 |
| 22.7 mM | 0 | 0 |
| 100 mM | 0 | 0 | pK$_a$* Dependence.

Knowledge of the acidity of aqua adducts can be important in the drug process since aqua adducts can be more reactive than their hydroxo forms.

The changes in the $^1$H NMR chemical shifts for the protons of the coordinated chelating ligands in compounds ZL25A, ZL54A, ZL38A, chelating ligands and methyl group in Cp* or Cp$^{xph}$ in compounds ZL04A, ZL07A, ZL37A, ZL03A, and methyl group in Cp* in compound ZL01A were followed with change in pH* over a range of 2-11. The mean pK$_a$* value was taken for each complex.

When the pH* values of the solutions were increased from about 2 to 11, the NMR peaks assigned to ZL01A, ZL03A, ZL04A, ZL07A, ZL25A, ZL37A, ZL38A and ZL54A gradually shifted to high field in the spectrum. The resulting pH titration curves were fitted to the modified Henderson-Hasselbach equation.[16,17] This gave rise to pK$_a$* values between 6.28 and 7.99 (Table 3).

TABLE 3 pK$_a$* and pK$_a$ Values$^a$ for the Deprotonation of the Coordinated D$_2$O in
complexes ZL01A, ZL03A, ZL04A, ZL07A, ZL25A, ZL37A, ZL38A
and ZL54A

| complex | | pK$_a$* | pK$_a$ |
|---|---|---|---|
| [(η$^5$-C$_5$Me$_5$)Ir(bipy)OD$_2$]$^{2+}$ | ZL04A | 6.94 | 6.86 |
| [(η$^5$-C$_5$Me$_4$C$_6$H$_5$)Ir(bipy)OD$_2$]$^{2+}$ | ZL37A | 6.31 | 6.28 |
| [(η$^5$-C$_5$Me$_4$C$_6$H$_4$C$_6$H$_5$)Ir(bipy)OD$_2$]$^{2+}$ | ZL25A | 6.68 | 6.63 |
| [(η$^5$-C$_5$Me$_5$)Ir(phen)OD$_2$]$^{2+}$ | ZL07A, | 7.88 | 7.74 |
| [(η$^5$-C$_5$Me$_4$C$_6$H$_4$C$_6$H$_5$)Ir(phen)OD$_2$]$^{2+}$ | ZL54A | 7.50 | 7.38 |
| [(η$^5$-C$_5$Me$_5$)IrCl(en)OD$_2$]$^{2+}$ | ZL01A | 7.66 | 7.54 |
| [(η$^5$-C$_5$Me$_5$)Ir(pico)OD$_2$]$^+$ | ZL03A | 8.15 | 7.99 |
| [(η$^5$-C$_5$Me$_4$C$_6$H$_5$)Ir(pico)OD$_2$]$^+$ | ZL38A | 7.75 | 7.62 |

$^a$pK$_a$ values calculated from pK$_a$* according to Krezel and Bal.[14]

Interactions with Nucleobases.

Since DNA is a potential target site for transition metal anticancer complexes,[18] nucleobase binding reactions of compounds ZL01, ZL03, ZL04, ZL07, ZL25, ZL33, ZL33A, ZL37, ZL38, ZL43 and ZL54 with nucleobase models 9-ethylguanine (9-EtG) and 9-ethyladenine (9-EtA), were investigated. Solutions of ZL01, ZL03, ZL04, ZL07, ZL25, ZL33, ZL37, ZL38, ZL43 and ZL54 (1 mM) (containing an equilibrium mixture of these complexes and their respective aqua adducts) with 1 mol equivalent of 9-EtG or 9-EtA in D$_2$O were prepared, and $^1$H NMR spectra were recorded at different time intervals. The percentages of nucleobase adducts formed by all compounds based on $^1$H NMR peak integrals are displayed in Table 4.

TABLE 4

Extent of 9-EtG and 9-EtA adduct formation for compounds ZL01, ZL03,
ZL04, ZL07, ZL25, ZL33, ZL37, ZL38, ZL43 and ZL54 at different time intervals

| | | | Reaction with 9-EtG | | Reaction with 9-EtA | | A2780 |
|---|---|---|---|---|---|---|---|
| Complex | Ring | Chelating ligand | 10 min | 24 h | 10 min | 24 h | IC$_{50}$ (µM) |
| ZL01 | Cp* | en(N,N-) | 100% | 100% | 0 | 0 | >100 |
| ZL04 | Cp* | bipy(N,N-) | 28.2% | 60.6% | 0 | 0 | >100 |
| ZL37 | Cp$^{xph}$ | bipy(N,N-) | 18.6% | 46.9% | 0 | 0 | 15.9 |
| ZL25 | Cp$^{xbiph}$ | bipy(N,N-) | 24.2% | 55.2% | 0 | 0 | 0.57 |
| ZL07 | Cp* | phen(N,N-) | 73.1% | 83.3% | 0 | 0 | >100 |
| ZL33 | Cp$^{xph}$ | phen(N,N-) | 15.5% | 42.2% | 0 | 0 | 6.7 |
| ZL33A | Cp$^{xph}$ | phen(N,N-) | 65% | 73% | 0 | 0 | ND |
| ZL54 | Cp$^{xbiph}$ | phen(N,N-) | 62.2% | 90% | 0 | 0 | 0.72 |
| ZL03 | Cp* | pico(N,O-) | 100% | 100% | 80.8% | 80.7% | >100 |
| ZL38 | Cp$^{xph}$ | pico(N,O-) | 100% | 100% | 76.0% | 76.0% | >100 |
| ZL43 | Cp$^{xbiph}$ | pico(N,O-) | 100% | 100% | 71% | 71% | 16.3 |

ND: not determined

Figure 5:
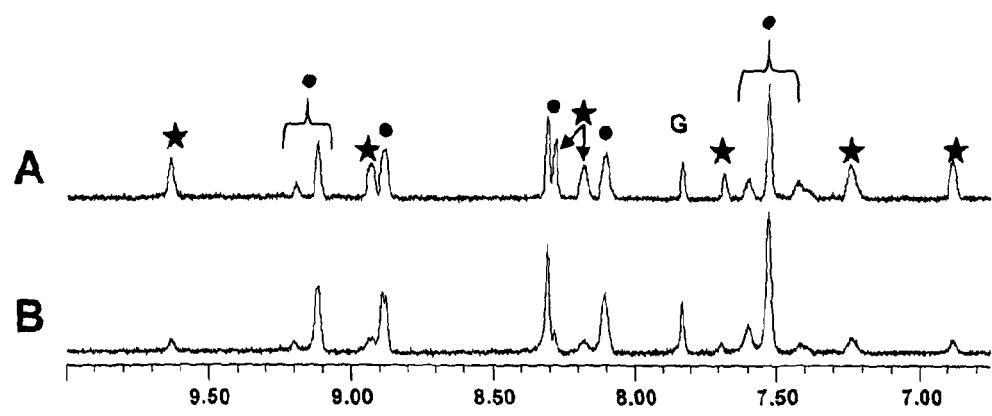
FIG. 5. shows reaction of $[(\eta^5-C_5Me_4C_6H_5)Ir(phen)Cl]PF_6$ (ZL33) with 9-ethylguanine. (A) $^1$H NMR spectrum of an equilibrium solution of ZL33, after 24 h; (B) 10 min after addition of 1 mol equiv 9-ethylguanine in D$_2$O at 310 K, pH* 7.21. Assignments: peaks labelled ★ represent the product, $[(\eta^5-C_5Me_4C_6H_5)Ir(phen)(9-EtG-N7)]^{2+}$, (16), peaks labelled ● represent intact chloro complex ZL33 and the hydrolysis product $[(\eta^5-C_5Me_4C_6H_5)Ir(phen)(OD_2/OD)]^{2+/+}$ (ZL33 A), G unreacted 9-ethylguanine (9-EtG). After 24 h, 42% of ZL33 had reacted.
Figure 6:
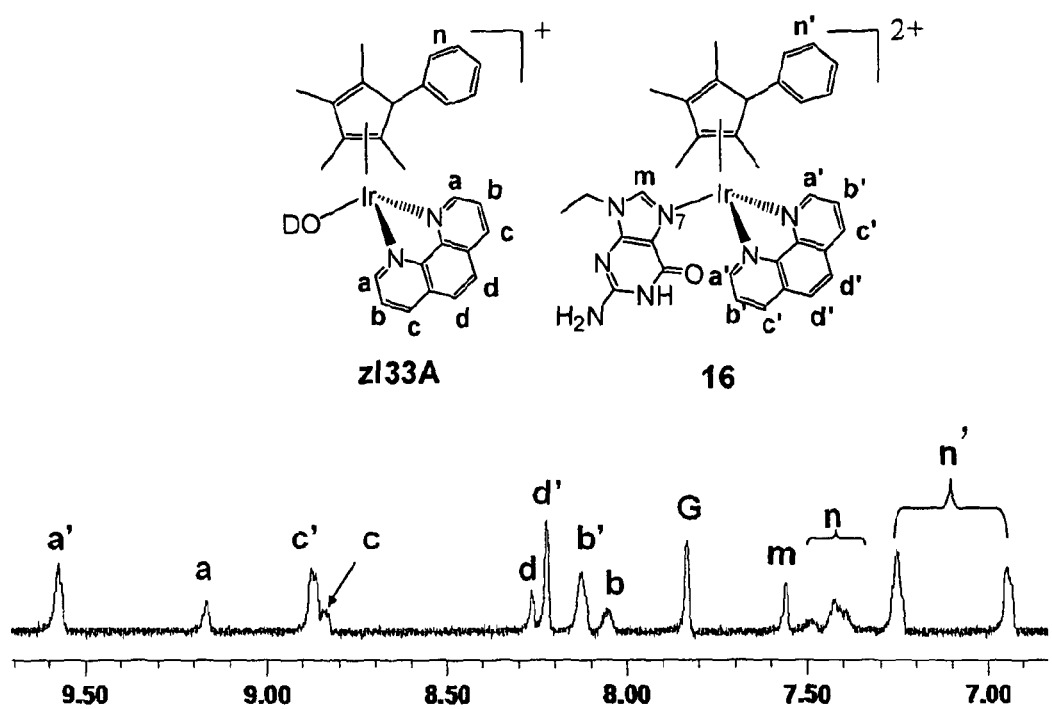
FIG. 6. shows the reaction of 9-ethylguanine with $[(\eta^5-C_5Me_4C_6H_5)Ir(phen)(OD_2/OD)]^{2+/+}$ (ZL33 A). Low-field region of the $^1$H NMR spectrum of ZL33A (formed by treating a solution of the chloro complex ZL33 with 1 mol equiv of AgNO$_3$) after reaction with 2 mol equiv of 9-EtG in D$_2$O at 310 K for 24 h. At this time, 73% of ZL33A had reacted to form $[(\eta^5-C_5Me_4C_6H_5)Ir(phen)(9-EtG-N7)]^{2+}$ (16). Peak labels correspond to the structures; peak G is from H8 of unbound 9-EtG.

Addition of 1 mol equiv of 9-EtG to an equilibrium solution of complex ZL33, [($\eta^5$-C$_5$Me$_4$C$_6$H$_5$) Ir(phen)Cl]PF$_6$, in D$_2$O (pH* 7.21) at 310 K resulted in 15% of ZL33 reacted after 10 min, and a new H8 peak appeared at 7.68 ppm (for species 16, see FIG. 5), shifted by 0.15 ppm to high field relative to that of free 9-EtG. After 24 h, 42% of ZL33 had reacted. Addition of 2 mol equiv of 9-EtG to a solution of ZL33A (prepared by treating a solution of ZL33 with 1 mol equiv of AgNO$_3$) resulted in new peaks assignable to 16 had appeared, and 65% of ZL33A had reacted with 9-EtG to form 16 after 10 min. After 24 h, 73% of ZL33 had reacted (FIGS. 6).

Figure 7:
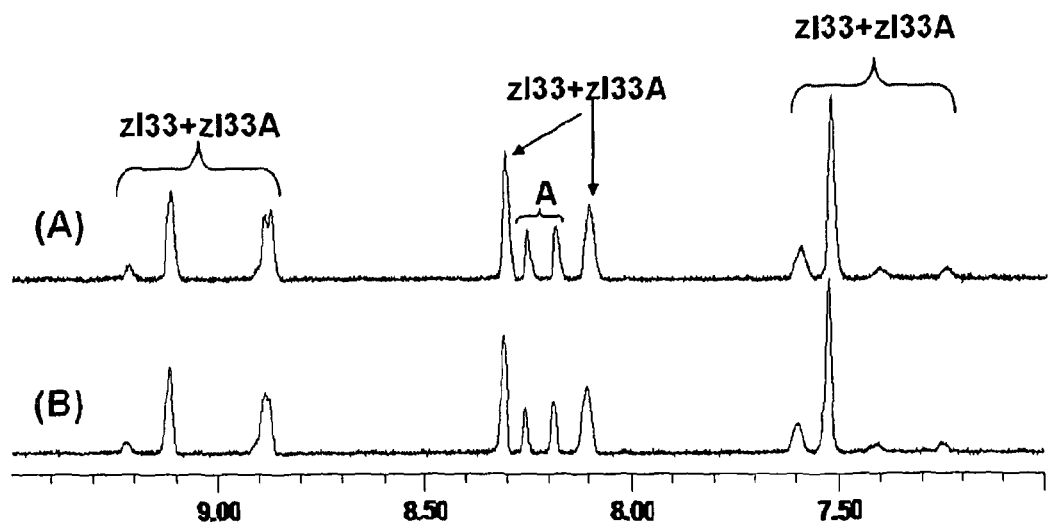
FIG. 7. shows reaction of $[(\eta^5-C_5Me_4C_6H_5)Ir(phen)Cl]PF_6$ (ZL33) with 9-ethyladenine. (A) $^1$H NMR spectrum of an equilibrium solution of ZL33, after 24 h; (B) 10 min after addition of 1 mol equiv 9-ethyladenine in D$_2$O at 310 K, pH* 7.15. Assignments: ZL33A, $[(\eta^5-C_5Me_4C_6H_5)Ir(phen)(OD_2/OD)]^{2+}$; A, unreacted 9-ethyladenine (9-EtA). After 24 h, no reaction is observed.

The addition of a solution of 1 mol equiv of 9-EtA to an equilibrium solution of ZL33 in D$_2$O at 310 K resulted in no additional $^1$H NMR peaks over a period of 24 h (FIG. 7). Similarly, compounds ZL04, ZL07, ZL25, ZL37 and ZL54 containing 2,2'-bipyridine or 1,10-phenanthroline chelating ligand only formed 9-EtG adducts, with extent of 19%-83% completion after 24 h.

Figure 8:
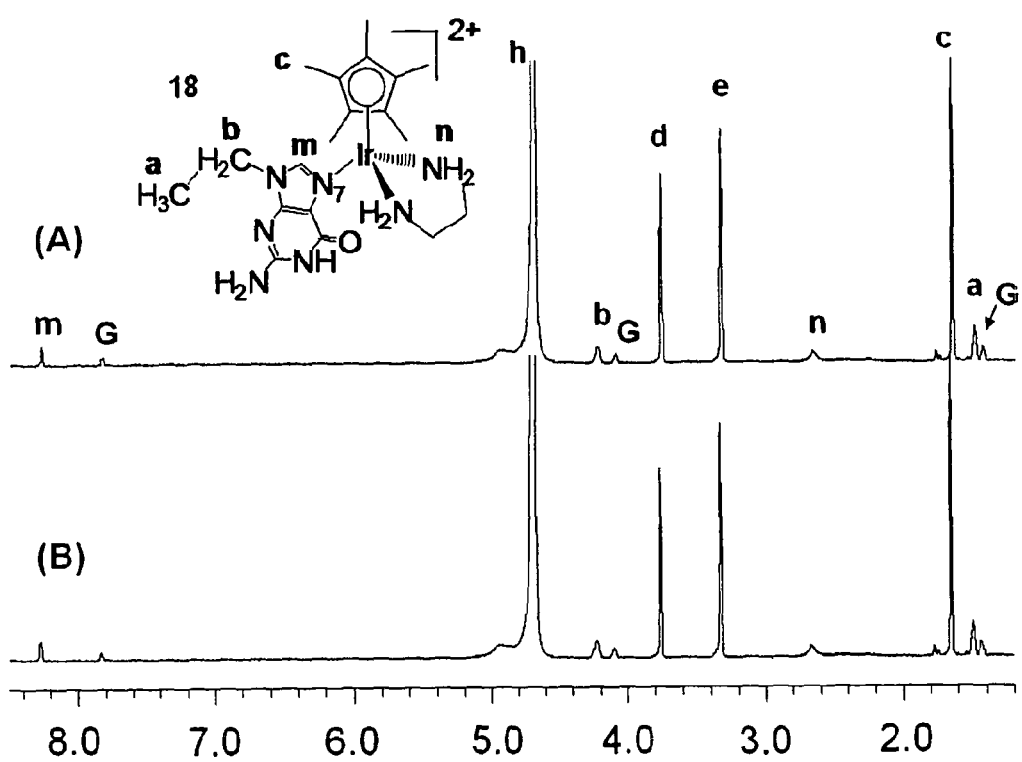
FIG. 8. shows the reaction of $[(\eta^5-C_5Me_5)Ir(en)Cl]PF_6$ (ZL01) with 9-ethylguanine (excessive in this reaction). (A) $^1$H NMR spectrum of an equilibrium solution of ZL01, after 24 h; (B) 10 min after addition of 1 mol equiv 9-ethylguanine in D$_2$O at 310 K, pH* 6.74. Assignments: Peak labels correspond to the structure; peak G is from unbound 9-EtG. h H$_2$O, e MeOH, d dioxane. 100% of ZL01 had reacted within 10 min.
Figure 9:
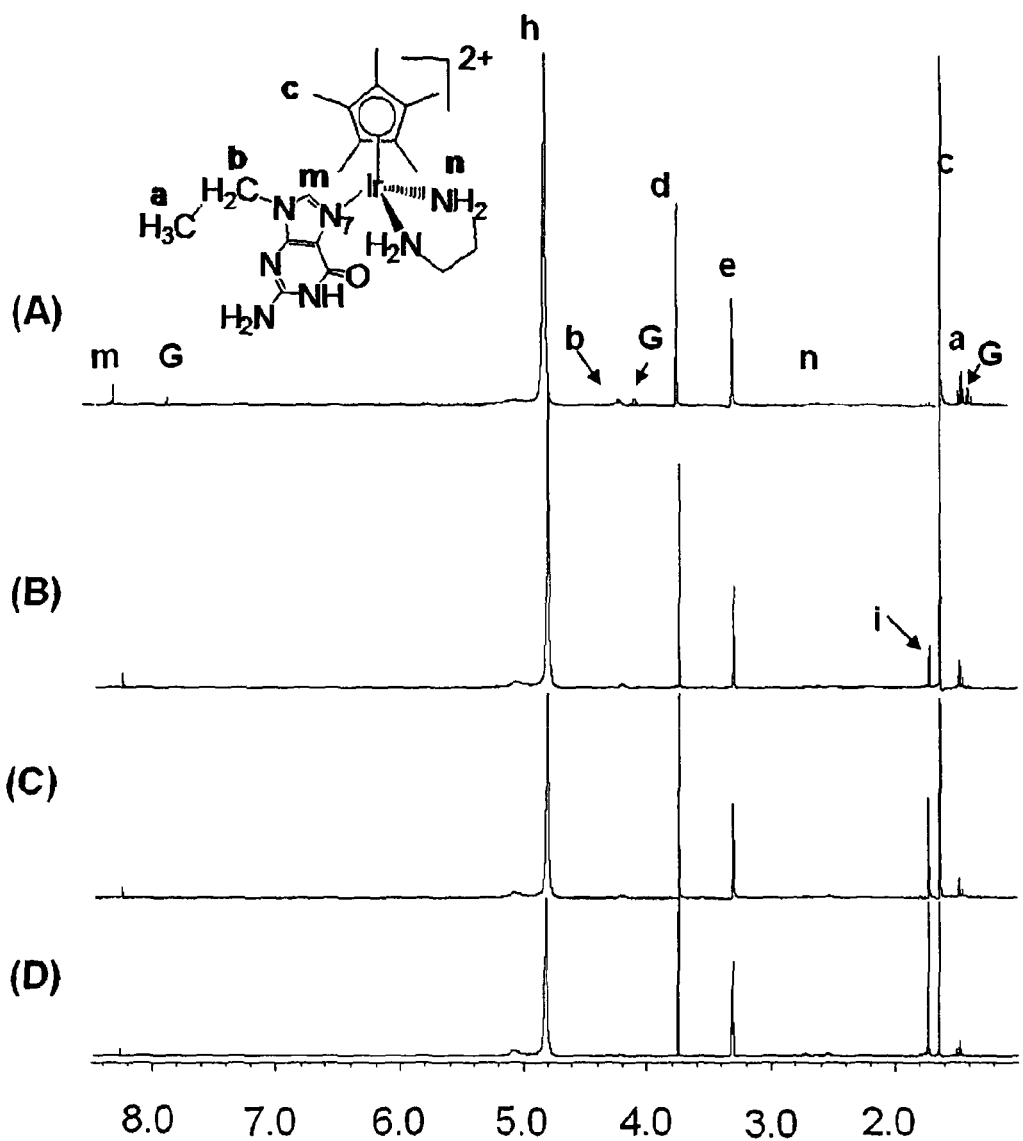
FIG. 9. shows the reaction of $[(\eta^5-C_5Me_5)Ir(en)Cl]PF_6$ (ZL01) with increasing amount of 9-ethylguanine (excessive finally). (D) $^1$H NMR spectrum, 10 min after addition of 0.5 mol equiv 9-EtG in D$_2$O at 310 K; (C) 10 min after more addition of 0.2 mol equiv 9-EtG in D$_2$O at 310 K; (B) 10 min after more addition of 0.2 mol equiv 9-EtG in D$_2$O at 310 K; (D) 10 min after more addition of 0.3 mol equiv 9-EtG in D$_2$O at 310 K. Assignments: Peak labels correspond to the structure; peak i is from methyl peak of ZL01+ZL01A, peak G is from unbound 9-EtG. h H$_2$O, e MeOH, d dioxane.

Compound ZL01 showed an exceptionally high affinity with 9-EtG with 100% nucleobase adduct formation (for species 18), within 10 min, FIG. 8, in which only one main peak assignable to CH$_3$ protons in Cp* ring was observed and there is no obvious difference between the two $^1$H NMR spectra of 10 min and 24 h. The strong binding ability with 9-EtG was further confirmed by addition of a solution of 1 mol equiv of 9-EtG gradually to an equilibrium solution of ZL01 in 5% MeOD-d$_4$/95% D$_2$O (v/v) at 310 K and record $^1$H NMR spectra within 10 min each time, FIG. 9. With the addition of 9-EtG, the intensity of methyl peak of ZL01+ZL01A decreased and eventually disappear when 9-EtG is a little excessive, while the intensities of peaks of 9-EtG in compound 18 grew and a set of new peaks assignable to free 9-EtG appeared finally.

These data show that the rate and extent of reactions, and selectivity towards DNA bases (potential drug target sites), of these organometallic iridium complexes depend on the nature of the cyclopentadienyl ligand and its substituents, and on the chelated and monodentate ligands.

Cytotoxicity Data.

Figure 10:
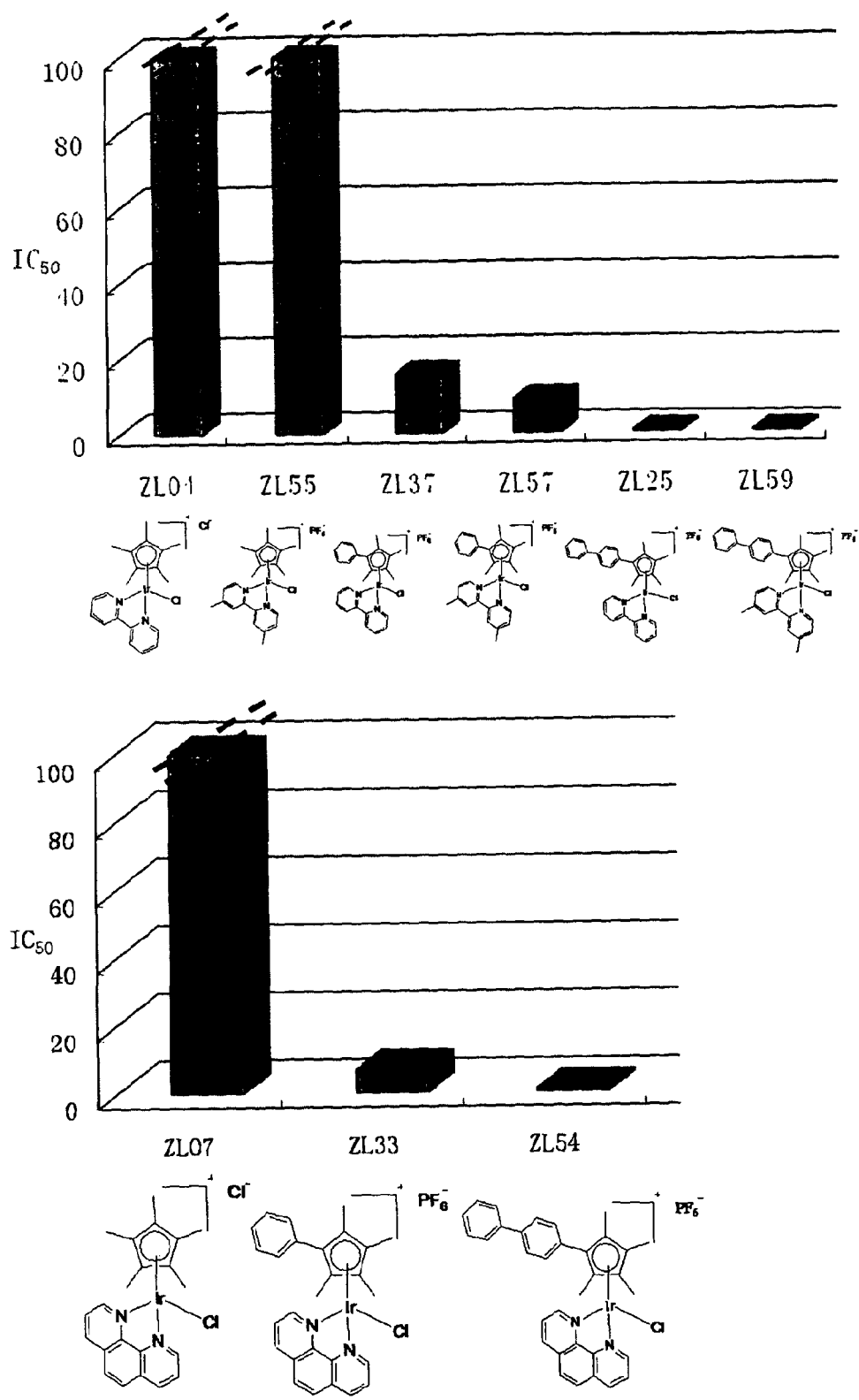
FIG. 10. is bar charts showing the IC$_{50}$ (μM) of iridium complexes towards A2780 cancer cell line. Dashed line means the IC$_{50}$ is over 100 μM.
Figure 10:
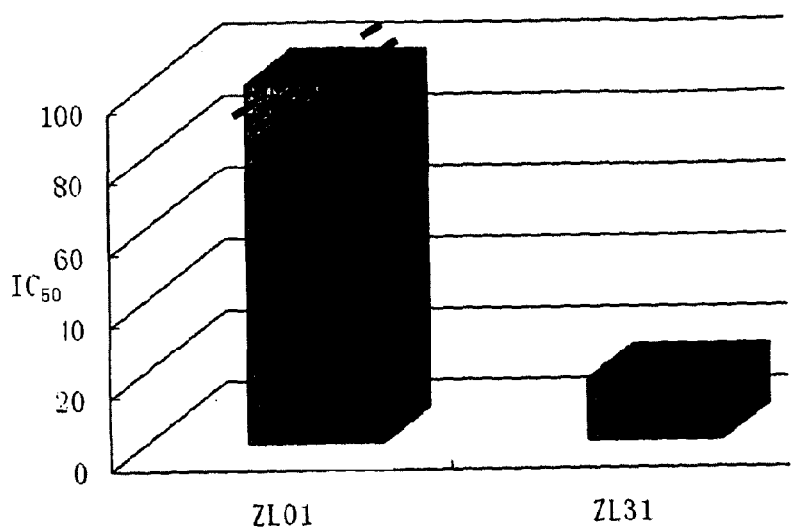
Figure 10:
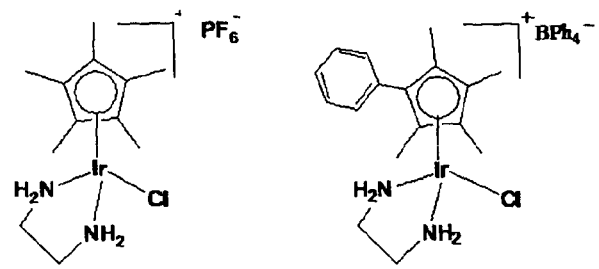
Figure 10:
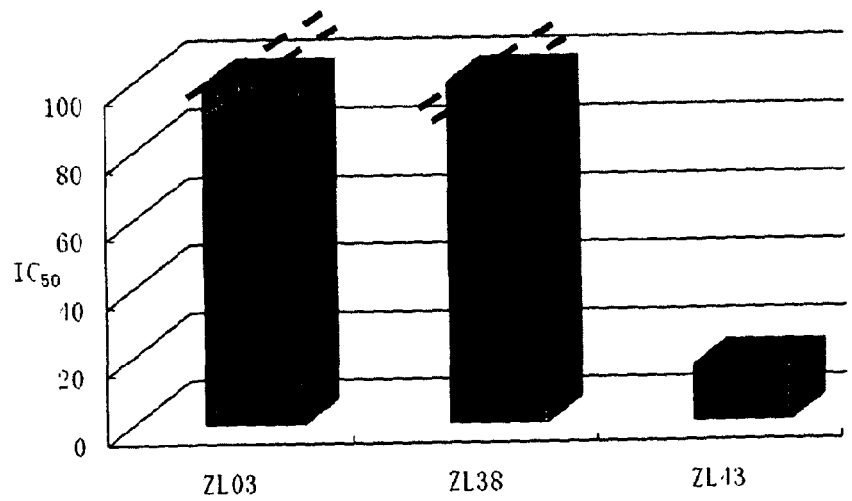
Figure 10:
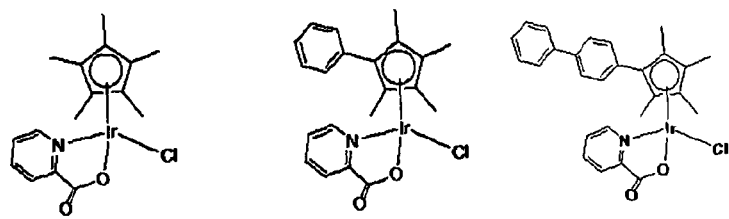
Figure 10:
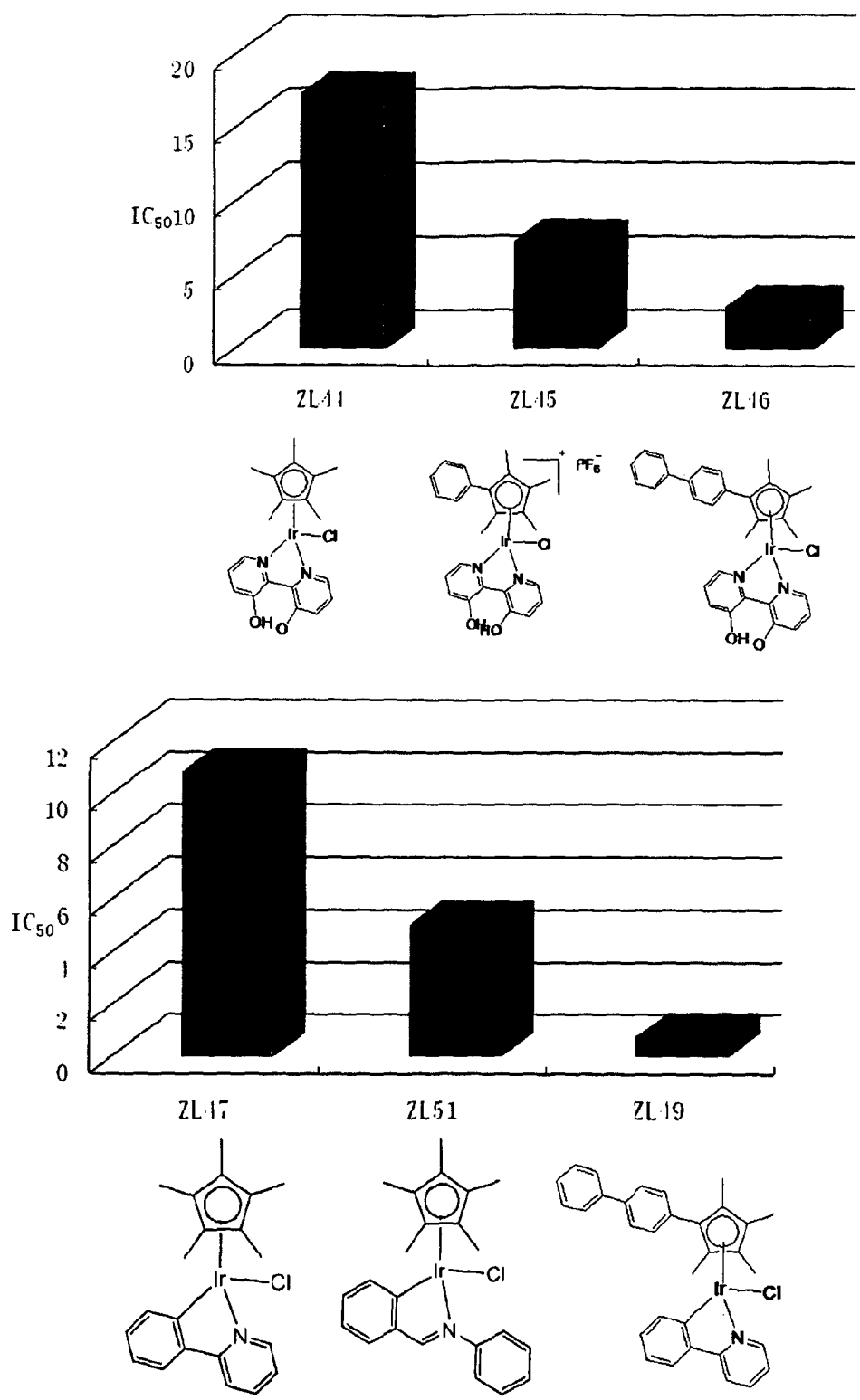

The cytotoxicity of complexes ZL01-ZL04, ZL07, ZL25, ZL31, ZL33, ZL37, ZL38, ZL43, ZL54, ZL44-ZL47, ZL49, ZL51, ZL55, ZL57 and ZL59 toward ovarian A2780 cancer cell line was investigated (Table 5 and FIG. 10).

TABLE 5

In vitro growth inhibition of A2780 cancer cell lines for compounds ZL01-ZL04, ZL07, ZL25, ZL31, ZL33, ZL37, ZL38, ZL43, ZL54, ZL44-ZL47, ZL49, ZL51, ZL55, ZL57 and ZL59 and cisplatin as control

| Compound | IC$_{50}$ (μM) |
|---|---|
| [($\eta^5$-C$_5$Me$_5$)Ir(bipy)Cl]Cl (ZL04Cl) | >100 |
| [($\eta^5$-C$_5$Me$_4$C$_6$H$_5$)Ir(bipy)Cl]PF$_6$ (ZL37PF$_6$) | 15.9 |
| [($\eta^5$-C$_5$Me$_4$C$_6$H$_4$C$_6$H$_5$)Ir(bipy)Cl]PF$_6$ (ZL25PF$_6$) | 0.57 |
| [($\eta^5$-C$_5$Me$_5$)Ir(phen)Cl]Cl (ZL07Cl) | >100 |
| [($\eta^5$-C$_5$Me$_4$C$_6$H$_5$)Ir(phen)Cl]PF$_6$ (ZL33PF$_6$) | 6.7 |
| [($\eta^5$-C$_5$Me$_4$C$_6$H$_4$C$_6$H$_5$)Ir(phen)Cl]PF$_6$ (ZL54PF$_6$) | 0.72 |
| [($\eta^5$-C$_5$Me$_5$)IrCl(H$_2$NCH$_2$CH$_2$NH$_2$—N,N)]PF$_6$ (ZL01PF$_6$) | >100 |
| [($\eta^5$-C$_5$Me$_4$C$_6$H$_5$)IrCl(H$_2$NCH$_2$CH$_2$NH$_2$—N,N)]BPh$_4$ (ZL31BPh$_4$) | 17.0 |
| [($\eta^5$-C$_5$Me$_5$)Ir($\eta^2$—C$_5$H$_4$N-2-CO$_2$)Cl] (ZL03) | >100 |
| [($\eta^5$-C$_5$Me$_4$C$_6$H$_5$)Ir($\eta^2$—C$_5$H$_4$N-2-CO$_2$)Cl] (ZL38) | >100 |
| [($\eta^5$-C$_5$Me$_4$C$_6$H$_4$C$_6$H$_5$)Ir($\eta^2$—C$_5$H$_4$N-2-CO$_2$)Cl] (ZL43) | 16.3 |
| [($\eta^5$-C$_5$Me$_5$)Ir(acac)Cl] (ZL02) | >100 |
| [($\eta^5$-C$_5$Me$_5$)Ir(bipy(OH)O)Cl] (ZL44) | 17.2 |
| [($\eta^5$-C$_5$Me$_4$C$_6$H$_5$)Ir(bipy(OH)$_2$)Cl]PF$_6$ (ZL45) | 7.2 |
| {($\eta^5$-C$_5$Me$_4$C$_6$H$_4$C$_6$H$_5$)Ir[bipy(OH)(O)]Cl} (ZL46) | 2.8 |
| [($\eta^5$-C$_5$Me$_4$)Ir(2-phpy)Cl] (ZL47) | 10.8 |
| [($\eta^5$-C$_5$Me$_4$C$_6$H$_4$C$_6$H$_5$)Ir(2-phpy)Cl] (ZL49) | 0.70 |

TABLE 5-continued

In vitro growth inhibition of A2780 cancer cell lines for compounds ZL01-ZL04, ZL07, ZL25, ZL31, ZL33, ZL37, ZL38, ZL43, ZL54, ZL44-ZL47, ZL49, ZL51, ZL55, ZL57 and ZL59 and cisplatin as control

| Compound | IC$_{50}$ (μM) |
|---|---|
| [($\eta^5$-C$_5$Me$_5$)Ir{C$_6$H$_4$-2-C(H)=NPh-κC,N}Cl] (ZL51) | 5.0 |
| [($\eta^5$-C$_5$Me$_5$)Ir(bipy(Me)$_2$)Cl]PF$_6$ (ZL55PF$_6$) | >100 |
| [($\eta^5$-C$_5$Me$_4$C$_6$H$_5$)Ir(bipy(Me)$_2$)Cl]PF$_6$ (ZL57PF$_6$) | 9.2 |
| [($\eta^5$-C$_5$Me$_4$C$_6$H$_4$C$_6$H$_5$)Ir(bipy(Me)$_2$)Cl]PF$_6$ (ZL59PF$_6$) | 0.51 |
| Cisplatin | 1.2 |

The IC$_{50}$ values (concentration at which 50% of the cell growth is inhibited) of complexes ZL01-ZL04, ZL07 and ZL55, which only have Cp*, and complex ZL38, are all >100 μM and then can be described as inactive compounds. Compounds ZL25, ZL54, ZL49 and ZL59 containing Cp$^{xbiph}$, however, exhibited promising toxicity with IC$_{50}$ values ca. 2 times smaller than cisplatin. Those complexes containing Cp$^{xph}$ normally show moderate activity, ca. 10 times less active than cisplatin. So the cytotoxic activity of iridium complexes increases with the number of phenyl ring.

Interestingly, complexes ZL47, ZL51 and ZL44 containing Cp* ring and C,N-chelating ligands or diol ligand showed moderate or high activity, but the activity difference between complexes ZL49 containing Cp$^{xbiph}$ and ZL47 containing Cp* or between ZL46 and ZL44 is small like the difference between complex ZL25 and ZL04.

The cytotoxicity of complexes ZL07, ZL33, ZL38 and ZL54 toward SW480, A549 and CH1 cancer cell lines was investigated (Table 6). Complex ZL38 is still nontoxic to the highest test concentration (130 μM) towards all these three cell lines, while complex 7 shows moderate activity against SW480 and CH1. Complex ZL33 possesses promising cytotoxicity towards all the three cell lines, especially towards SW480 cell line, ca. 6.5 times more active than cisplatin. Complex ZL54 is still the most potent one of the four complexes, about 6.7 and 3.7 times more active than cisplatin against SW480 and A549 cell lines, respectively.

TABLE 6

In vitro growth inhibition of A549, SW480 and CH1 cancer cell lines for compounds ZL07, ZL33, ZL38 and ZL54, and cisplatin as control[a,b]

| Compound | A549 IC$_{50}$ (μM) | SW480 IC$_{50}$ (μM) | CH1 IC$_{50}$ (μM) |
|---|---|---|---|
| ZL07 | >130 | 80.08 ± 1.5 | 50.73 ± 2.8 |
| ZL33 | 11.48 ± 2.4 | 1.41 ± 0.2 | 1.32 ± 0.3 |
| ZL54 | 1.58 ± 0.4 | 1.38 ± 0.2 | 0.69 ± 0.04 |
| ZL38 | >130 | >130 | >130 |
| cisplatin | 5.9 ± 1.9 | 9.24 ± 1.1 | 0.59 ± 0.1 |

Conclusions

Organometallic [($\eta^5$-Cp$^x$)Ir(LL)Cl]$^{0/+}$ (Cp$^x$=Cp*, Cp$^{xph}$ and Cp$^{xbiph}$) complexes have potential for discovery as anticancer complexes and their IC$_{50}$ values are highly dependent on substitution on the Cp* ring in the order Cp$^{xbiph}$>Cp$^{xph}$>Cp*.

It has been found that the size of the substituents on the Cp* backbone plays a major role in the biological activity of these types of complexes. In several cases, the change from Cp* to Cp$^{xbiph}$ increases cytotoxicity by two orders of magnitude. The increase in activity with increased hydrophobicity of the arene might indicate that the arene is involved in increased cellular uptake, and in addition might be involved in the increased ability of substituted arenes to intercalate with the main target DNA induced by arene-purine hydrophobic stacking interactions.[19] Furthermore, the nature of the arene also has large influence on the rate and extent of hydrolysis, the $pK_a$ value of relevant aqua species.

In this work, several different types of chelating ligands, i.e. N,N—, N,O—, C,N— and O,O— are used to tune the biological activity of organometallic iridium complexes. The chelating ligand L-L' can not only help to control the stability and the ligand exchange rates of these complexes, but also may have an enormous effect on the reactivity in these types of complexes. When we change L-L' from a neutral 2,2'-bipyridine to an anionic picolinate (pico), the rate and extent of hydrolysis is greatly increased. Furthermore, a considerable increase in the $pK_a$ of the resulting aqua adduct from 6.28 to 7.62 (when $Cp^x$ is $Cp^{xph}$) is observed caused by the increased density of electronic charge on the iridium metal centre. The chelating ligand also determines the rate of binding to nucleobases and even changes the nucleobase selectivity.

This work shows that the changing of substituents on the Cp* backbone and chelating ligands can have significant effects on the aqueous chemistry of iridium(III) compounds of the type $[(\eta^5-Cp^x)Ir(LL')Cl]^{0/+}$ allowing a great scope to introduce desirable features into these types of complexes to optimize their design as anticancer drugs.

Further Rhodium Complexes and Data
Methods and Instrumentation $^1$H NMR spectra were acquired on a Bruker 300, 400 or 500 MHz spectrometer. $^1$H NMR chemical shifts were internally referenced to dimethyl sulfoxide (2.52 ppm), methanol (3.31 ppm) or chloroform (7.26 ppm).

CHN analysis was performed by Warwick Analytical Service using a CE440 Elemenial Analyser.

Positive ion electrospray mass spectrometry was performed on a Bruker Daltonics Esquire 2000 mass spectrometer at the University of Warwick. All samples were prepared in methanol.

Cytotoxicity testing in A2780 human ovarian cancer cells was performed by Dr Ana Maria Pizarro Arranz at the University of Warwick.

Materials

All deuterated solvents were obtained from Sigma-Aldrich and Cambridge Isotope Labs Inc. Phenyllithium in dibutyl ether 1.8 M, 2,3,4,5-tetramethyl-2-cyclopentanone, 4-bromo-biphenyl, n-Butillithium in hexane 1,6 M, 2,2'-bipyridyl, 4,4'-dimethyl-2,2'-dipyridyne, phenantroline, 2-phenylpyridine were obtained from Sigma-Aldrich. Magnesium sulphate and hydrochloric acid were obtained from Fisher Scientific. All dried solvents were obtained from sigma-aldrich, All non dried solvents used in synthesis were obtained from Fisher Scientific and Prolabo suppliers. $Rh(III)Cl_3 \times n\ H_2O$ was from Precious Metals Online.

Solvents were used as obtained, except in the case of methanol, which was degassed prior to use by bubbling with nitrogen.

Synthesis
3-Phenyl-1,2,4,5-tetramethyl-1,3-cyclopentadiene ($Cp^xPh$)

A solution of phenyllithium in dibutyl ether 1.8 M (50 mL, 90 mmol) was added to a solution of 2,3,4,5-tetramethyl-2-cyclopentanone (12 mL, 79.62 mmol)) at 273 K. The reaction mixture was allowed to warm slowly to 298 k with stirring overnight. The orange solution was cooled down by addition of ice and then acidified to reach pH 2 with HCl (36%). The solution was placed in a separating funnel and extracted with diethyl ether (3×50 mL). The combined organic portions were dried over anhydrous magnesium sulphate, filtered, and the solvents evaporated to dryness on a rotary evaporator to obtain a yellowish oil. The product was purified by distillation under vacuum (P: 0.5 mbar, T: 417 K)

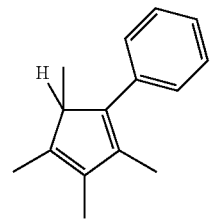

Yield: 91.7% (15.79 g)
$^1$H NMR (400 MHz, CDCl$_3$):
δ 7.362 ppm (m, 2H), 7.2513 ppm
(m, 2H), 7.199 ppm (m, 1H), 3.213 ppm
(m, 1H), 2.0433 ppm (d, 3H, J = 1.52 Hz),
1.945 ppm (m, 3H), 1.880 ppm (m, 3H),
0.968 ppm (d, 3H, J = 7.62 Hz)

3-Biphenyl-1,2,4,5-tetramethyl-1,3-cyclopentadiene ($Cp^x$-diPh)

A solution of 4-bromo-biphenyl (16 mg, 68.64 mmol) in dry THF (400 mL) was treated with a solution of n-butyl-lithium in hexane 1,6 M (50 mL, 80 mmol) at 195 K. After reacting for 3 h at 195 K, 2,3,4,5-tetramethyl-2-cyclopentanone (12 mL, 79.62 mmol) was added. The solution was allowed to warm slowly to 298 K with stirring overnight. The orange solution was acidified to pH 2 with HCl (36%) and placed in a separating funnel, the organic layer was collected and the remaining aqueous layer extracted with diethyl ether (3×50 mL). The combined organic portions were dried over anhydrous magnesium sulphate, filtered, and the solvent evaporated to dryness on a rotary evaporator to afford a dark yellow oily powder. The product was washed with methanol (3×20 mL) to give a yellowish powder.

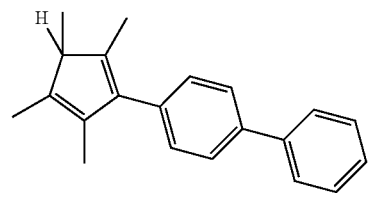

Yield: 94.38% (14.13 g)
$^1$H NMR (400 MHz, CDCl$_3$):
δ 7.639 ppm (d, 2H, J = 7.4 Hz), 7.608 ppm
(d, 2H, J = 8.28 Hz) 7.448 ppm (t, 2H, J =
7.5 Hz), 7.338 ppm (m, 3H), 3.249 ppm
(q, 1H, J = 7.66 Hz), 2.094 ppm
(d, 3H, J = 1.38 Hz), 1.962 ppm (s, 3H),
1.894 ppm (s, 3H), 1.012 ppm
(d, 3H, J = 7.66 Hz)

[(Cp*)RhCl$_2$]$_2$

Rhodium(III) trichloride (500 mg, 2.12 mmol) and 2,4-pentamethylcyclopentadiene (302 mg, 2.22 mmol) were placed in a 100 mL Schlenk flask and dissolved in dry methanol (50 mL). The solution was heated under reflux (343 K) in a nitrogen atmosphere for 48 h. The dark red precipitate obtained was filtered off, washed with ether and dried under vacuum.

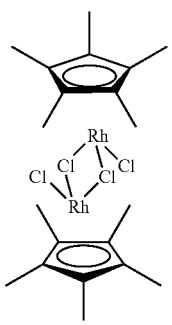

Yield: 62.69% (410.6 mg)
$^1$H NMR (400 MHz, DMSO-d$_6$): δ 1.627 ppm (s, 10H).

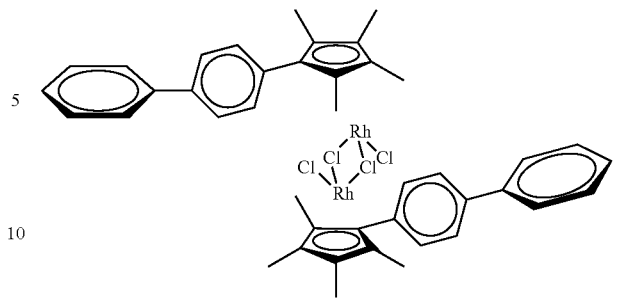

Yield: 32.34% (613.4 mg)
$^1$H NMR (400 MHz, DMSO-d$_6$):
δ 7.747 ppm (m, 12H), 7.491 ppm
(t, 4H, J = 7.42 Hz), 7.400 ppm
(t, 2H, J = 7.42 Hz), 1.725 ppm

[(Cp$^x$Ph)RhCl$_2$]$_2$

Rhodium(III) trichloride (100 mg, 0.42 mmol) and 3-phenyl-1,2,4,5-tetramethyl-1,3-cyclopentadiene (104.5 mg, 0.53 mmol) were placed in a 100 mL Schlenk flask and dissolved in dry methanol (50 mL). The solution was heated under reflux (343 K) in a nitrogen atmosphere for 48 h. The red precipitate obtained was filtered off, washed with ether and dried under vacuum.

[(Cp*)Rh(Phenanthroline)Cl]Cl (JS35)

[(Cp*)RuCl$_2$]$_2$ (50.2 mg, 0.081 mmol) and phenanthroline (32.2 mg, 0.162 mmol) were placed in a round bottom flask, dissolved in dichloromethane (25 mL) and stirred for 16 hours. The solvent was evaporated to dryness on rotary evaporator and the yellow powder re-dissolved in deionised water and filtered to remove impurities and lyophilised to give a yellowish powder.

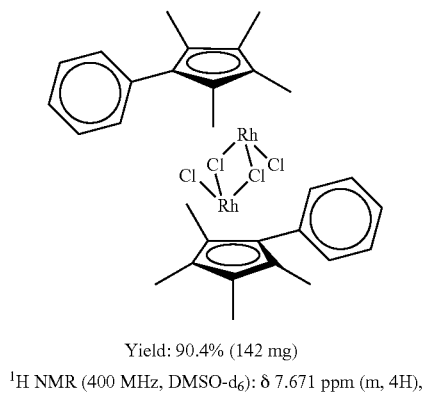

Yield: 90.4% (142 mg)
$^1$H NMR (400 MHz, DMSO-d$_6$): δ 7.671 ppm (m, 4H),
7.432 ppm (m, 6H), 1.707 ppm (s, 4H), 1.671 ppm
(m, 4H).

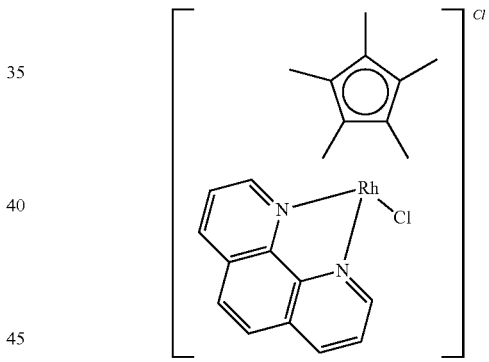

Yield: 96.1% (76.5 mg)
ESI-MS: (M—Cl)$^+$ 453.0 m/z
$^1$H NMR (400 MHz, MeOD-d$_4$): δ, 9.395 ppm
(d, 2H, J = 5.19 Hz), 8.873 ppm (d, 2H, J = 8.20 Hz),
8.243 ppm (s, 2H), 8.192 ppm (dd, 2H, J =
8.20, 5.19 Hz), 1.809 ppm (s, 2H), 1.792 ppm
(s, 6H).

[(Cp$^x$diPh)RhCl$_2$]$_2$

Rhodium(III) trichloride (1 g, 4.20 mmol) was dissolved in dry methanol (150 mL) in a 250 mL Schlenk tube. The solution was heated under reflux (343 K) in a nitrogen atmosphere with 3-biphenyl-1,2,4,5-tetramethyl-1,3-cyclopentadiene (923 mg, 4.40 mmol) for 48 h. The red-orange precipitate obtained was filtered off, washed with ether and dried under vacuum.

[(Cp*)Rh(2-phenylbipyridyl)Cl]Cl (JS36)

[(Cp*)RuCl$_2$]$_2$ (46.6 mg, 0.08 mmol) and sodium acetate (42.2 mg, 0.51.4 mmol) were dissolved in dichloromethane (25 mL) and placed in a 50 mL round bottom flask. 2-phenylpyridine (25.4 µL, 0.176 mmol) was added and the solution stirred at ambient temperature for 16 h under nitrogen atmosphere. The orange solution was filtered through celite and the solvent evaporated to dryness on the rotary evaporator to give an orange powder after washing with hexane.

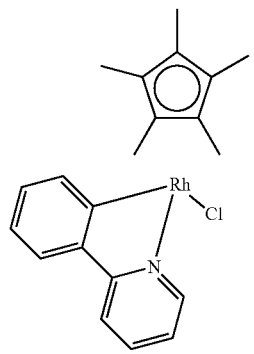

Yield: 88.6% (57.3 mg)
Elem. Anal. Calc: C, 58.96; H, 5.42; N, 3.27;
found: C, 47.62; H, 5.18; N, 3.01
ESI-MS: (M—HCl) 392.1 m/z
$^1$H NMR (400 MHz, CDCl$_3$): δ 8.747 ppm (d, 1H, J = 5.79 Hz), 8.817 ppm (d, 1H, J = 7.62 Hz), 7.776 ppm (d, 1H, J = 7.79 Hz), 7.713 ppm (t, 1H, J = 7.79 Hz), 7.609 ppm (d, 1H, J = 7.62 Hz), 7.248 ppm (t, 3H, J = 7.45 Hz), 7.133 ppm (t, 1H, J = 6.58 Hz), 7.064 ppm (t, 1H, J = 7.45 Hz), 1.631 ppm (s, 15H)

[(Cp$^x$Ph)Rh(4,4'-dimethyl-2,2'-dipyridyl)Cl]Cl (JS27)

A solution of [(Cp$^x$Ph)RuCl$_2$]$_2$ (51.7 mg, 0.070 mmol) in dichloromethane (25 mL) was placed in a 50 mL round bottom flask. After addition of 4,4'-dimethyl-2,2'-dipyridine (24.9 mg, 0,137 mmol) the solution was stirred for 16 hours. The solvent was evaporated to dryness on rotary evaporator and the yellow powder recrystallised form methanol/ether (2:1) to give a yellowish powder.

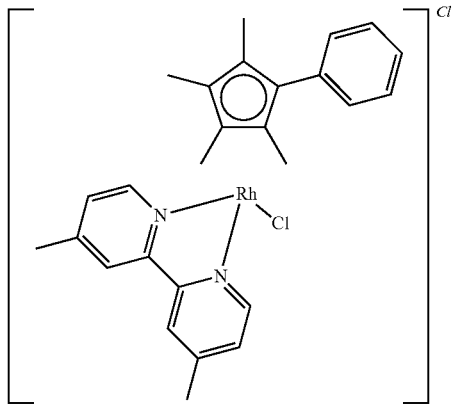

Yield: 87.8% (68.1 mg)
ESI-MS: (M—Cl) 519.0 m/z
$^1$H NMR (400 MHz, CDCl$_3$): δ 8.867 ppm (s, 2H), 8.257 ppm (d, 2H, J = 7.76 Hz), 7.681 ppm (m, 2H), 7.562 ppm (m, 3H), 7.399 ppm (d, 2H, J = 5.76 Hz), 2.646 ppm (s, 6H), 1.843 ppm (s, 6H), 1.761 ppm (s, 6H).

[(Cp$^x$Ph)Rh(Phenanthroline)Cl]Cl (JS28)

[(Cp$^x$Ph)RuCl$_2$]$_2$ (49.3 mg, 0.066 mmol) and phenanthroline (26.1 mg, 0.132 mmol) were placed in a round bottom flask, dissolved in dichloromethane (25 mL) and stirred for 16 hours at ambient temperature. The solvent was evaporated to dryness on rotary evaporator and the yellow powder dissolved in deionised water, filtered to remove impurities and lyophilised to give a yellowish powder

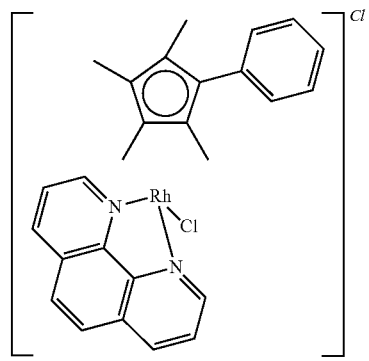

Yield: 99.2% (72.8 mg)
ESI-MS: (M—Cl) 515.0 m/z
$^1$H NMR (400 MHz, CDCl$_3$): δ 9.076 ppm (d, 1H, J = 5.15 Hz), 8.691 ppm (d, 2H, J = 8.13 Hz), 8.125 ppm (m, 2H), 7.784 ppm (m, 2H), 7.602 ppm (m, 2H), 2.060 ppm (s, 6H), 1.846 ppm (s, 6H).

[(Cp$^x$Ph)Rh(2-Phenylbipyridyl)Cl]Cl (JS 29)

[(Cp$^x$Ph)RuCl$_2$]$_2$ (49.6 mg, 0.067 mmol) and sodium acetate (33.6 mg, 0.40 mmol) were dissolved in dichloromethane (25 mL) and placed in a 50 mL round bottom flask. 2-phenylpyridine (22.0 μL, 0.154 mmol) was added and the solution stirred at ambient temperature for 16 h under nitrogen atmosphere. The orange solution was filtered through celite and the solvent evaporated to dryness on the rotary evaporator to give an orange powder after washing with ether.

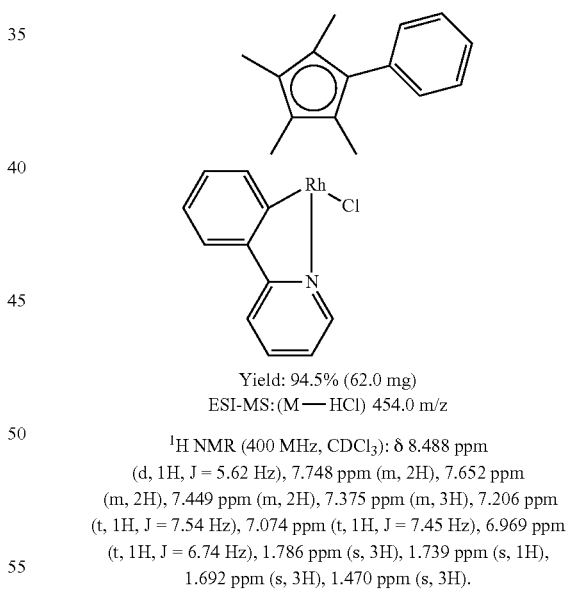

Yield: 94.5% (62.0 mg)
ESI-MS: (M—HCl) 454.0 m/z
$^1$H NMR (400 MHz, CDCl$_3$): δ 8.488 ppm (d, 1H, J = 5.62 Hz), 7.748 ppm (m, 2H), 7.652 ppm (m, 2H), 7.449 ppm (m, 2H), 7.375 ppm (m, 3H), 7.206 ppm (t, 1H, J = 7.54 Hz), 7.074 ppm (t, 1H, J = 7.45 Hz), 6.969 ppm (t, 1H, J = 6.74 Hz), 1.786 ppm (s, 3H), 1.739 ppm (s, 1H), 1.692 ppm (s, 3H), 1.470 ppm (s, 3H).

[(Cp$^x$diPh)Rh(acetylacetonate)Cl]Cl (JS31)

A solution of [(Cp$^x$Ph)RuCl$_2$]$_2$ (46.6 mg, 0.08 mmol) in acetone (25 mL) was placed in a 50 mL round bottom flask. After addition of sodium acetylacetonate (30 mg, 0,165 mmol) the solution was stirred for 48 hours at ambient temperature. The solvent was evaporated to dryness on rotary evaporator. The orange oil was dissolved in dichloromethane, filtered through celite and the solvent evaporated to dryness in the rotary evaporator to give an orange oil. A dark red powder was obtained after washing with ether (3×10 mL).

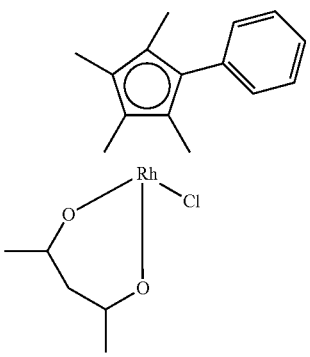

Yield: 80.4% (22 mg)
Elem. Anal. Calc: C, 55.25;
H, 5.56; found: C, 55.50; H, 5.66
ESI-MS: (M—HCl) 399.1 m/z ¹H NMR (300 MHz, CDCl₃): δ 7.481 ppm
(m, 2H), 7.396 ppm (m, 3H), 5.170 ppm (s, 1H),
2.008 ppm (m, 6H), 1.769 ppm (m, 6H), 1.581 ppm (s, 5H).

[(Cp$^x$diPh)Rh(2,2'-dipyridyl)Cl]Cl (JS20)

[(Cp$^x$biPh)RuCl₂]₂ (51 mg, 0.057 mmol) and 2,2'-dipyridine (18.4 mg, 0.118 mmol) were dissolved in dichloromethane (25 mL) and stirred for 16 h at ambient temperature. The yellow solution was evaporated to dryness on the rotary evaporator and the product obtained recrystallised from methanol/ether (2:1) to give a yellowish powder.

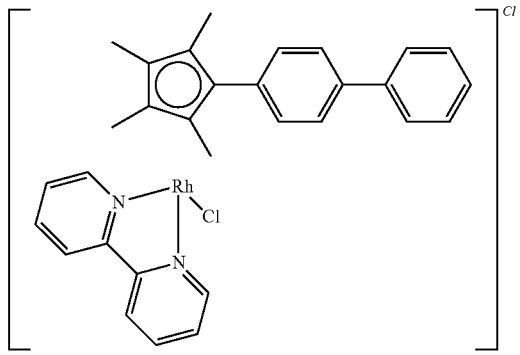

Yield: 63.1% (43.4 mg)
ESI-MS: (M—Cl) 567.0 m/z

¹H NMR (400 MHz, CDCl₃): ? ? 9.165 ppm
(d, 2H, J = 8.05 Hz), 8.584 ppm (d, 2H, J = 5.34 Hz), 8.250 ppm
(td, 2H, J = 7.71, 1.19 Hz), 7.748 ppm (d, 2H, J = 8.60 Hz), 7.790 ppm
(d, 2H, J = 8.60 Hz), 7.681 ppm (d, 2H, J = 7.36 Hz), 7.641 ppm
(td, 2H, J = 6.63, 0.89 Hz), 7.520 ppm (t, 2H, J = 7.36 Hz),
7.445 ppm (t, 2H, J = 7.36 Hz), 1.863 ppm (s, 6H), 1.815 ppm (s, 6H).

[(Cp$^x$diPh)Rh(4,4'-dimethyl-2,2'-dipyridyl)Cl]Cl (JS22)

A solution of [(Cp$^x$diPh)RuCl₂]₂ (49.6 mg, 0.055 mmol) in dichloromethane (25 mL) was placed in a 50 mL round bottom flask. After addition of 4,4'-dimethyl-2,2'-dipyridine (30 mg, 0,165 mmol) the solution was stirred for 16 hours at ambient temperature. The solvent was evaporated to dryness on the rotary evaporator and the yellow powder obtained recrystallised from methanol/ether (2:1) to give a dark yellow powder.

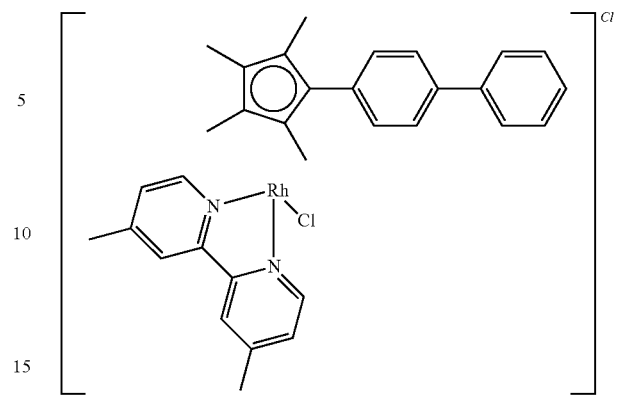

Yield: 76.5% (53.4 mg)
ESI-MS: (M—Cl) 595.1 m/z

¹H NMR (400 MHz, CDCl₃): δ 8.873 ppm (s, 2H), 8.400 ppm
(d, 2H, J = 5.95 Hz), 7.768 ppm (d, 4H, J = 2.42 Hz), 7.680 ppm
(d, 2H, J = 7.44), 7.519 ppm (t, 2H, J = 7.44 Hz), 7.452 ppm (d, 1H, J = 7.26 Hz), 7.417 ppm (d, 2H, J = 5.95 Hz), 2.652 ppm
(s, 6H), 1.862 ppm (s, 6H), 1.808 ppm (s, 6H).

[(Cp$^x$diPh)Rh(Phenanthroline)Cl]Cl (JS21)

[(Cp$^x$BiPh)RuCl₂]₂ (49.4 mg, 0.055 mmol) and phenanthroline (22.4 mg, 0.113 mmol) were placed in a round bottom flask, dissolved in dichloromethane (25 mL) and stirred for 16 hours at ambient temperature. The solvent was evaporated to dryness on rotary evaporator and the product recrystallised from methanol to give a yellow powder.

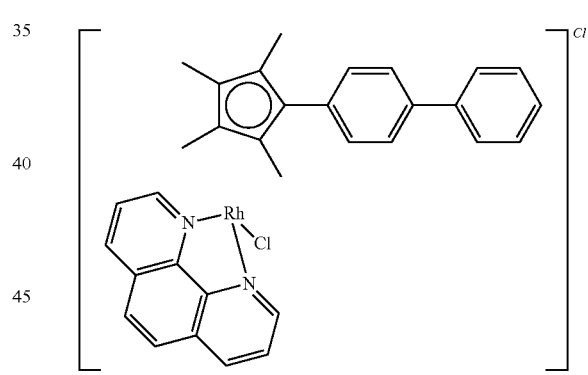

Yield: 89.7% (62.1 mg)
ESI-MS: (M—Cl) 531.1 m/z

¹H NMR (400 MHz, CDCl₃): δ 9.096 ppm
(d, 2H, J = 8.37 Hz), 8.702 ppm (d, 2H, J = 8.37 Hz), 8.120 ppm
(m, 4H), 7.856 ppm (d, 2H, J = 8.08 Hz), 7.810 ppm (d, 2H, J = 8.08 Hz),
7.705 ppm (d, 2H, J = 7.51 Hz), 7.527 ppm
(t, 2H, J = 7.51 Hz), 7.449 ppm (t, 2H, J = 7.51 Hz), 2.049 ppm (s, 6H),
1.879 ppm (s, 8H)

[(Cp$^x$diPh)Rh(2-phenylbipyridyl)Cl]Cl JS39)

[(Cp$^x$BiPh)RuCl₂]₂ (50.6 mg, 0.056 mmol) and sodium acetate (27.5 mg, 0.335 mmol) were dissolved in dichloromethane (25 mL) and placed in a 50 mL round bottom flask. 2-phenylpyridine (17.5 ηL, 0.123 mmol) was added and the solution stirred at ambient temperature for 16 h under nitrogen atmosphere. The orange solution was filtered through celite and the solvent evaporated to dryness on the rotary evaporator to give an orange powder after washing with ether.

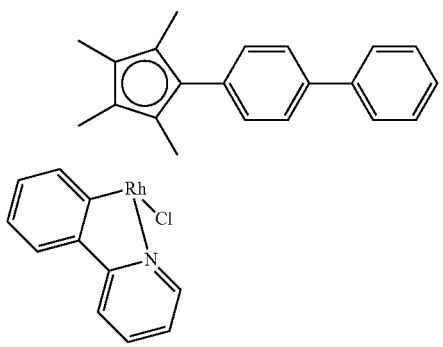

Yield: 43.4% (27.8mg)
ESI-MS: (M—HCl) 530.1 m/z $^1$H NMR (400 MHz, CDCl$_3$): δ 8.529 ppm (d, 1H, J = 5.67 Hz), 7.994 ppm (dd, 1H, J = 7.16, 1.35 Hz), 7.765 ppm (m, 2H), 7.639 ppm (m, 6H), 7.522 ppm (d, 2H, J = 8.17 Hz), 7.468 ppm (m, 3H), 7.371 ppm (t, 1H, J = 7.45 Hz), 7.219 ppm (m, 1H), 7.084 ppm (m, 1H), 6.986 ppm (m, 1H), 1.827 ppm (s, 3H), 1.517 ppm (s, 3H), 1.707 ppm (s, 3H), 1.754 ppm (s, 3H).

[(Cp*)Rh(4-(2-pyridylazo)N,N-dimethylaniline)Cl]PF$_6$ (JS43)

[(Cp*)RuCl$_2$]$_2$ (50.6 mg, 0.082 mmol), 4-(2-pyridylazo)N,N-dimethylaniline (36.5 mg, 0.161 mmol) and ammonium hexafluorophosphate (33.96 mg, 0.202 mmol) were placed in a 50 mL round bottom flask covered with aluminium foil, dissolved in methanol (25 mL) and stirred for 16 hours at ambient temperature. A blackish-blue precipitate was collected by filtration from the solution and recrystallised from methanol to give greenish crystals.

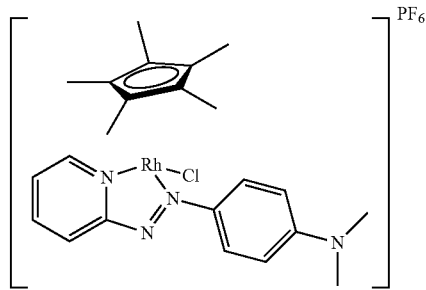

Yield: 13.94% (14.5 mg)

$^1$H NMR (500 MHz, DMSO-d$_6$): δ 8.551 ppm (d, 1H, J = 5.53 Hz), 8.337 ppm (m, 2H), 8.064 ppm (d, 2H, J = 9.37 Hz), 7.753 ppm (t, 1H, J = 6.25 Hz), 7.062 ppm (d, 2H, J = 9.37 Hz), 3.284 ppm (s, 6H), 1.553 ppm (s, 15H).

[(Cp$^x$Ph)Rh(4-(2-pyridylazo)N,N-dimethylaniline)Cl]PF$_6$ (JS44)

[(Cp$^x$Ph)RuCl$_2$]$_2$ (50.1 mg, 0.068 mmol), 4-(2-pyridylazo)N,N-dimethylaniline (30.1 mg, 0.133 mmol) and ammonium hexafluorophosphate (29.1 mg, 0.173 mmol) were dissolved in methanol (25 mL) and stirred for 16 hours at ambient temperature in the dark. A -blackish-blue precipitate was collected by filtration and recrystallised from methanol to give a blueish crystals.

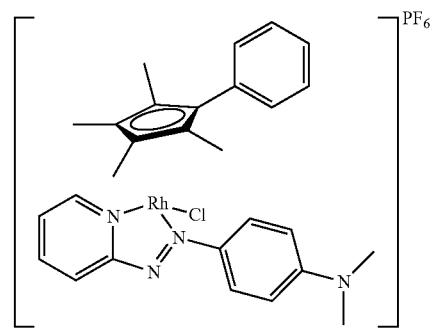

Yield: 25.63% (24.1 mg)

$^1$H NMR (500 MHz, DMSO-d$_6$): δ 8.557 ppm (d, 1H, J = 5.28 Hz), 8.375 ppm (d, 1H, J = 7.61 Hz), 8.309 ppm (t, 1H, J = 7.45 Hz), 8.042 ppm (t, 2H, J = 9.16 Hz), 7.672 ppm (t, 1H, J = 6.36 Hz), 7.511 ppm (d, 1H, J = 7.14 Hz), 7.473 ppm (t, 2H, J = 6.83 Hz) 7.405 ppm (d, 2H, J = 6.83 Hz), 6.889 ppm (d, 2H, J = 9.31 Hz). 1.740 ppm (s, 6H), 1.678 ppm (s, 3H), 1.658 (s, 3H), 1.469 ppm (s, 3H).

[(Cp$^x$BiPh)Rh(4-(2-pyridylazo)N,N-dimethylaniline)Cl]PF$_6$ (JS45)

[(Cp$^x$BiPh)RuCl$_2$]$_2$ (49.8 mg, 0.056 mmol), 4-(2-pyridylazo)N,N-dimethylaniline (25.24 mg, 0.112 mmol) and ammonium hexafluorophosphate (24.7 mg, 0.147 mmol) were dissolved in methanol (25 mL) and stirred for 16 hours at ambient temperature in the dark. A blackish-blue precipitate was collected by filtration from the solution and recrystallised in methanol to give a dark blue powder.

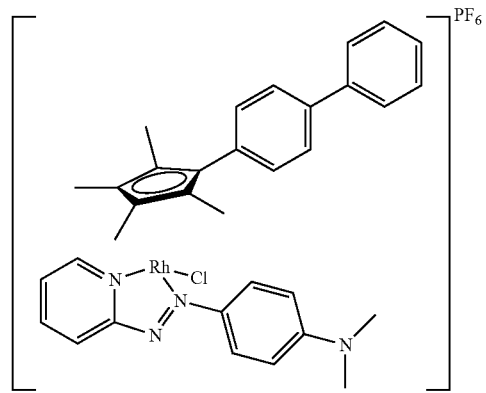

Yield: 91.9% (80.3 mg)

$^1$H NMR (500 MHz, DMSO-d$_6$): δ 8.629 ppm (d, 1H, J = 4.61 Hz), 8.383 ppm (d, 1H, J = 7.94 Hz), 8.317 ppm (dt, 1H, J = 7.44, 1.35 Hz), 8.051 ppm (d, 2H, J = 9.57 Hz), 7.779 ppm (d, 2H, J = 8.25 Hz), 7.744 ppm (d, 2H, J = 7.26 Hz), 7.696 ppm (t, 2H, J = 6.27 Hz), 7.508 ppm (m, 4H), 7.424 ppm (t, 1H, J = 7.59 Hz). 6.861 ppm (d, 2H, J = 9.57 Hz), 3.195 ppm (s, 6H), 1.756 ppm (s, 3H), 1.683 ppm (s, 3H), 1.679 ppm (s, 3H), 1.572 ppm (s, 3H).

[(Cp*)Rh(1,4-BenzenediamineN1,N1-dimethyl-N4-(2-pyridinylmethylene)Cl]PF$_6$ (JS46)

[(Cp*)RuCl$_2$]$_2$ (38.0 mg, 0.062 mmol), 1,4-benzenediamineN1,N1-dimethyl-N4-(2-pyridinylmethylene) (28.1 mg, 0.125 mmol) were placed in a 50 mL round bottom flask, dissolved in methanol (25 mL) and stirred for 2 hours at ambient temperature. After reducing the volume ammonium hexafluorophosphate (33.96 mg, 0.202 mmol) was added to give a reddish-brown precipitate.

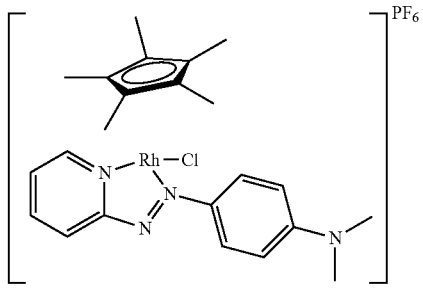

Yield: 93.85% (74.3 mg)

$^1$H NMR (500 MHz, DMSO-d$_6$): δ 8.998 ppm (d, 1H, J = 5.46 Hz), 8.7994 ppm (s, 1H), 8.318 ppm (td, 1H, J = 7.41, 1.17 Hz), 8.216 ppm (d, 1H, J = 7.41 Hz), 7.890 ppm (t, 1H, J = 5.85 Hz), 7.619 ppm (d, 2H, J = 9.97 Hz), 6.877 ppm (d, 2H, J = 8.97 Hz), 3.026 ppm (s, 6H), 1.448 ppm (s, 15H).

[(Cp$^x$Ph)Rh(1,4-BenzenediamineN1,N1-dimethyl-N4-(2-pyridinylmethylene) Cl]PF$_6$ (JS47)

[(Cp$^x$Ph)RuCl$_2$]$_2$ (50.2 mg, 0.068 mmol), 1,4-benzenediamineN1,N1-dimethyl-N4-(2-pyridinylmethylene (31.3 mg, 0.139 mmol) were dissolved in methanol (25 mL) and stirred for 2 hours at 313 K. After reducing the volume ammonium hexafluorophosphate (28.5 mg, 0.170 mmol) was added to give a red crystals.

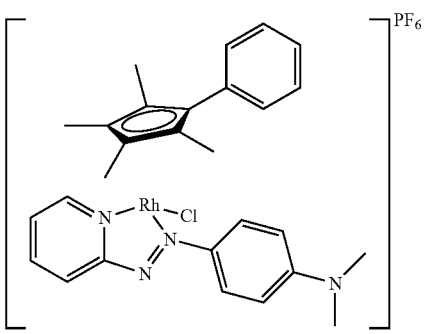

Yield: 95.49% (74.5 mg)

$^1$H NMR (500 MHz, DMSO-d$_6$): δ 8.846ppm (s, 1H), 8.585 ppm (d, 1H, J = 5.56 Hz), 8.2983 ppm (t, 1H, J = 7.88 Hz), 8.246 ppm (d, 1H, J = 6.49 Hz), 7.791 ppm (t, 1H, J = 6.02 Hz), 7.576 ppm (d, 2H, J = 9.27 Hz), 7.510 ppm (m, 4H) 6.780 ppm (d, 2H, J = 9.27 Hz), 2.992 ppm (s, 6H). 1.642 ppm (s, 3H), 1.568 ppm (s, 3H), 1.473 ppm (s, 3H), 1.304 ppm (s, 3H).

[(Cp$^x$BiPh)Rh(1,4-BenzenediamineN1,N1-dimethyl-N4-(2-pyridinylmethilene) Cl]PF$_6$ (JS48)

[(Cp$^x$BiPh)RuCl$_2$]$_2$ (45 mg, 0.050 mmol), 1,4-benzenediamineN1,N1-dimethyl-N4-(2-pyridinylmethylene (23.12 mg, 0.103 mmol) were placed in a 50 mL round bottom flask, dissolved in methanol (25 mL) and stirred for 2 hours at 313 K. After reducing the volume ammonium hexafluorophosphate (21.7 mg, 0.124 mmol) was added to obtain a reddish-brown powder

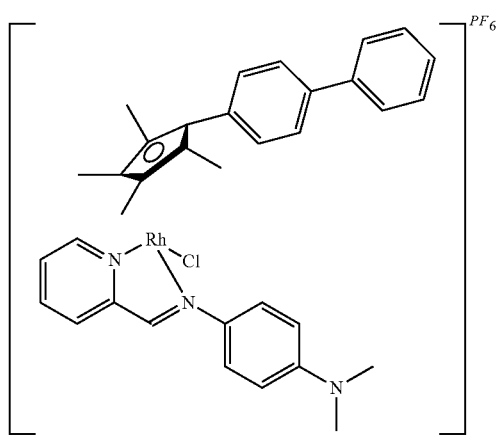

Yield: 71.83% (56.4 mg)

$^1$H NMR (500 MHz, DMSO-d$_6$): δ 8.848 ppm (s, 1H), 8.651 ppm (d, 1H, J = 5.40 Hz), 8.303 ppm (d, 1H, J = 7.77), 8.248 ppm (d, 1H, J = 7.60 Hz), 7.807 ppm (m, 3H), 7.759 ppm (d, 2H, J = 7.60 Hz), 7.622 ppm (d, 2H, J = 8.27 Hz), 7.583 ppm (d, 2H, J = 8.95 Hz), 7.510 ppm (t, 2H, J = 7.77 Hz), 7.425 ppm (t, 1H, J = 7.43 Hz), 6.753 ppm (d, 2H, J = 9.12 Hz), 2.959 ppm (s, 6H), 1.6593 ppm (s, 3H), 1.594 ppm (s, 3H), 1.461 ppm (s, 3H), 1.406 ppm (s, 3H).

Rhodium(III) Cp* and derivatives containing O,O—, N,N— and C,N— chelating ligands

TABLE 7

| Code | Structure | IC$_{50}$ (μM) | Purity[a] |
|---|---|---|---|
| JS31 | 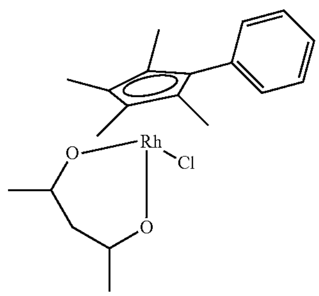 | $5 < IC_{50} < 50$ | MS, NMR |
| JS35 | 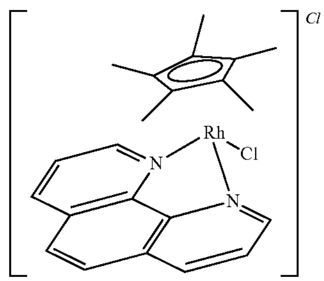 | $5 < IC_{50} < 50$ | MS, NMR |
| JS28 | 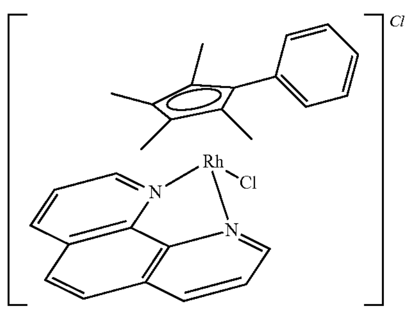 | $5 < IC_{50} < 50$ | MS, NMR |
| JS21 | 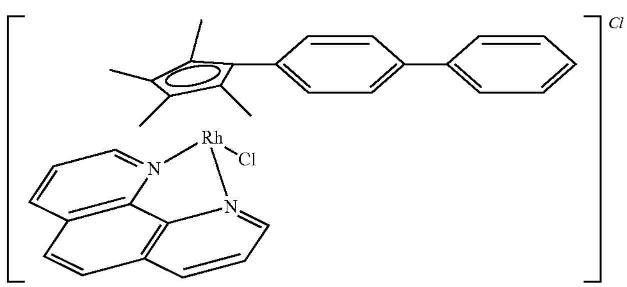 | $5 < IC_{50} < 50$ | MS, NMR |
| JS20 | 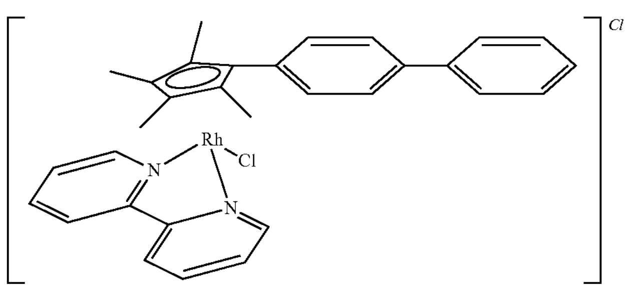 | $5 < IC_{50} < 100$ | MS, NMR |

TABLE 7-continued

Compounds active against A2780 human ovarian cancer cells

| Code | Structure | IC$_{50}$ (μM) | Purity[a] |
|---|---|---|---|
| JS34 | 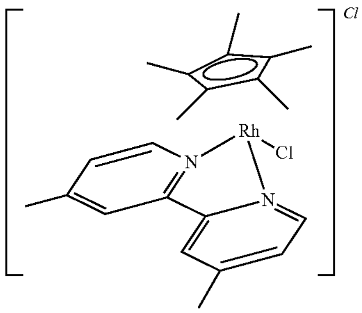 | 5 < IC$_{50}$ < 100 | MS, NMR |
| JS22 | 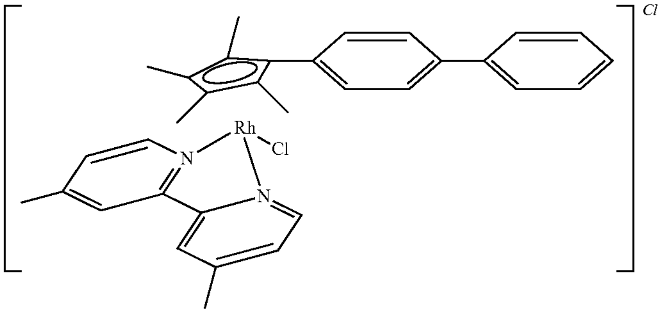 | 5 < IC$_{50}$ < 50 | MS, NMR |
| JS29 | 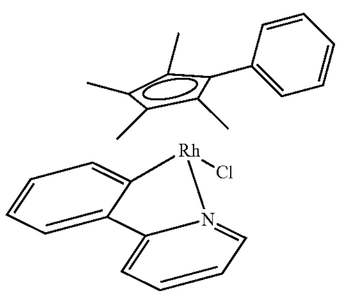 | 1.25 < IC$_{50}$ < 12.5 | MS, NMR |
| JS36 | 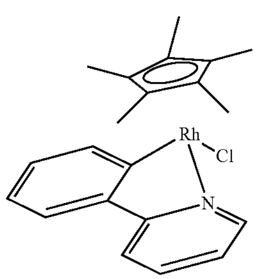 | 1.25 < IC$_{50}$ < 12.5 | MS, NMR |
| JS39 | 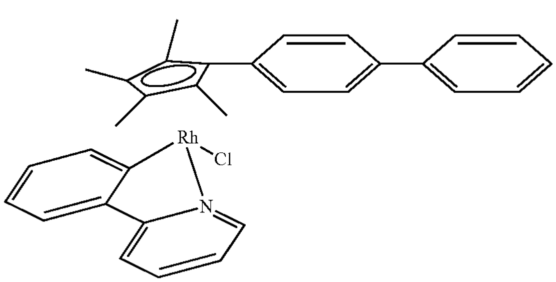 | 1.25 < IC$_{50}$ < 12.5 | MS, NMR |

[a]MS is mass spectrometry; NMR is $^1$H NMR spectroscopy
These show that all complexes are > 90% pure Comments
  Compounds with CN ligands (JS29, JS36, JS39) are the most active
  Complexes with phenylsubstituents on the Cp* ring are more active than Cp* complexes (e.g. J22 compared to JS34)

Further Iridium Complexes and Data

Materials. 2-phenylpyridine (2-phpy), 2-(2,4-difluorophenyl)pyridine (2-dfphpy), 2-(p-tolyl) pyridine (tpy), 2-phenylquinoline (2-phq), ammonium hexafluorophosphate, tetramethyl(n-propyl)cyclopentadiene, $IrCl_3 \cdot nH_2O$, 9-ethylguanine, pyridine and sodium acetate were purchased from Sigma-Aldrich. dipyrido[3,2f:2',3'-h]quinoxaline (dpq) and dipyrido[3,2-a:2',3'-c]phenazine (dppz) were prepared according to literature methods.[20] Methanol was distilled over magnesium/iodine prior to use.

Syntheses.

$[(\eta^5\text{-}C_5Me_5)Ir(azpy\text{-}NMe_2)Cl]PF_6$ (ZL64). A solution of $[(\eta^5\text{-}C_5Me_5)IrCl_2]_2$ (48 mg, 0.06 mmol), and ligand 4-(2-pyridylazo)-N,N-dimethylaniline (azpy-$NMe_2$, 27 mg, 0.12 mmol) in MeOH (20 mL) was stirred for 12 h at ambient temperature. The volume was slowly reduced to half on a rotary evaporator and $NH_4PF_6$ (45 mg, 0.28 mmol) was added. After standing at 277 K, a microcrystalline product formed. This was collected by filtration, washed with diethyl ether, and recrystallized from methanol/diethyl ether. Yield: 68 mg (77%). $^1$H NMR (DMSO-$d_6$): δ=8.82 (d, 1H, J=6.0 Hz), 8.51 (d, 1H, J=8.5 Hz), 8.28 (t, 1H, J=7.0 Hz), 8.02 (m, 2H), 7.76 (t, 1H, J=6.7 Hz), 7.02 (m, 2H), 3.31 (s, 6H), 1.55 (s, 15H). Anal. Calcd for $C_{23}H_{29}ClF_6IrN_4P$ (734.14): C, 37.63; H, 3.98; N, 7.63. Found: C, 37.41; H, 4.01; N, 7.76.

$[(\eta^5\text{-}C_5Me_4C_6H_5)Ir(azpy\text{-}NMe_2)Cl]PF_6$ (ZL109). The synthesis was performed as for ZL64 using $[(\eta^5\text{-}C_5Me_4C_6H_5)IrCl_2]_2$ (46 mg, 0.05 mmol), azpy-$NMe_2$ (23 mg, 0.10 mmol). Yield: 56 mg (70%). $^1$H NMR ($CDCl_3$): δ=8.34 (d, 1H, J=8.0 Hz), 8.25 (d, 1H, J=5.5 Hz), 8.11 (m, 2H), 8.03 (t, 1H, J=8.0 Hz), 7.47 (m, 5H), 7.13 (t, 1H, J=7.0 Hz), 6.65 (m, 2H), 3.31 (s, 6H), 1.75 (s, 3H), 1.69 (s, 3H), 1.65 (s, 3H), 1.49 (s, 3H). Anal. Calcd for $C_{28}H_{31}ClF_6IrN_4P$ (796.15): C, 42.24; H, 3.92; N, 7.04. Found: C, 42.32; H, 3.91; N, 7.16.

$[(\eta^5\text{-}C_5Me_4C_6H_5)Ir(pp\text{-}NMe_2)Cl]PF_6$ (ZL110). The synthesis was performed as for ZL64 using $[(\eta^5\text{-}C_5Me_4C_6H_5)IrCl_2]_2$ (46 mg, 0.05 mmol), pp-$NMe_2$ (23 mg, 0.10 mmol). Yield: 60 mg (75%). $^1$H NMR ($CDCl_3$): δ=8.77 (s, 1H), δ=8.21 (dd, 2H, J=10.0 Hz), 7.98 (t, 1H, J=8.2 Hz), 7.68 (d, 2H, 8.5 Hz), 7.52 (m, 5H), 7.38 (t, 1H, J=7.0 Hz), 6.71 (d, 2H, 8.7 Hz), 3.36 (s, 6H), 1.80 (s, 3H), 1.55 (s, 3H), 1.46 (s, 3H), 1.39 (s, 3H).

$[(\eta^5\text{-}C_5Me_5)Ir(2\text{-}phq)Cl]$ (ZL68). A solution of $[(\eta^5\text{-}C_5Me_5)IrCl_2]_2$ (48 mg, 0.06 mmol), 2-phenylquinoline (25 mg, 0.12 mmol), and sodium acetate (20 mg, 0.24 mmol) in $CH_2Cl_2$ (15 ml) was stirred for 2 h at ambient temperature. The solution was filtered through celite and rotary evaporated to dryness, then washed with diethyl ether. The product was crystallized from $CHCl_3$/hexane. Yield: 43 mg (75%). $^1$H NMR ($CDCl_3$): δ=8.71 (d, 1H, J=8.8 Hz), 8.02 (d, 1H, J=8.7 Hz), 7.93 (d, 2H, J=8.8 Hz), 7.77 (m, 2H), 7.69 (t, 1H, J=8.1 Hz), 7.53 (t, 1H, J=6.7 Hz), 7.24 (t, 1H, J=7.8 Hz), 7.07 (t, 1H, J=7.7 Hz), 1.57 (s, 15H). Anal. Calcd for $C_{25}H_{25}ClNIr$ (567.13): C, 52.94; H, 4.44; N, 2.47. Found: C, 53.06; H, 4.41; N, 2.42. Crystals suitable for X-ray diffraction were obtained by slow evaporation of a methanol/diethyl ether solution at ambient temperature.

$[(\eta^5\text{-}C_5Me_5)Ir(tpy)Cl]$ (ZL69). The synthesis was performed as for ZL68 using $[(\eta^5\text{-}C_5Me_5)IrCl_2]_2$ (48 mg, 0.06 mmol), 2-(p-tolyl)pyridine (20 mg, 0.12 mmol), and sodium acetate (20 mg, 0.24 mmol). Yield: 45 mg (70%). $^1$H NMR ($CDCl_3$): δ=8.65 (d, 1H, J=5.7 Hz), 7.75 (d, 1H, J=8.3 Hz), 7.62 (m, 2H), 7.57 (d, 1H, J=8.0 Hz), 7.03 (t, 1H, J=6.3 Hz), 6.86 (d, 1H, J=7.8 Hz), 1.68 (s, 15H). Anal. Calcd for $C_{22}H_{25}ClNIr$ (531.14): C, 49.75; H, 4.74; N, 2.64. Found: C, 49.66; H, 4.65; N, 2.68.

$[(\eta^5\text{-}C_5Me_5)Ir(2\text{-}dfphpy)Cl]$ (ZL74). The synthesis was performed as for ZL68 using $[(\eta^5\text{-}C_5Me_5)IrCl_2]_2$ (48 mg, 0.06 mmol), 2-(2,4-difluorophenyl)pyridine (23 mg, 0.12 mmol), and sodium acetate (20 mg, 0.24 mmol). Yield: 46 mg (70%). $^1$H NMR ($CDCl_3$): δ=8.71 (d, 1H, J=6.0 Hz), 8.19 (d, 1H, J=8.8 Hz), 7.69 (t, 1H, J=8.0 Hz), 7.31 (d, 1H, J=8.8 Hz), 7.10 (t, 1H, J=6.3 Hz), 6.49 (t, 1H, J=9.5 Hz), 1.67 (s, 15H). Anal. Calcd for $C_{21}H_{21}ClF_2NIr$ (553.10): C, 45.60; H, 3.83; N, 2.53. Found: C, 45.76; H, 3.71; N, 2.46.

$[(\eta^5\text{-}C_5Me_4C_6H_5)(2\text{-}phpy)Cl]$ (ZL107). A solution of $[(\eta^5\text{-}C_5Me_4C_6H_5)IrCl_2]_2$ (46 mg, 0.05 mmol), 2-phenylpyridine (15 mg, 0.10 mmol), and sodium acetate (16 mg, 0.20 mmol) in $CH_2Cl_2$ (15 ml) was heated under reflux in an $N_2$ atmosphere for 24 h. The solution was filtered through celite and rotary evaporated to dryness, then washed with diethyl ether. The product was crystallized from $CHCl_3$/hexane. Yield: 37 mg (57%). $^1$H NMR (MeOD-$d_4$): δ=8.60 (d, 1H, J=5.3 Hz), 8.04 (d, 1H, J=8.3 Hz), 7.84 (m, 2H), 7.65 (d, 1H, J=7.8 Hz), 7.38 (m, 3H), 7.33 (m, 2H), 7.16 (t, 1H, J=6.1 Hz), 7.13 (t, 1H, J=7.2 Hz), 7.09 (t, 1H, J=7.3 Hz), 1.85 (s, 3H), 1.74 (s, 3H), 1.72 (s, 3H), 1.56 (s, 3H). Anal. Calcd for $C_{26}H_{25}ClNIr$ (579.16): C, 53.92; H, 4.35; N, 2.42. Found: C, 53.77; H, 4.31; N, 2.41.

$[(\eta^5\text{-}C_5Me_4C_6H_4C_6H_5)Ir(2\text{-}dfphpy)Cl]$ (ZL103). The synthesis was performed as for ZL107 using $[(\eta^5\text{-}C_5Me_4C_6H_4C_6H_5)IrCl_2]_2$ (53 mg, 0.05 mmol), 2-(2,4-difluorophenyl)pyridine (19 mg, 0.10 mmol), and sodium acetate (16 mg, 0.20 mmol). Yield: 25 mg (37%). $^1$H NMR ($CDCl_3$): δ=8.53 (d, 1H, J=5.5 Hz), 8.19 (d, 1H, J=8.5 Hz), 7.64 (m, 5H), 7.50 (m, 4H), 7.38 (t, 1H, J=7.3 Hz), 7.22 (d, 1H, J=8.3 Hz), 6.96 (t, 1H, J=6.5 Hz), 6.51 (t, 1H, J=10.3 Hz), 1.81 (s, 3H), 1.77 (s, 3H), 1.75 (s, 3H), 1.59 (s, 3H). Anal. Calcd for $C_{32}H_{27}ClF_2NIr$ (691.23): C, 55.60; H, 3.94; N, 2.03. Found: C, 55.96; H, 3.95; N, 2.08. Crystals suitable for X-ray diffraction were obtained by slow evaporation of a methanol/diethyl ether solution at ambient temperature.

$[(\eta^5\text{-}C_5Me_4C_6H_5)Ir(dpq)Cl]PF_6$ (ZL89). A solution of $[(\eta^5\text{-}C_5Me_4C_6H_5)IrCl_2]_2$ (46 mg, 0.05 mmol) and ligand dipyrido[3,2-f:2',3'-h]quinoxaline (dpq, 23 mg, 0.10 mmol) in MeOH (40 mL) was heated under reflux in an $N_2$ atmosphere for 2 h and filtered. The volume was slowly reduced to half on a rotary evaporator and $NH_4PF_6$ (45 mg, 0.28 mmol) was added. After standing at 277 K, a microcrystalline product formed. This was collected by filtration, washed with diethyl ether, and recrystallized from methanol/diethyl ether. Yield: 44 mg (55%). $^1$H NMR($CDCl_3$): δ=9.68 (d, 2H, J=8.5 Hz), 9.13 (s, 2H), 8.96 (d, 2H, J=6.0 Hz), 8.06 (dd, 2H, J=8.0 Hz), 7.72 (m, 2H), 7.59 (m, 3H), 1.91 (s, 6H), 1.83 (s, 6H). Anal. Calcd for $C_{29}H_{25}ClF_6IrN_4P$ (802.10): C, 43.42; H, 3.14; N, 6.98. Found: C, 43.21; H, 3.21; N, 6.86.

$[(\eta^5\text{-}C_5Me_4C_6H_5)Ir(dppz)Cl]Cl$ (ZL93). A solution of $[(\eta^5\text{-}C_5Me_4C_6H_5)IrCl_2]_2$ (46 mg, 0.05 mmol) and ligand dipyrido[3,2-a:2',3'-c]phenazine (dppz, 28 mg, 0.10 mmol) in MeOH (40 mL) was heated under reflux in an $N_2$ atmosphere for 2 h and filtered. The volume was slowly reduced to 2 mL on a rotary evaporator. After standing at 277 K, a microcrystalline product formed. This was collected by filtration, washed with diethyl ether, and recrystallized from methanol/diethyl ether. Yield: 45 mg (60%). $^1$H NMR(DMSO-$d_6$): δ=9.79 (d, 2H, J=8.3 Hz), 9.15 (d, 2H, J=6.0 Hz), 8.52 (dd, 2H, J=6.3 Hz), 8.31 (dd, 2H, J=7.8 Hz), 8.21 (dd, 2H, J=6.5

Hz), 7.54 (m, 2H), 7.51 (m, 3H), 1.87 (s, 6H), 1.76 (s, 6H). Anal. Calcd for $C_{33}H_{27}Cl_2IrN_4$ (742.12): C, 53.37; H, 3.66; N, 7.54. Found: C, 53.14; H, 3.61; N, 7.60.

$[(\eta^5\text{-}C_6Me_4C_6H_4C_6H_5)Ir(dpq)Cl]Cl$ (ZL94). The synthesis was performed as for ZL93 using $[(\eta^5\text{-}C_5Me_4C_6H_4C_6H_5)IrCl_2]_2$ (53 mg, 0.05 mmol) and ligand dipyrido[3,2-a:2',3'-c]phenazine (dppz, 28 mg, 0.10 mmol). Yield: 33 mg (43%). $^1$H NMR(MeOD-$d_4$): δ=9.82 (d, 2H, J=8.3 Hz), 9.30 (s, 2H), 9.24 (d, 2H, J=6.0 Hz), 8.28 (dd, 2H, J=8.0 Hz), 7.83 (m, 2H), 7.76 (m, 4H), 7.52 (t, 2H, J=7.3 Hz), 7.44 (t, 1H, J=7.3 Hz), 1.97 (s, 6H), 1.90 (s, 6H). Anal. Calcd for $C_{35}H_{29}Cl_2IrN_4$ (768.14): C, 54.68; H, 3.80; N, 7.29. Found: C, 54.29; H, 3.71; N, 7.34.

$[(\eta^5\text{-}C_5Me_4C_6H_4C_6H_5Pr(dppz)Cl]Cl$ (ZL95). The synthesis was performed as for ZL93 using $[(\eta^5\text{-}C_5Me_4C_6H_4C_6H_5)IrCl_2]_2$ (53 mg, 0.05 mmol) and ligand dipyrido[3,2-a:2',3'-c]phenazine (dppz, 28 mg, 0.10 mmol). Yield: 37 mg (45%). $^1$H NMR(MeOD-$d_4$): δ=9.90 (d, 2H, J=8.3 Hz), 9.19 (d, 2H, J=6.0 Hz), 8.50 (dd, 2H, J=6.3 Hz), 8.26 (dd, 2H, J=7.6 Hz), 8.15 (dd, 2H, J=6.7 Hz), 7.81 (m, 2H), 7.77 (m, 4H), 7.50 (t, 2H, J=7.6 Hz), 7.41 (t, 1H, J=7.6 Hz), 1.95 (s, 6H), 1.89 (s, 6H). Anal. Calcd for $C_{39}H_{21}C_2IrN_4$ (818.16): C, 57.21; H, 3.82; N, 6.84. Found: C, 56.86; H, 3.69; N, 6.76.

$[(\eta^5\text{-}C_5Me_4C_3H_7)IrCl_2]_2$ (ZL97). A solution of $IrCl_3 \cdot nH_2O$ (1.0 g, 3.3 mmol) and tetramethyl(n-propyl)cyclopentadiene (1.0 g, 6.0 mmol) in MeOH (60 mL) was heated under reflux in an $N_2$ atmosphere for 48 h. The reaction mixture was allowed to cool to ambient temperature and the dark green precipitate was filtered off. The volume of the dark red filtrate was reduced to ca. 15 mL on a rotary evaporator. Upon cooling to ambient temperature, red-orange crystalline appeared which was collected by filtration. The product was washed with methanol and diethyl ether and dried in air. Yield: 0.5 g (32%). $^1$H NMR (CDCl$_3$): δ=2.13 (t, 2H, J=7.5 Hz), 1.62 (s, 6H), 1.60 (s, 6H), 1.44 (m, 2H), 0.94 (t, 3H, J=7.3 Hz). Anal. Calcd for $C_{24}H_{38}ClIr_2$ (852.80): C, 33.80; H, 4.49. Found: C, 33.81; H, 4.46.

$[(\eta^5\text{-}C_5Me_4C_3H_7)Ir(2\text{-}phpy)Cl]$ (ZL100). A solution of $[(\eta^5\text{-}C_5Me_5)IrCl_2]_2$ (40 mg, 0.05 mmol), 2-phenylpyridine (15 mg, 0.10 mmol) and sodium acetate (16 mg, 0.20 mmol) in $CH_2Cl_2$ (15 ml) was stirred for 12 h at ambient temperature. The solution was filtered through celite and rotary evaporated to dryness, then washed with diethyl ether. The product was crystallized from CHCl$_3$/hexane. Yield: 39 mg (72%). $^1$H NMR (CDCl$_3$): δ=8.70 (d, 1H, J=5.8 Hz), 7.81 (m, 2H), 7.65 (m, 2H), 7.20 (t, 1H, J=7.2 Hz), 7.06 (m, 2H), 2.04 (m, 2H), 1.72 (s, 6H), 1.69 (s, 6H), 1.45 (m, 2H), 0.94 (t, 3H, J=7.3 Hz). Anal. Calcd for $C_{23}H_{27}ClIrN$ (545.14): C, 50.67; H, 4.99; N, 2.57. Found: C, 50.80; H, 4.96; N, 2.64. Crystals suitable for X-ray diffraction were obtained by slow evaporation of a methanol/diethyl ether solution at ambient temperature.

$[(\eta^5\text{-}C_5Me_5)Ir(2\text{-}phpy)(9\text{-}EtG\text{-}N7)]NO_3$ (ZL47G). A solution of $[(\eta^5\text{-}C_5Me_5)Ir(2\text{-}phpy)Cl]$ (ZL47) (52 mg, 0.10 mmol) and AgNO$_3$ (17 mg, 0.10 mmol) in MeOH (10 mL) and water (20 mL) was stirred at ambient temperature for 24 h. The precipitate (AgCl) was removed by filtration through a glass wool plug, and 9-ethylguanine (19 mg, 0.11 mmol) was added to the filtrate. The reaction mixture was stirred at ambient temperature for 12 h. The solvents were removed in vacuo, the residue extracted with $CH_2Cl_2$ (10 mL), and the volume reduced to ca. 2 mL on a rotary evaporator. A yellow precipitate formed at 253 K on addition of hexane and was collected by filtration, washed with diethyl ether and dried in air. Yield: 23 mg (32%). $^1$H NMR (MeOD-$d_4$): δ=9.35 (d, 1H, J=5.8 Hz), 8.10 (d, 1H, J=7.5 Hz), 7.84 (d, 1H, J=8.0 Hz), 7.79 (t, 1H, J=7.0 Hz), δ=7.72 (d, 1H, J=7.5 Hz), 7.44 (t, 1H, J=7.8 Hz), 7.42 (s, 1H), 7.26 (t, 1H, J=6.3 Hz), 7.21 (t, 1H, J=8.0 Hz), 3.82 (q, 2H, J=7.3 Hz), 1.62 (s, 15H), 1.12 (t, 3H, J=7.3 Hz). Anal. Calcd for $C_{28}H_{32}IrN_7O_4$ (722.82): C, 46.53; H, 4.46; N, 13.56. Found: C, 46.74; H, 4.21; N, 13.23%. Crystals suitable for X-ray diffraction were obtained as ZL47G.1.5CH$_2$Cl$_2$ by slow evaporation of a CH$_2$Cl$_2$/hexane solution at ambient temperature.

$[(\eta^5\text{-}C_5Me_4C_6H_4C_6H_5)Ir(2\text{-}phpy)(py)]PF_6$ (ZL105). A solution of $[(\eta^5\text{-}C_5Me_4C_6H_4C_6H_5)Ir(2\text{-}phpy)Cl]$ (ZL49) (33 mg, 0.05 mmol) and AgNO$_3$ (9 mg, 0.05 mmol) in MeOH (10 mL) and water (20 mL) was stirred at ambient temperature for 24 h. The precipitate (AgCl) was removed by filtration through a glass wool plug, and pyridine (40 mg, 0.50 mmol) was added to the filtrate. The reaction mixture was stirred at ambient temperature for 12 h. The volume was slowly reduced to half on a rotary evaporator and NH$_4$PF$_6$ (45 mg, 0.28 mmol) was added. The yellow precipitate that formed was collected by filtration, washed with diethyl ether, and recrystallized from methanol/diethyl ether. Yield: 27 mg (32%). $^1$H NMR(CDCl$_3$): δ=8.97 (d, 1H, J=5.8 Hz), 8.50 (d, 2H, J=6.0 Hz), 7.76 (m, 3H), 7.66 (m, 2H), 7.51 (d, 2H, J=7.2 Hz), 7.41 (m, 5H), 7.33 (m, 4H), 7.18 (t, 1H, J=7.6 Hz), 6.87 (d, 2H, J=7.6 Hz), 1.86 (s, 3H), 1.78 (s, 3H), 1.62 (s, 3H), 1.57 (s, 3H). Anal. Calcd for $C_{37}H_{34}F_6IrN_2P$ (843.86): C, 52.66; H, 4.06; N, 3.32. Found: C, 52.86; H, 3.99; N, 3.40.

X-ray Crystal Structures. The X-ray crystal structures of $[(\eta^5\text{-}C_5Me_5)Ir(2\text{-}phpy)(9\text{-}EtG\text{-}N7)]NO_3.1.5CH_2Cl_2$ (ZL47G.1.5CH$_2$Cl$_2$), $[(\eta^5\text{-}C_5Me_5)Ir(2\text{-}phq)Cl]$ (ZL68), $[(\eta^5\text{-}C_5Me_4C_3H_7) Ir(2\text{-}phpy)Cl]$ (ZL100) and $[(\eta^5\text{-}C_5Me_4C_6H_4C_6H_5)Ir(2\text{-}dfphpy)Cl]$ (ZL103) were determined. The complexes adopt the expected half-sandwich pseudo-octahedral "three-leg piano-stool" geometry with the iridium bound to $\eta^5$-cyclopentadienyl ligand (Ir to ring centroid 1.819-1.829 Å), a chelating ligand, and a chloride (2.395-2.401 Å) or 9-EtG (2.114 Å).

Hydrolysis Studies. The hydrolysis of complexes $[(\eta^5\text{-}C_5Me_5)Ir(2\text{-}phpy)Cl]$ (ZL47), $[(\eta^5\text{-}C_5Me_4C_6H_4C_6H_5)Ir(2\text{-}phpy)Cl]$ (ZL49), $[(\eta^5\text{-}C_5Me_5) Ir(2\text{-}phq)Cl]$ (ZL68), $[(\eta^5\text{-}C_5Me_5) Ir(tpy)Cl]$ (ZL69), $[(\eta^5\text{-}C_5Me_5)Ir(2\text{-}dfphpy)Cl]$ (ZL74) and $[(\eta^5\text{-}C_5Me_4C_6H_5)Ir(2\text{-}phpy) Cl]$ (ZL107) in 20% MeOD-$d_4$/80% D$_2$O (v/v) was monitored by $^1$H NMR at different temperatures. The presence of methanol ensured the solubility of the complexes. All these Ir$^{III}$ complexes undergo rapid hydrolysis since the hydrolysis equilibrium reached by the time the first $^1$H NMR spectrum was acquired (~5 min) even at 278 K. To confirm the hydrolysis of the complexes, NaCl was added to an equilibrium solution containing the chlorido complexes and their aqua adducts to give concentrations of 4, 23 and 104 mM NaCl, mimicking the chloride concentrations in cell nucleus, cell cytoplasm and blood plasma, respectively.[21] $^1$H NMR spectra were then recorded within 10 min of the additions at 298 K. With addition of NaCl, $^1$H NMR peaks corresponding to the chlorido complexes increased in intensity whilst peaks for the aqua adducts decreased in intensity. These data confirm the formation of the aqua adducts and the reversibility of the process. On the basis of $^1$H NMR peak integrals, anation of aqua complexes were almost complete on addition of NaCl since almost no hydrolyzed complexes were found to be present in 104 mM [Cl] or in 23 mM [Cl], and only around 5% of aqua complexes was observed at 4 mM [Cl] after 10 min with no further change after equilibrium.

p$K_a$* Determination. The p$K_a$ of coordinated water can have a significant influence on its reactivity since M-OH bonds are often much less labile than M-OH$_2$ bonds.[23]

When the pH* values of the solutions were increased from about 2 to 10, the NMR peaks assigned to aqua complexes ZL47A, ZL49A, ZL69A and ZL74A gradually shifted to high field in the spectrum. The resulting pH titration curves were fitted to the modified Henderson-Hasselbalch equation, from which the $pK_a^*$ values of the coordinated water were determined. This gave rise to $pK_a$ values between 8.31 and 8.87 (Table 8).

TABLE 8

$pK_a^*$ and $pK_a$ values for the deprotonation of the coordinated $D_2O$ in aqua complexes ZL47A, ZL49A, ZL69A and ZL74A

| Aqua Complex | $pK_a^*$ | $pK_a$ |
|---|---|---|
| $[(\eta^5\text{-}C_5Me_5)Ir(tpy)(D_2O)]^+$ (ZL69A) | 9.10 | 8.87 |
| $[(\eta^5\text{-}C_5Me_5)Ir(2\text{-dfphpy})(D_2O)]^+$ (ZL74A) | 8.51 | 8.32 |
| $[(\eta^5\text{-}C_5Me_5)Ir(2\text{-phpy})(D_2O)]^+$ (ZL47A) | 8.97 | 8.75 |
| $[(\eta^5\text{-}C_5Me_4C_6H_4C_6H_5)Ir(2\text{-phpy})(D_2O)]^+$ | 8.50 | 8.31 |

Interactions with Nucleobases. Since DNA is a potential target site for transition metal anticancer complexes,[23] the binding of 9-ethylguanine (9-EtG) to complexes ZL47, ZL49, ZL69, ZL74 and ZL107 was studied. Addition of 1 mol equiv of 9-EtG to an equilibrium solution of the complexes (ca. 1.0 mM) in 20% $MeOD\text{-}d_4$/80% $D_2O$ (v/v, at 310 K) resulted in 100% of guanine adducts formed after 24 h.

Cytotoxicity. The cytotoxicity of complexes ZL64, ZL109, ZL68, ZL69, ZL74, ZL100, ZL101, ZL103, ZL105, ZL107, ZL89, ZL93, ZL94, ZL95, towards A2780 human ovarian cancer cells has been investigated. The screening result of $IC_{50}$ values (concentration at which 50% of the cell growth is inhibited) for all complexes are all <30 µM with many less than 10 µM or even 1 µM (see Table 9) and are thus deemed as active. The introduction of a biphenyl substituent into the Cp* ring gives rise to higher cytotoxicity. The tetramethyl(biphenyl)cyclopentadienyl complexes ZL103 and ZL105 are one order of magnitude more potent than the pentamethylcyclopentadienyl complexes ZL68, ZL69 and ZL74.

TABLE 9

| Complex | X | $Cp^x$ | L-L' | $IC_{50}$ (µM) | Comments |
|---|---|---|---|---|---|
| ZL64 | Cl | Cp* | azpy-NMe$_2$ | <30$^a$ | |
| ZL109 | Cl | $Cp^{xph}$ | azpy-NMe$_2$ | <10$^a$ | |
| ZL110 | Cl | $Cp^{xph}$ | pp-NMe$_2$ | $^d$ | |
| ZL68 | Cl | Cp* | 2-phq | 2.55 ± 0.03 | b, c |
| ZL69 | Cl | Cp* | tpy | 3.28 ± 0.14 | b |
| ZL74 | Cl | Cp* | 2-dfphpy | 6.53 ± 0.50 | b |
| ZL100 | Cl | $Cp^{xpr}$ | 2-phpy | <10$^a$ | c |
| ZL107 | Cl | $Cp^{xph}$ | 2-phpy | 2.14 ± 0.50 | |
| ZL103 | Cl | $Cp^{xbiph}$ | 2-dfphpy | 0.67 ± 0.11 | c |
| ZL105 | py | $Cp^{xbiph}$ | 2-phpy | 0.12 ± 0.02 | |
| ZL47G | 9-EtG | Cp* | 2-phpy | $^d$ | c |
| ZL89 | Cl | $Cp^{xph}$ | dpq | <5$^a$ | |
| ZL94 | Cl | $Cp^{xbiph}$ | dpq | <5$^a$ | |
| ZL93 | Cl | $Cp^{xph}$ | dppz | <5$^a$ | |
| ZL95 | Cl | $Cp^{xbiph}$ | dppz | <5$^a$ | |
| Cisplatin | | | | 1.2 | |

$^a$Data from screening test.
$^b$Complex has been listed before but synthesis is included here.
$^c$X-ray crystal structure obtained.
$^d$Not determined.

Six complexes, $[(\eta^5\text{-}C_5Me_4C_6H_4C_6H_5)Ir(bpy)Cl]PF_6$ (ZL25, bpy=2,2'-bipyridine), $[(\eta^5\text{-}C_5Me_4C_6H_5)Ir(phen)Cl]PF_6$ (ZL33, phen=1,10-phenanthroline), $[(\eta^5\text{-}C_5Me_4C_6H_4C_6H_5)Ir(pico)Cl]$ (ZL43, pico=picolinate), $[(\eta^5\text{-}C_5Me_5)Ir(2\text{-phpy})Cl]$ (ZL47), $[(\eta^5\text{-}C_5Me_4C_6H_4C_6H_5)Ir(2\text{-ph}_{PY})(D_2O)Cl]$ (ZL49) and $[(\eta^5\text{-}C_5Me_4C_6H_4C_6H_5)Ir(phen)Cl]PF_6$ (ZL54), were selected by Developmental Therapeutics Program of National Cancer Institute (NCI, U.S.A.) for in vitro screening test, in which 5 complexes except ZL43 are selected for further testing. The five complexes were tested on ca. 60 cell lines within nine tumour type subpanels at five concentrations ranging from 0.01 to 100 µM. Three endpoints are calculated: GI50 (the concentration that causes 50% cell growth inhibition), TGI (the concentration where causes 100% cell growth inhibition), and LC50 (the concentration that the drug decreases the original cell number by 50%).

Figure 11:
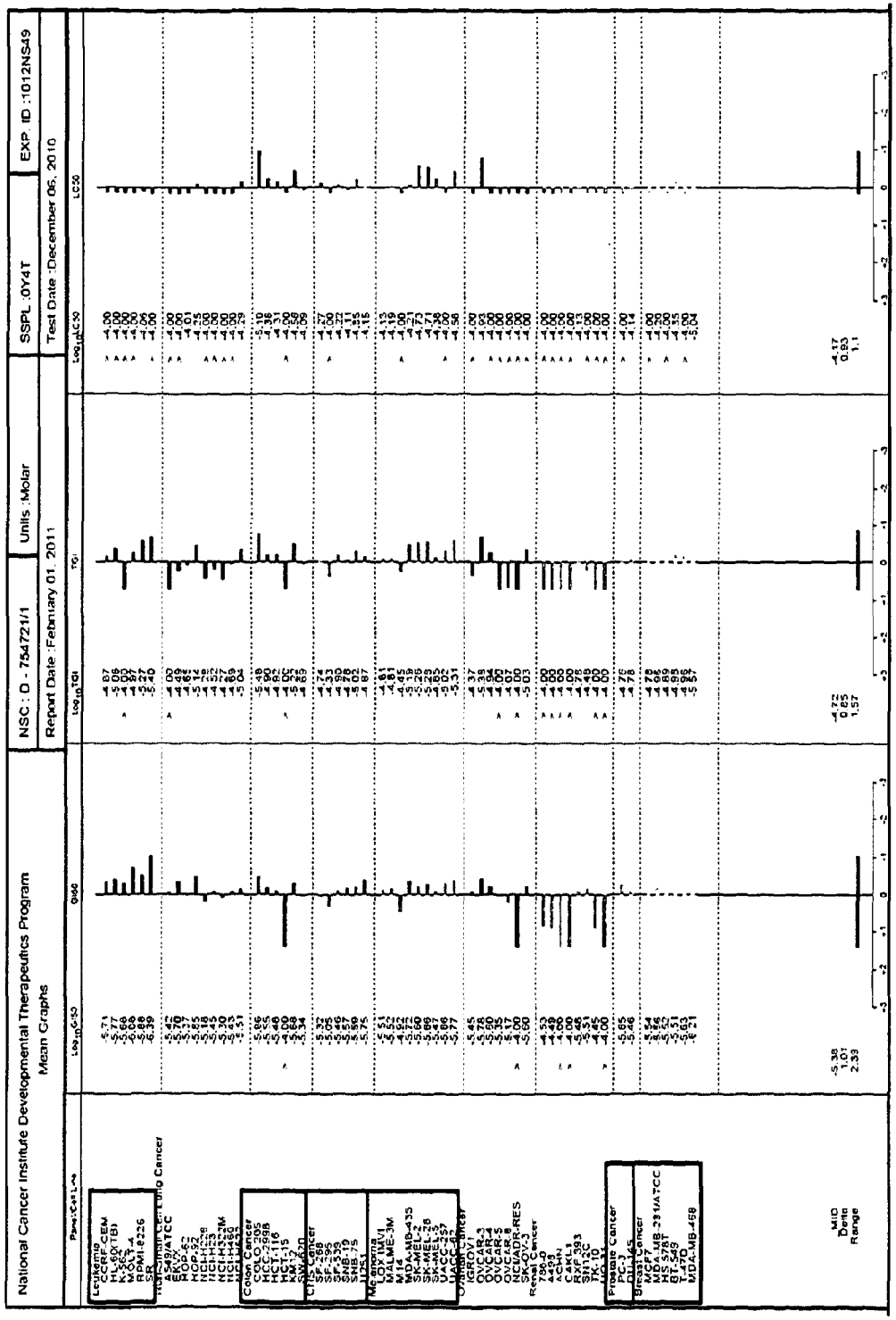
FIGS. 11-13 show the mean graphs for complexes ZL25, ZL33, and ZL49, respectively from the NCI developmental therapeutic program. Each boxed area shows where a particular compound is most active.
Figure 12:
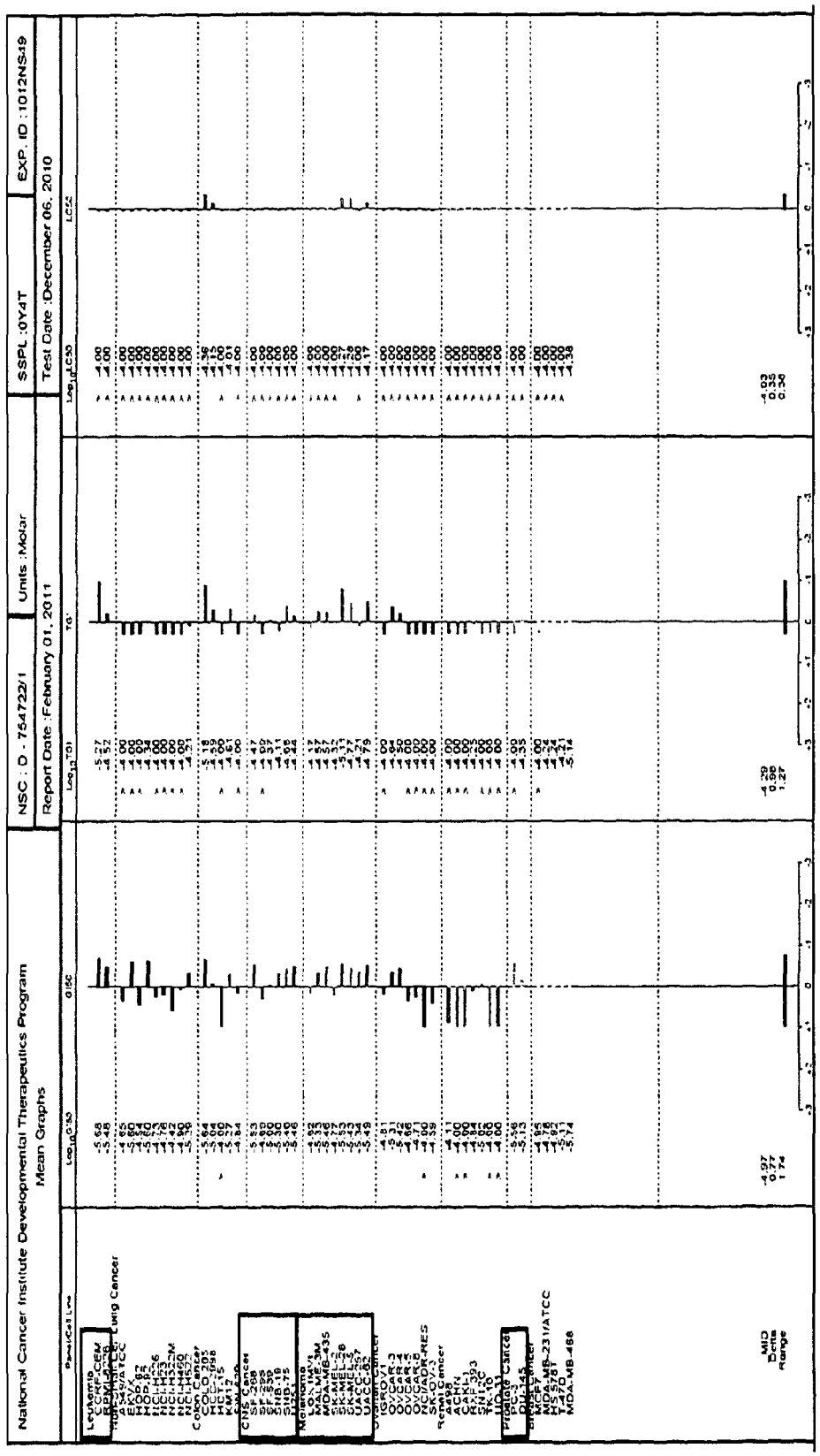
Figure 13:
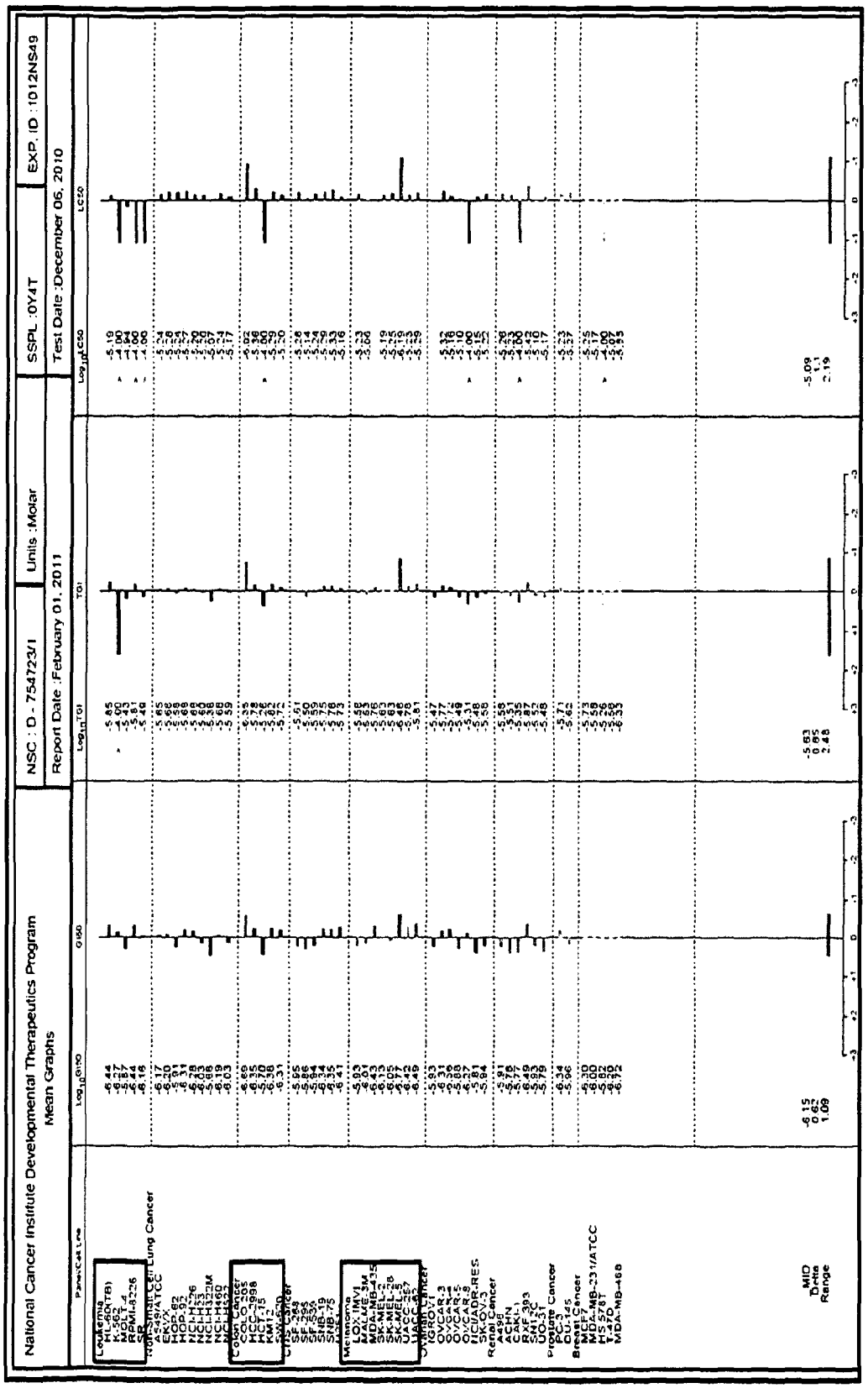

The mean graphs for complexes ZL25, ZL33 and ZL49 are listed in FIGS. 11-13. Complex ZL33, containing $Cp^{xph}$ and 1,10-phenanthroline N,N-chelating ligand, is selective for leukemia, CNS cancer, melanoma, and prostate cancer, which are highlighted by red square in FIG. 2. Similar to ZL33, complex ZL25, containing $Cp^{xbiph}$ and 2,2'-bipyridine N,N-chelating ligand, shows selectivity with higher activity not only towards leukemia, CNS cancer, melanoma, and prostate cancer, but also against colon cancer and breast cancer. Complex ZL49, containing $Cp^{xbiph}$ and 2-phenylpyridine C,N-chelating ligand, is the most potent among the 3 complexes and is selective for leukemia, colon cancer, and melanoma, particularly active towards colon COLO 205, melanoma SK-MEL-5, and breast MDA-MB-468, with GI50 values less than 0.2 µM. The mean graph midpoint (MID) GI50, TGI and LC50 for complexes ZL25, ZL33 and ZL49 are listed in Table 10. Both the extended phenyl ring and chelating ligand play significant role on the cytotoxicity of $Ir^{III}$ complexes.

TABLE 10

Mean graph midpoint (MID) GI50, TGI and LC50 values of ZL25, ZL33 and ZL49$^a$.

| Complex | GI50 (µM) | TGI (µM) | LC50 (µM) |
|---|---|---|---|
| ZL25 | 4.1 | 19.1 | 67.6 |
| ZL33 | 10.7 | 51.3 | 93.3 |
| ZL49 | 0.71 ± 0.01 | 2.19 ± 0.15 | 7.08 ± 1.05 |

$^a$based on testing twice using almost identical panels

Studies in Relation to Mechanisms of Action

The coenzyme couple NADH/NAD$^+$ plays a major role in controlling the redox balance inside cells. A similar role is played by NADPH/NADP$^+$. NAD(P)H provides reducing equivalents for protecting cells against reactive oxygen species (ROS) which can cause damage to cells.

Although the transfer of hydride (H$^-$) to NAD$^+$ using organometallic rhodium complexes of the type described in the application has been described previously: e.g.

Bioorganometallic chemistry. 13. Regioselective reduction of NAD(+) models, 1-benzylnicotinamde triflate and beta-nicotinamide ribose-5'-methyl phosphate, with in situ generated [CpRh(Bpy)H](+): structure-activity relationships, kinetics, and mechanistic aspects in the formation of the 1,4-NADH derivatives. Lo H C, Leiva C, Buriez O, Kerr J B, Olmstead M M, Fish R H *Inorg Chem.* 2001 Dec. 17; 40(26):6705-16.

there appear to be no reports of the transfer of hydride from NADH or NADPH to Ir(III) or Rh(III). Unexpectedly we have found that such reactions are facile and therefore could play a role in the mechanism of anticancer activity of the complexes described in this application. Some examples of the detection of hydride transfer are described below.

Reaction of ZL33Aqua Complex with 1,4-NADH

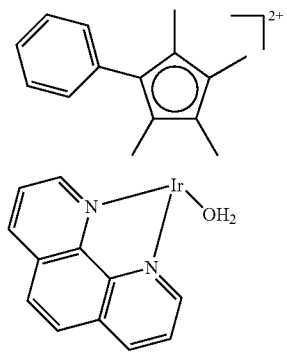

ZL33A (active against A2780 with $IC_{50}$ of 6.7 µM)

Materials. β-nicotinamide adenine dinucleotide ($NAD^+$) and β-nicotinamide adenine dinucleotide reduced dipotassium salt (1,4-NADH) were purchased from Sigma-Aldrich. To generate the aqua complex $[(\eta^5\text{-}C_5Me_4C_6H_5)Ir(phen)(H_2O)]^{2+}$ (ZL33A), the chlorido complex $[(\eta^5\text{-}C_5Me_4C_6H_5)Ir(phen)Cl]PF_6$ ($ZL33PF_6$) was dissolved in 10% $MeOD\text{-}d_4$/90% $H_2O$ (v/v), and 0.98 mol equiv of $AgNO_3$ were added, respectively. The solutions were stirred for 24 h at 298 K, and AgCl was removed by filtration.

Results.

Reaction Between ZL33A and 1,4-NADH

To explore the interaction between 1,4-NADH and the aqua complex ZL33A, two reactions were carried out with mol ratio 3:1 and 1:1.5, respectively.

Three equiv of 1,4-NADH was added to a 2 mM solution of $[(\eta^5\text{-}C_5Me_4C_6H_5) Ir(phen)(H_2O)]^{2+}$ (ZL33A) at room temperature. The colour of solution changed from light yellow to yellow immediately. The $^1H$ NMR spectra of the resulting solution were recorded at 298 K at various time intervals during 33 h, 40% of 1,4-NADH reacted with the aqua complex rapidly within 10 min. A sharp singlet peak corresponding to the hydride complex $[(\eta^5\text{-}C_5Me_4C_6H_5)Ir(phen)(H)]^+$ in the high-field region (−10.8 ppm) of the spectrum within the first 10 min of reaction was recorded. It suggests that a fast hydride-transfer reaction from 1,4-NADH to the $Ir^{III}$ complex ZL33A to generate a Ir—H specie could be taking place. The appearance of a new set of signals which are attributable to the formation of $NAD^+$ was also detected during the first 10 min of reaction. The pH* of the solutions changed from 6.6 to 10.1 after the addition of 1,4-NADH. A 2D $^1H\text{-}^1H$ TOCSY NMR spectrum was recorded after 22 h to assign the proton resonances. However, there are still some aqua complex exist when the NADH is excess. So there should be an equilibrium between the transformation of $NAD^+$ and 1,4-NADH. The relative concentration ratios of different species (assume concentration of $NAD^+$ as one unit) based on the integrals of $^1H$ NMR spectra at different time intervals are listed in Table 11.

When the starting mol ratio between 1,4-NADH and aqua complex ZL33A is 1:1.5, all the 1,4-NADH reacted with the aqua complex rapidly and transferred to $NAD^+$ before the first $^1H$ NMR spectrum was recorded (<10 min), A sharp singlet peak corresponding to the hydride peak in the high-field region (−10.8 ppm) of the spectrum was recorded, which decreased with time and disappeared (transferred to aqua complex ZL33A) after 10 h. The pH of the solution changed from 6.6 before addition of 1,4-NADH to 9.3 after 10 h. The relative concentration ratios of different species (assume concentration of $NAD^+$ as one unit) based on the integrals of $^1H$ NMR spectra at different time intervals are listed in Table 12, which show that the concentration of hydride complex decreased with the increase of aqua complex ZL33A. After 10 h, no hydride peaks were detected and the major species exist in the solution were $NAD^+$ and aqua complex ZL33A.

TABLE 11

The relative concentration ratios of different species based on the integrals of $^1H$ NMR spectra at different time intervals in the reaction of $[(\eta^5\text{-}C_5Me_4C_6H_5)Ir(phen)(H_2O)]^{2+}$ (ZL33A) with 1,4-NADH (molar ratios 1:3) at 298 K.

| | Integral ratio based on $^1H$ NMR peaks | | | |
|---|---|---|---|---|
| Time | $NAD^+$ | 1,4-NADH | Aqua complex | Hydride complex |
| 10 min | 1 | 1.45 | 0.25 | 0.6 |
| 22 h | 1 | 1.3 | 0.16 | 0.5 |
| 33 h | 1 | 0.5 | 0.45 | 0.07 |

TABLE 12

The relative concentration ratios of different species based on the integrals of $^1H$ NMR spectra at different time intervals in the reaction of $[(\eta^5\text{-}C_5Me_4C_6H_5)Ir(phen)(H_2O)]^{2+}$ (ZL33A) with 1,4-NADH (molar ratios 1.5:1) at 298 K.

| | Integral ratio based on 1H NMR peaks | | |
|---|---|---|---|
| Time | $NAD^+$ | Aqua complex | Hydride complex |
| 10 min | 1 | 1 | 0.5 |
| 2 h | 1 | 1.3 | 0.25 |
| 10 h | 1 | 1.6 | 0 |

Transformation of Pyruvate to Lactate

For this experiment, 3 mol equiv of 1,4-NADH was added to a 1 mM solution of $[(\eta^5\text{-}C_5Me_4C_6H_5)Ir(phen)(H_2O)]^{2+}$ (ZL33A) in 10% $MeOD\text{-}d_4$/90% $H_2O$ (v/v) at room temperature. A sharp singlet peak corresponding to the hydride peak in the high-field region (−10.8 ppm) of the spectrum was recorded. 3 mol equiv of sodium pyruvate was added to the NMR tube. A doublet peak around 1.45 ppm corresponding to protons of methyl group of lactate was recorded. The intensity of methyl group of hydride specie decreased with the formation of lactate.

The similar experiments were also performed between NADPH and ZL33A, which showed the hydride-transfer reactions also occurred in that case.

Reaction of ZL33A with NADH Produced from Reaction of Alcohol Dehydrogenase Enzyme and $NAD^+$ This section demonstrates that when NADH is produced as a result of an enzymatic reaction if will react quickly with iridium complexes of the type described here.

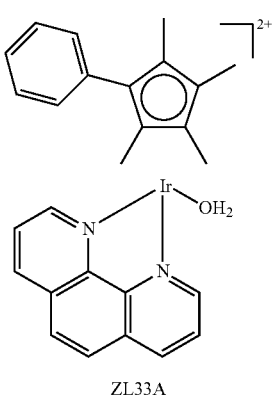

ZL33A

Materials and Calculations for Concentrations. Alcohol dehydrogenase from *saccharomyces cerevisiae* (ADH), β-Nicotinamide adenine dinucleotide (NAD⁺) were purchased from Sigma-Aldrich. To generate the aqua complex ZL33A, chlorido complex ZL33 was dissolved in $H_2O$ and 0.98 mol equiv of $AgNO_3$ were added. The solution was stirred for 24 h at 298 K, and AgCl was removed by filtration. The concentrations of NADH, NAD⁺ and ADH in this study obtained from Beer-Lambert law and their extinction coefficients are listed below: 259 nm $E(NAD^+)^{24}=16900$ $M^{-1}cm^{-1}$; 339 nm $E(NADH)^{25}=6220$ $M^{-1}cm^{-1}$; 280 nm $E^{1\%}(ADH)^{26}=14.6$.

Results

Reactions of ZL33A with NADH produced from reaction of ADH and NAD⁺ in a mixture solution (0.15 ml $Na_2HPO_4$/ $NaH_2PO_4$ buffer, 0.05 ml ethanol and 0.05 ml $H_2O$, pH=7.2) were recorded by UV-Vis at 298 K from 220 nm to 500 nm. NAD⁺, ZL33A, and ADH were recorded separately as control by UV-Vis before mixed together, with final concentration 34 µM, 32 µM and $3.8\times10^{-3}$ mg/ml, respectively. After the mix of NAD⁺ and ADH (final concentrations are 34 µM and $3.8\times10^3$ mg/ml, respectively), UV-Vis spectrum was recorded after 10 min. No change was observed after 30 min. An absorption band at 339 nm was observed, suggested the generation of NADH (33 µM). Then to this solution, ZL33A (final concentration is 32 µM) was added and the resulted UV-Vis spectrum was recorded immediately. The absorption at 339 nm decreased after addition of ZL33A, indicating the NADH was reacted with aqua complex ZL33A. The concentration of reacted NADH was 29 µM. This experiment shows that the NADH produced as a result of the enzymatic reaction can react quickly with the biologically active iridium complexes.

REFERENCES

1. White, C.; Yates, A.; Maitlis, P. M. *Inorg. Synth.* 1992, 29, 228-234.
2. Schäfer, S.; Ott, I.; Gust, R.; Sheldrick, W. S. *Eur. J. Inorg. Chem,* 2007, 3034-3046.
3. Schäfer, S.; Sheldrick, W. S. *J. Organomet. Chem.* 2007, 692, 1300-1309.
4. Scharwitz, M. A.; Ott, I.; Gust, R.; Kromm, A.; Sheldrick, W. S. *J. Inorg. Biochem.* 2008, 102, 1623-1630.
5. Herebian, D.; Sheldrick, W. S. *J. Chem. Soc., Dalton Trans.,* 2002, 966-974.
6. Wirth, Stefan.; Rohbogner, C. J.; Cieslak, M.; Kazmierczak-Baranska, J.; Donevski, S.; Nawrot, B.; Lorenz, I. P. *J. Biol. Inorg. Chem.* 2010, 15, 429-440.
7. Gras, M.; Therrien, B.; Süss-Fink, G.; Casini, A.; Edafe, F.; Dyson, P. J. *J. Organomet. Chem.* 2010, 695, 1119-1125.
8. Youinou, M-T. *J. Organomet. Chem.* 1989, 363, 197-208.
9. Gorol, M.; Roesky, H. W.; Noltemeyer, M.; Schmidt, H-G. *Eur. J. Inorg. Chem.* 2005, 4840-4844.
10. Björgvinsson, M.; Halldorsson, S.; Arnason, I.; Magull, J.; Fenske, D.; *J. Organomet. Chem.* 1997, 544, 207-215.
11. Boutadla, Y.; Al-Duaij, O.; Davies, D. L.; Griffith, G. A.; Singh, K. *Organometallics.* 2009, 28, 433-440.
12. Davies, D. L.; Al-Duaij, O.; Fawcett, J.; Giardiello, M.; Hilton, S. T.; Russell, D. R. *Dalton. Trans.,* 2003, 4132-4238.
13. Sheldrick, G. M. SHELXL-97, Program for the refinement of crystal structures; University of Gottingen: Göttingen, Germany, 1997.)
14. Krezel, A.; Bal, W. *J. Inorg. Biochem.* 2004, 98, 161-166.
15. Skehan, P.; Storeng, R.; Scudiero, D.; Monks, A.; McMahon, J.; Vistica, D.; Warren, J. T.; Bokesch, H.; Kenney, S.; Boyd, M. R. *J. Natl. Cancer Inst.* 1990, 82, 1107-1112.
16. Lee, S. A.; Eyeson, R.; Cheever, M. L.; Geng, J. M.; Verkhusha, V. V.; Burd, C.; Overduin, M.; Kutateladze, T. G. *Proc. Natl. Acad. Sci. U.S.A.* 2005, 102, 13052-13057.
17. Sigel, R. K. O.; Sabat, M.; Freisinger, E.; Mower, A.; Lippert, B. *Inorg. Chem.* 1999, 38, 1481-1490.
18. (a) Deubel, D. V.; Lau, J. K.-C. *Chem. Commun.* 2006, 2451-2453. (b) Zhang, C. X.; Lippard, S. J. *Curr. Opin. Chem. Biol.* 2003, 7, 481-489.
19. Aird, R. E.; Cummings, J.; Ritchie, A. A.; Muir, M.; Morris, R. E.; Chen, H.; Sadler, P. J.; Jodrell, D. I. *Br. J. Cancer,* 2002, 86, 1652-1657.
20. Delgadillo, A.; Romo, P.; Leiva, A. M.; Loeb, B. *Helvetica Chimica Acta* 2003, 86, 2110-2120.
21. Jennerwein, M.; Andrews, P. A. *Drug Metab. Dispos.* 1995, 23, 178-184.
22. Chen, H.; Parkinson, J. A.; Morris, R. E.; Sadler, P. J. *J. Am. Chem. Soc.* 2003, 125, 173-186.
23. (a) Zhang, C. X.; Lippard, S. J. Curr. Opin. Chem. Biol. 2003, 7, 481-489. (b) Deubel, D. V.; Lau, J. K.-C. *Chem. Commun.* 2006, 2451-2453.
24. Dawson, R. B. Data for biochemical research; 3rd ed.; Clarendon Press: Oxford, 1985.
25. Smeets, E. H. J.; Muller, H.; De Wael, *J. Clin. Chim. Acta* 1971, 33, 379-386.26. Bühner, M.; Sund, H. *Eur. J. Biochem* 1969, 11, 73-79.

The invention claimed is:

1. A method of treating or reducing the likelihood of a disease involving abnormal cell proliferation, the method comprising administering, to a subject in need of such treatment, a therapeutically effective amount of a compound of formula (I):

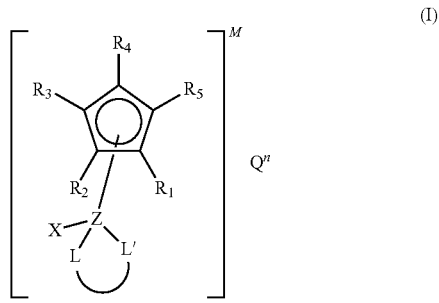

or a dinuclear or polynuclear form thereof, wherein
Z is iridium or rhodium
X is a halo or donor ligand;

each $R_1$-$R_5$ is independently H, methyl, a substituted or unsubstituted alkyl or alkenyl, an aryl, a substituted or unsubstituted saturated or unsaturated cyclic or heterocyclic ring, $NH_2$, $NO_2$, $OR^1$, $COOR^1$; with the proviso that at least one of said $R_1$-$R_5$ groups is selected from a substituted or unsubstituted alkyl or alkenyl, an aryl, a substituted or unsaturated saturated or unsaturated cyclic or heterocyclic ring, $NH_2$, $NO_2$, $OR^1$, or $COOR^1$;

wherein $R^1$ is a $C_1$-$C_6$ alkyl or alkenyl, an aryl, a saturated or unsaturated cyclic or heterocyclic ring, or a trimethylsilyl;

L-L' is a chelating ligand;

Q is an ion and is either present or absent; and

M and n are charges, independently either absent or selected from a positive or negative whole integer, or solvates or prodrugs thereof with the proviso that when $R_1$-$R_5$ are each independently methyl, then L and L' are not each independently N or O;

wherein the disease is a cancer selected from carcinoma of the bladder, breast, or colon, colon adenocarcinoma and colon adenoma, kidney, epidermal, liver, lung, adenocarcinoma, small cell lung cancer and non-small cell lung carcinomas, oesophagus, gall bladder, ovary, pancreas, exocrine pancreatic carcinoma, stomach, cervix, thyroid, prostate, or skin, squamous cell carcinoma, leukemia, acute lymphocytic leukemia, B-cell lymphoma, T-cell lymphoma, Hodgkin's lymphoma, non-Hodgkin's lymphoma, hairy cell lymphoma, or Burkett's lymphoma, acute and chronic myelogenous leukemias, myelodysplastic syndrome, or promyelocytic leukemia, thyroid follicular cancer, fibrosarcoma or habdomyosarcoma, astrocytoma, neuroblastoma, glioma or schwannoma, melanoma, seminoma, teratocarcinoma, osteosarcoma, xenoderoma pigmentoum, keratoctanthoma, thyroid follicular cancer, or Kaposi's sarcoma.

2. The method according to claim 1, wherein Z is iridium.

3. The method according to claim 1, wherein $R_1$-$R_5$ is methyl and L is N and L' is C or S.

4. The method according to claim 1, wherein $R_1$-$R_5$ when not H or methyl, is a saturated or unsaturated cyclic or heterocyclic ring or rings.

5. The method according to claim 1, wherein the L-L' ligand comprises an unsaturated or saturated ring which is present as part of the chelating ligand and is substituted with one or more groups or fused or otherwise substituted to one or more further unsaturated or saturated rings, which may or may not be heterocyclic.

6. The method according to claim 1, wherein L is N and L' is C or S.

7. The method according to claim 1, wherein at least one of $R_1$-$R_5$ is a substituted $C_1$-$C_{10}$ alkyl or alkenyl, or an unsubstituted $C_2$-$C_{10}$ alkyl or alkenyl.

8. The method according to claim 1, wherein $R_1$-$R_5$ when not H or methyl is a phenyl or bi-phenyl ring structure.

9. A method of treating or reducing the likelihood of a disease involving abnormal cell proliferation, the method comprising administering, to a subject in need of such treatment, a therapeutically effective amount of a compound of formula (II)

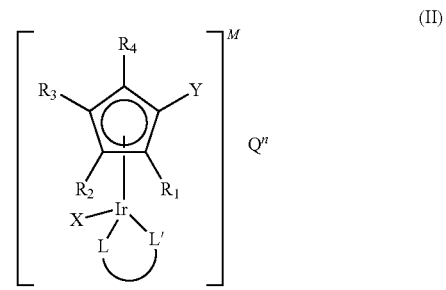

or a dinuclear or polynuclear from thereof, where X, Z, L-L', Q, M and n are the same as defined in relation to the claim 1, $R_1$-$R_4$ are H or methyl and Y is independently selected from a substituted or unsubstituted alkyl or alkenyl, an aryl, a substituted or unsubstituted saturated or unsaturated cyclic or heterocyclic ring, $NH_2$, $NO_2$, OR', COOR';

wherein R' is a $C_1$-$C_6$ alkyl or alkenyl, an aryl, a saturated or unsaturated cyclic or heterocyclic ring or a trimethylsilyl.

10. The method of claim 9, wherein Y is a saturated or unsaturated cyclic or heterocyclic ring or rings.

11. The method according to claim 9, wherein Y is a phenyl or bi-phenyl ring structure.

12. A method of treating cancer, selected from leukaemia, CNS cancer, melanoma, prostate cancer, colon cancer or breast cancer, the method comprising administering, to a subject in need of such treatment, a therapeutically effective amount of a compound of formula (I):

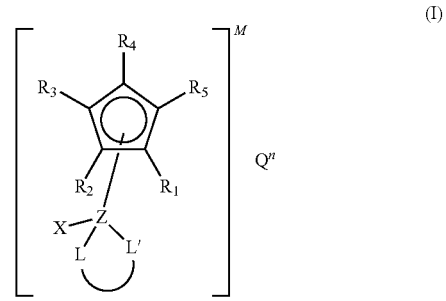

or a dinuclear or polynuclear form thereof, wherein Z is iridium or rhodium;

X is a halo or donor ligand;

each $R_1$-$R_5$ is independently H, methyl, a substituted or unsubstituted alkyl or alkenyl, an aryl, a substituted or unsubstituted saturated or unsaturated cyclic or heterocyclic ring, $NH_2$, $NO_2$, $OR^1$, $COOR^1$; with the proviso that at least one of said $R_1$-$R_5$ groups is selected from a substituted or unsubstituted alkyl or alkenyl, an aryl, a substituted or unsubstituted saturated or unsaturated cyclic or heterocyclic ring, $NH_2$, $NO_2$, $OR^1$, or $COOR^1$;

wherein $R^1$ is a $C_1$-$C_6$ alkyl or alkenyl, an aryl, a saturated or unsaturated cyclic or heterocyclic ring, or a trimethylsilyl;

L-L' is a chelating ligand;

Q is an ion and is either present or absent; and

M and n are charges, independently either absent or selected from a positive or negative whole integer,
or solvates or prodrugs thereof
with the proviso that when $R_1$-$R_5$ are each independently methyl, then L and L' are not each independently N or O.

* * * * *